United States Patent
Yu et al.

(10) Patent No.: US 8,247,805 B2
(45) Date of Patent: Aug. 21, 2012

(54) MATERIAL FOR ORGANIC PHOTOELECTRIC DEVICE INCLUDING ELECTRON TRANSPORTING UNIT AND HOLE TRANSPORTING UNIT, AND ORGANIC PHOTOELECTRIC DEVICE INCLUDING THE SAME

(75) Inventors: Eun-Sun Yu, Anyang (KR); Nam-Soo Kim, Bucheon (KR); Young-Hoon Kim, Anyang (KR); Mi-Young Chae, Yongin (KR); Eui-Su Kang, Anyang (KR)

(73) Assignee: Cheil Industries, Inc., Gumi-si, Kyeongsangbuk-do (KR)

( * ) Notice: Subject to any disclaimer, the term of this patent is extended or adjusted under 35 U.S.C. 154(b) by 296 days.

(21) Appl. No.: 12/588,365

(22) Filed: Oct. 13, 2009

(65) Prior Publication Data
US 2010/0155706 A1 Jun. 24, 2010

Related U.S. Application Data

(63) Continuation of application No. PCT/KR2008/002098, filed on Apr. 14, 2008.

(30) Foreign Application Priority Data

Apr. 13, 2007 (KR) .................. 10-2007-0036407

(51) Int. Cl.
*H01L 35/24* (2006.01)
(52) U.S. Cl. ............... 257/40; 257/79; 257/E51.001
(58) Field of Classification Search .............. 257/40, 257/79, E51.001
See application file for complete search history.

(56) References Cited

U.S. PATENT DOCUMENTS

| | | |
|---|---|---|
| 2004/0086745 A1 | 5/2004 | Iwakuma et al. |
| 2004/0222414 A1 | 11/2004 | Ito et al. |
| 2008/0145699 A1 * | 6/2008 | Yabe et al. .................. 428/690 |
| 2012/0012830 A1 | 1/2012 | Kim et al. |

FOREIGN PATENT DOCUMENTS

| | | |
|---|---|---|
| EP | 926216 A1 * | 6/1999 |
| EP | 1 489 155 A1 | 12/2004 |
| JP | 2004-311404 A | 11/2004 |
| JP | 2007-067383 A | 3/2007 |
| WO | WO 2006/067976 A1 | 6/2006 |

* cited by examiner

*Primary Examiner* — Anthony Ho
(74) *Attorney, Agent, or Firm* — Lee & Morse, P.C.

(57) ABSTRACT

A material for an organic photoelectric device, the material including a compound including a pyridine

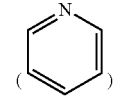

moiety, the compound being a bipolar organic compound including both a hole transporting unit and an electron transporting unit, the compound being represented by the following Formula 1:

[Formula 1]

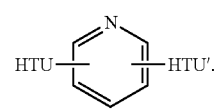

15 Claims, 26 Drawing Sheets

[Formula 1]

[Formula 2]

[Formula 6a]

[Formula 6b]

[Formula 6c]

[Formula 6d]

Compound (1)

Compound (2)

Compound (3)

Compound (4)

Compound (6)

Compound (8)

Compound (5)

Compound (7)

Compound (10)

Compound (12)

Compound (9)

Compound (11)

Compound (14)

Compound (16)

Compound (13)

Compound (15)

Compound (18)

Compound (20)

Compound (17)

Compound (19)

Compound (22)

Compound (24)

Compound (21)

Compound (23)

Compound (26)

Compound (28)

Compound (25)

Compound (27)

Compound (30)

Compound (29)

Compound (31)

Compound (32)

Compound (34)

Compound (33)

Compound (36)

Compound (38)

Compound (35)

Compound (37)

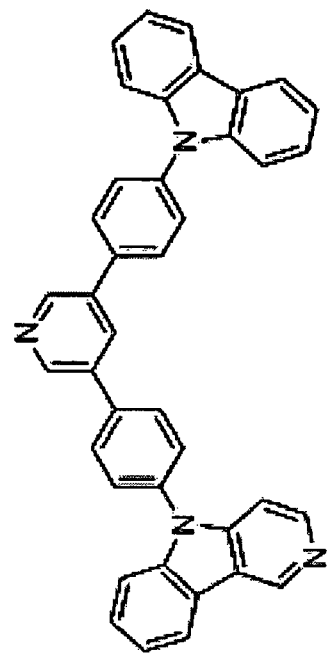
Compound (40)
FIG. 9K
Compound (39)
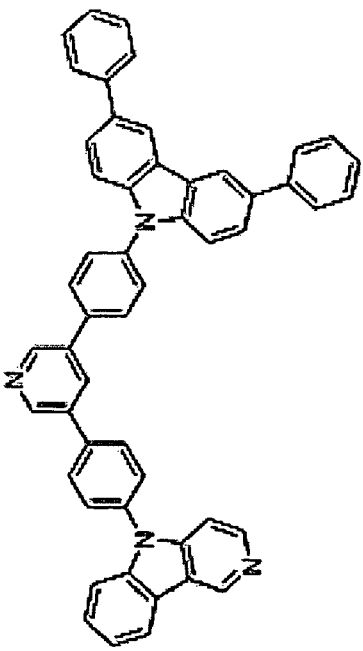
Compound (41)

[Formula 3]

[Formula 4]

[Formula 5]

Compound (42)

Compound (43)

Compound (44)

Compound (45)

Compound (46)

Compound (47)

Compound (49)

Compound (48)

Compound (51)

Compound (50)

Compound (52)

[Reaction Scheme 1]

[Reaction Scheme 2]

[Reaction Scheme 3]

[Reaction Scheme 4]

[Reaction Scheme 5]

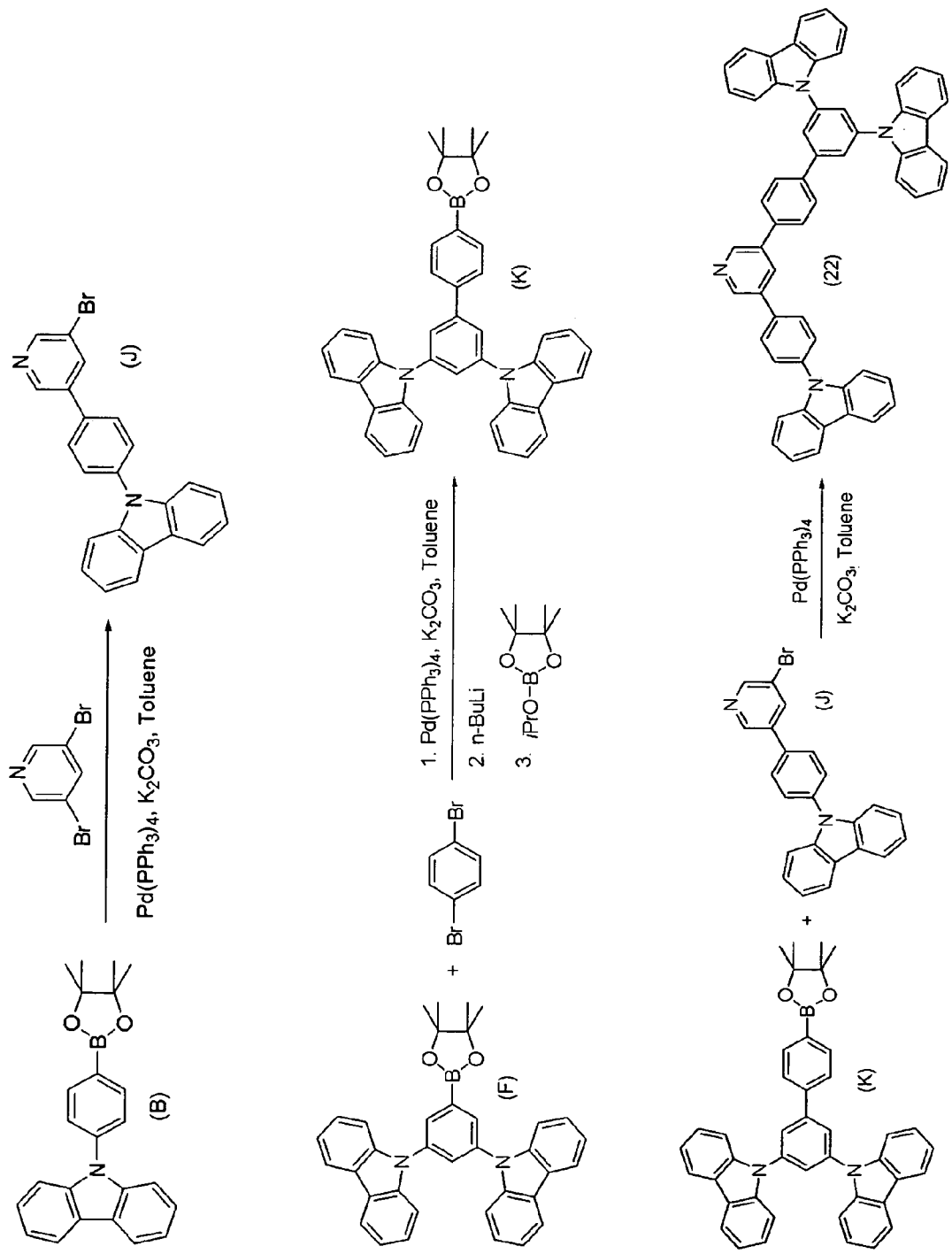
FIG. 19 [Reaction Scheme 6]

MATERIAL FOR ORGANIC PHOTOELECTRIC DEVICE INCLUDING ELECTRON TRANSPORTING UNIT AND HOLE TRANSPORTING UNIT, AND ORGANIC PHOTOELECTRIC DEVICE INCLUDING THE SAME

CROSS-REFERENCE TO RELATED APPLICATION

The present application is a continuation application of co-pending PCT Patent Application Serial No. PCT/KR2008/002098, entitled, "Material For Organic Photoelectric Device Including Electron Transporting Unit and Hole Transporting Unit, and Organic Photoelectric Device Including the Same," which was filed on Apr. 14, 2008, and is herein incorporated by reference in its entirety.

BACKGROUND OF THE INVENTION

1. Field

The present invention relates to a material for an organic photoelectric device and an organic photoelectric device including the same. More particularly, the present invention relates to a material for an organic photoelectric device having thermal stability due to a glass transition temperature (Tg) of 120° C. or more and a thermal decomposition temperature of 400° C. or more, having bipolar characteristics due to good hole and electron transporting properties, and being capable of realizing high efficiency of an organic photoelectric device, and an organic photoelectric device including the same.

2. Description of the Related Art

A photoelectric device is, in a broad sense, a device for transforming photo energy to electrical energy, and conversely, for transforming electrical energy to photo energy. The photoelectric device may be exemplified by an organic light emitting diode, a solar cell, a transistor, and so on.

Particularly, among these photoelectric devices, the organic light emitting device employing organic light emitting diodes (OLED) has recently drawn attention due to the increase in demand for flat panel displays.

The organic light emitting device transforms electrical energy into light by applying current to an organic light emitting material. It has a structure in which a functional organic material layer is interposed between an anode and a cathode.

The organic light emitting diode has similar electrical characteristics to those of light emitting diodes (LED) in which holes are injected from an anode and electrons are injected from a cathode, then the holes and electrons move to opposite electrodes and are recombined to form excitons having high energy. The formed excitons generate lights having a certain wavelength while shifting to a ground state.

Generally, the organic light emitting diode is composed of an anode of a transparent electrode, an organic thin layer of a light emitting region, and a metal electrode (cathode) formed on a glass substrate, in that order. The organic thin layer may includes an emission layer, a hole injection layer (HIL), a hole transport layer (HTL), an electron transport layer (ETL), or an electron injection layer (EIL). It may further include an electron blocking layer or a hole blocking layer due to the emission characteristics of the emission layer.

When the organic light emitting diode is applied with an electric field, the holes and electrons are injected from the anode and the cathode, respectively. The injected holes and electrons are recombined on the emission layer though the hole transport layer (HTL) and the electron transport layer (ETL) to provide light emitting excitons.

The provided light emitting excitons emit light by transiting to the ground state.

The light emitting may be classified as a fluorescent material including singlet excitons and a phosphorescent material including triplet excitons.

In other words, the duration of fluorescent emission is extremely short at several nanoseconds, but the duration of phosphorescent emission is relatively long such as at several microseconds, so that it provides a characteristic of extending the lifetime (emission duration) to more than that of the fluorescent emission.

In addition, evaluating quantum mechanically, when holes injected from the anode are recombined with electrons injected from the cathode to provide light emitting excitons, the singlet and the triplet are produced in a ratio of 1:3, in which the triplet light emitting excitons are produced at three times the amount of the singlet light emitting excitons in the organic light emitting diode.

Accordingly, the percentage of the singlet exited state is 25% (the triplet is 75%) in the case of a fluorescent material, so it has limits in luminous efficiency. On the other hand, in the case of a phosphorescent material, it can utilize 75% of the triplet exited state and 25% of the singlet exited state, so theoretically the internal quantum efficiency can reach up to 100%. When phosphorescent light emitting material is used, it has advantages in an increase in luminous efficiency of around four times than that of the fluorescent light emitting material.

In this structure, the efficiency and properties of the light emission diodes are dependent on the host material in the emission layer. According to studies regarding the emission layer (host), the organic host material can be exemplified by a material including naphthalene, anthracene, phenanthrene, tetracene, pyrene, benzopyrene, chrysene, pycene, carbazole, fluorene, biphenyl, terphenyl, triphenylene oxide, dihalobiphenyl, trans-stilbene, and 1,4-diphenylbutadiene.

Generally, the host material includes 4,4-N,N-dicarbazolebiphenyl (CBP) having a glass transition temperature of 110° C. or less and a thermal decomposition temperature of 400° C. or less, in which the thermal stability is low and the symmetry is excessively high. Thereby, it tends to crystallize and cause problems such as a short and a pixel defection according to results of thermal resistance tests of the devices.

In addition, most host materials including CBP are materials in which the hole transporting property is greater than the electron transporting property. In other words, as the injected hole transportation is faster than the injected electron transportation, the excitons are ineffectively formed in the emission layer. Therefore, the resultant device has deteriorated luminous efficiency.

Accordingly, in order to realize a highly efficient and long lifetime organic light emitting device, it is required to develop a phosphorescent host material having high electrical and thermal stability and that is capable of transporting both holes and electrons.

SUMMARY OF THE INVENTION

According to one embodiment of the present invention, provided is a material for an organic photoelectric device having thermal stability due to a glass transition temperature (Tg) of 120° C. or more and a thermal decomposition temperature of 400° C. or more, having bipolar characteristics due to good hole and electron transporting properties, and being capable of realizing a high efficiency organic photoelectric device. According to another embodiment of the present invention, provided is an organic photoelectric device having high luminous efficiency and a long life-span.

The embodiments of the present invention are not limited to the above technical purposes, and a person of ordinary skill in the art can understand other technical purposes.

One embodiment of the present invention provides a material for an organic photoelectric device that includes the compound represented by the following Formula 1. The material is a bipolar organic compound including both a hole transporting unit and an electron transporting unit.

At least one of the above and other features and advantages may be realized by providing a material for an organic photoelectric device, the material including a compound including a pyridine

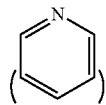

moiety, the compound being a bipolar organic compound including both a hole transporting unit and an electron transporting unit, the compound being represented by the following Formula 1:

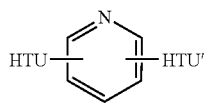

[Formula 1]

In Formula 1, the pyridine moiety may be a electron transporting unit, the HTU and HTU' may independently function as a hole transporting unit, and the HTU and HTU' may be the same or different.

The compound represented by Formula 1 may be further represented by the following Formula 2:

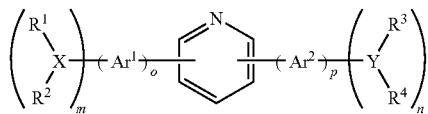

[Formula 2]

In Formula 2: X and Y may be independently selected from the group consisting of nitrogen (N), sulfur (S), and oxygen (O); $Ar^1$ and $Ar^2$ may be independently selected from the group consisting of a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene; $R^1$ to $R^4$ may be independently selected from the group consisting of a substituted or unsubstituted C6 to C30 aryl, a substituted or unsubstituted C6 to C30 arylene, a substituted or unsubstituted C2 to C30 heteroaryl, a substituted or unsubstituted C2 to C30 heteroarylene, a substituted or unsubstituted C1 to C30 alkyl, and a substituted or unsubstituted C1 to C30 alkylene, or $R^1$ and $R^2$ form a cyclic ring or $R^3$ and $R^4$ form a cyclic ring, when X is sulfur or oxygen, $R^2$ may be a unshared electron pair, and when Y is sulfur or oxygen, $R^4$ may be a unshared electron pair, and m and n may independently be integers ranging from 0 to 3, m+n may be more than or equal to 1, and o and p may be integers ranging from 0 to 2.

At least one of the groups $XR^1R^2$ and $YR^3R^4$ in Formula 2 may be represented by the following Formula 6a:

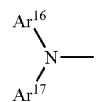

[Formula 6a]

In Formula 6a, $Ar^{16}$ and $Ar^{17}$ may be independently selected from the group consisting of a substituted or unsubstituted C6 to C30 aryl and a substituted or unsubstituted C2 to C30 heteroaryl.

At least one of the groups $XR^1R^2$ and $YR^3R^4$ in Formula 2 may be represented by the following Formula 6b:

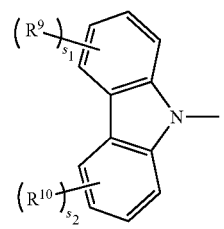

[Formula 6b]

In Formula 6b: $R^9$ and $R^{10}$ may independently be substituents selected from the group consisting of a substituted or unsubstituted C6 to C30 aryl, a substituted or unsubstituted C2 to C30 heteroaryl, a substituted or unsubstituted C1 to C30 alkyl, a substituted or unsubstituted C2 to C20 alkoxy, and $SiR_{15}R_{16}R_{17}$ (where $R_{15}$ to $R_{17}$ may be independently selected from the group consisting of a substituted or unsubstituted C1 to C30 alkyl, a substituted or unsubstituted C1 to C30 aryl, a substituted or unsubstituted C2 to C30 heteroaryl, a substituted or unsubstituted C3 to C30 cycloalkyl, a nitrile, a cyano, a nitro, a carbonyl, and an amide); and $s_1$ and $s_2$ may independently be integers ranging from 0 to 4.

At least one of the groups $XR^1R^2$ and $YR^3R^4$ in Formula 2 may be represented by the following Formula 6c:

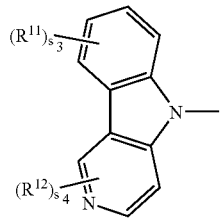

[Formula 6c]

In Formula 6c: $R^{11}$ and $R^{12}$ may independently be substituents selected from the group consisting of a substituted or unsubstituted C6 to C30 aryl, a substituted or unsubstituted C2 to C30 heteroaryl, a substituted or unsubstituted C1 to C30 alkyl, a substituted or unsubstituted C2 to C20 alkoxy, and $SiR_{15}R_{16}R_{17}$ (where $R_{15}$ to $R_{17}$ may be independently selected from the group consisting of a substituted or unsubstituted C1 to C30 alkyl, a substituted or unsubstituted C1 to C30 aryl, a substituted or unsubstituted C2 to C30 heteroaryl, a substituted or unsubstituted C3 to C30 cycloalkyl, a nitrile, a cyano, a nitro, a carbonyl, and an amide); and $s_3$ and $s_4$ may independently be integers ranging from 0 to 4.

At least one of the groups $XR^1R^2$ and $YR^3R^4$ in Formula 2 may be represented by the following Formula 6d:

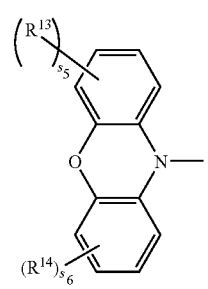

[Formula 6d]

In Formula 6d: $R^{13}$ and $R^{14}$ may independently be substituents selected from the group consisting of a substituted or unsubstituted C6 to C30 aryl, a substituted or unsubstituted C2 to C30 heteroaryl, a substituted or unsubstituted C1 to C30 alkyl, a substituted or unsubstituted C2 to C20 alkoxy, and $SiR_{15}R_{16}R_{17}$ (where $R_{15}$ to $R_{17}$ may be independently selected from the group consisting of a substituted or unsubstituted C1 to C30 alkyl, a substituted or unsubstituted C1 to C30 aryl, a substituted or unsubstituted C2 to C30 heteroaryl, a substituted or unsubstituted C3 to C30 cycloalkyl, a nitrile, a cyano, a nitro, a carbonyl, and an amide); and $s_5$ and $s_6$ may independently be integers ranging from 0 to 4.

The compound represented by Formula 2 may be a compound of the following Compounds (1) to (41), and combinations thereof:

Compound (1)

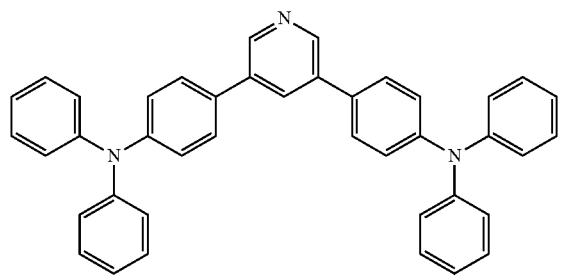

Compound (2)

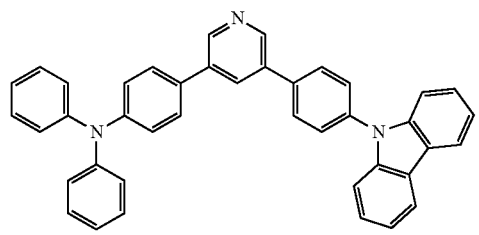

Compound (3)

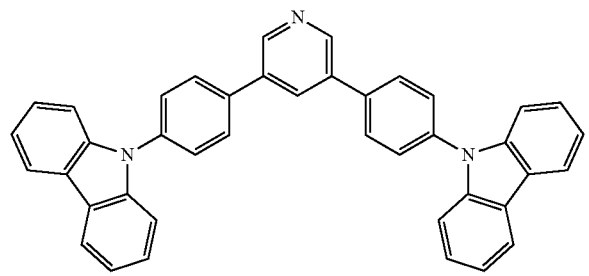

Compound (4)

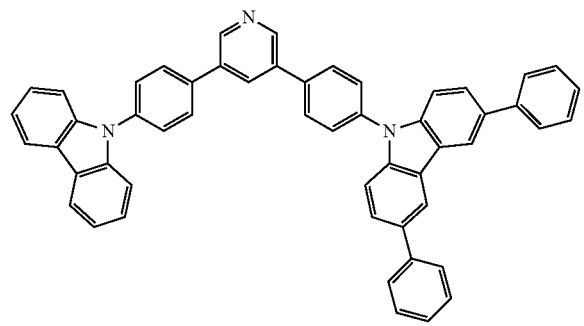

Compound (5)
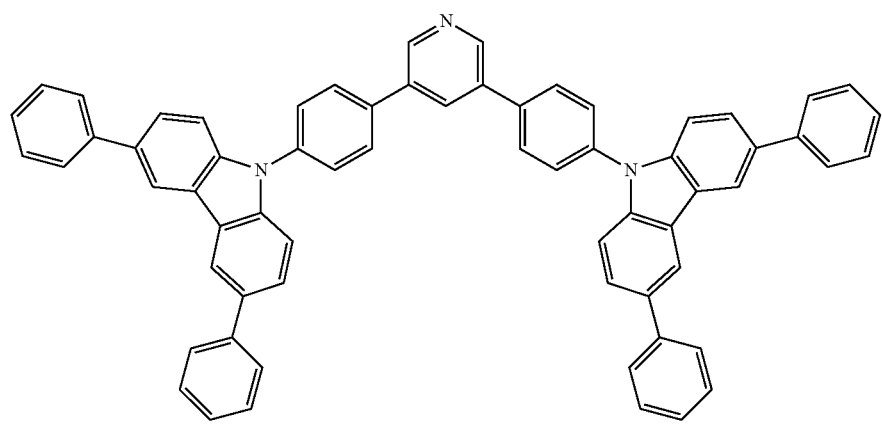
Compound (6)
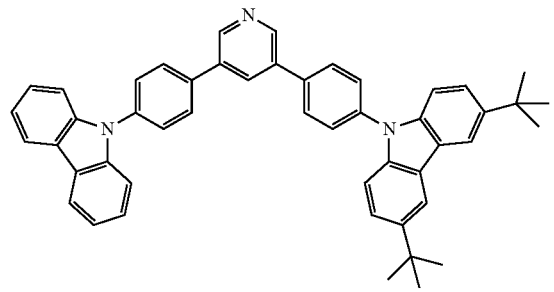
Compound (7)
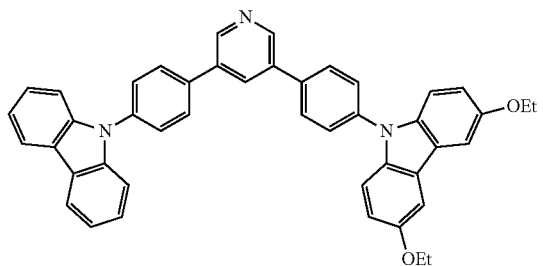
Compound (8)
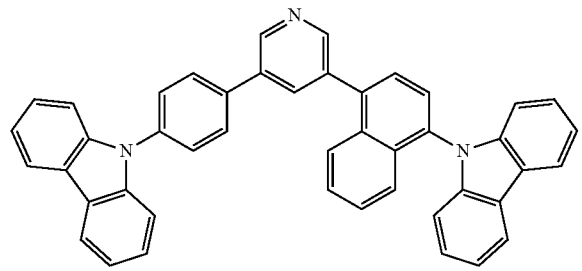
Compound (9)
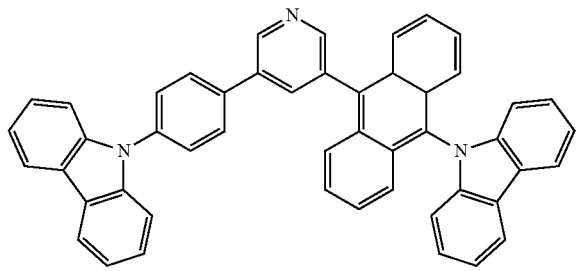
Compound (10)
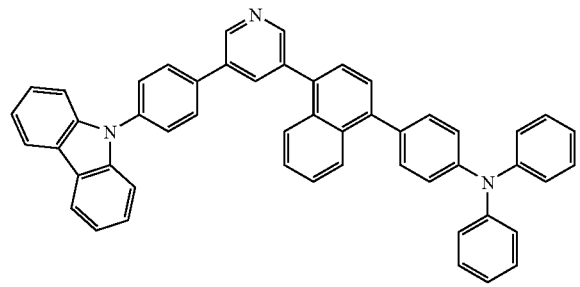
Compound (11)
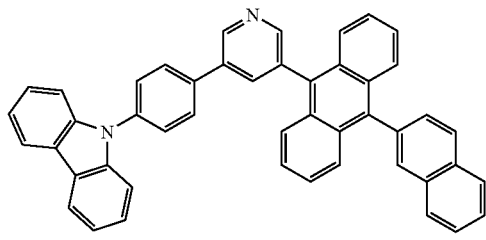

-continued
Compound (12)
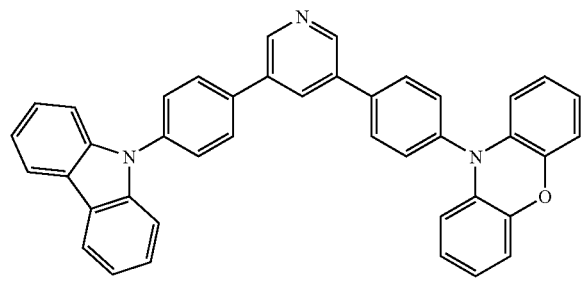
Compound (13)
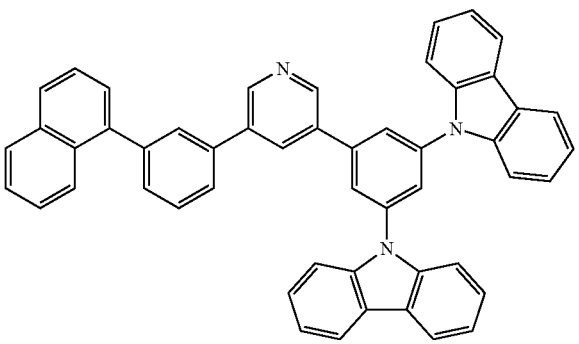
Compound (14)
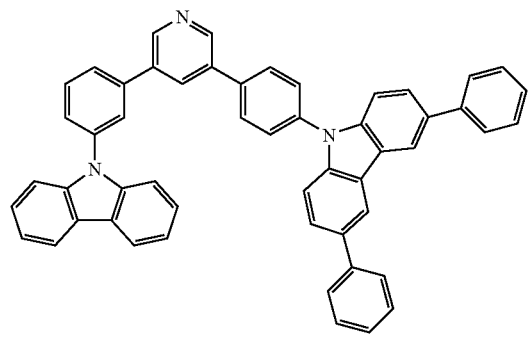
Compound (15)
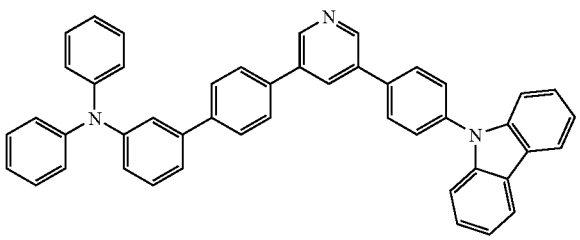
Compound (16)
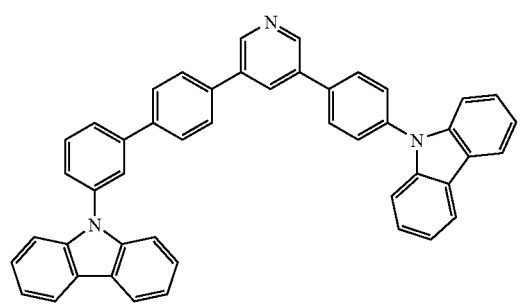
Compound (17)
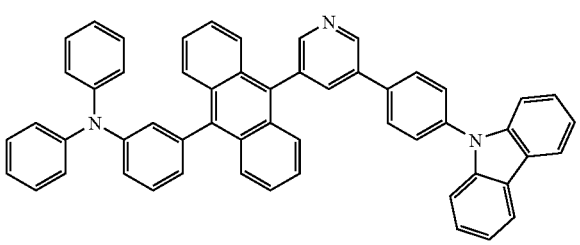
Compound (18)
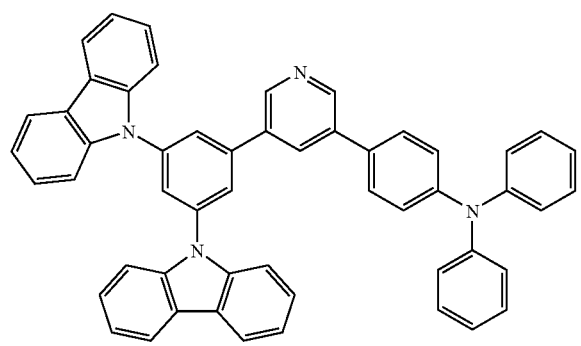
Compound (19)
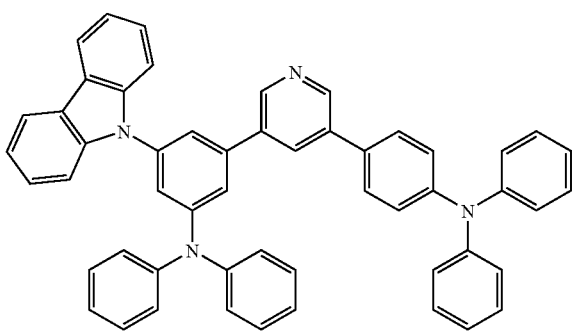

-continued
Compound (20)
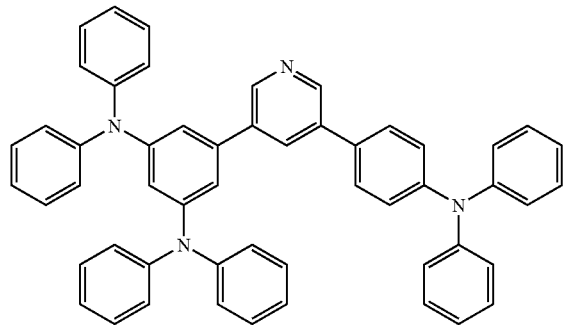
Compound (21)
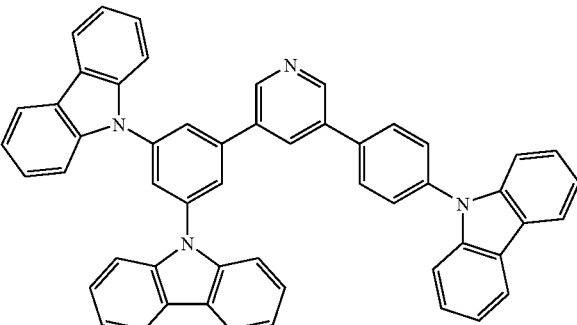
Compound (22)
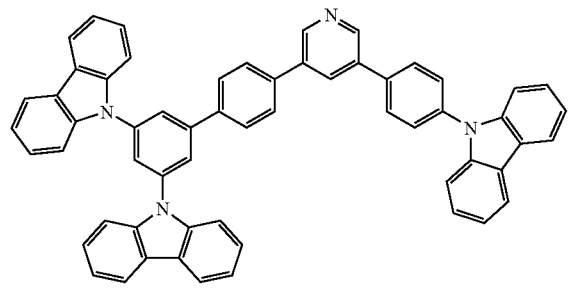
Compound (23)
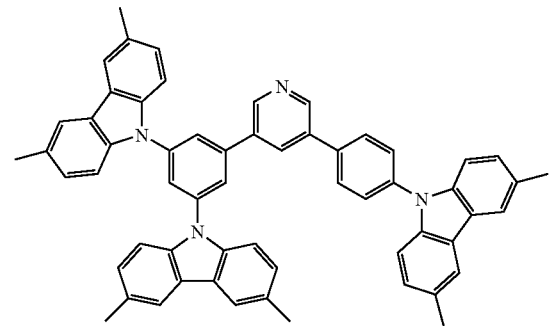
Compound (24)
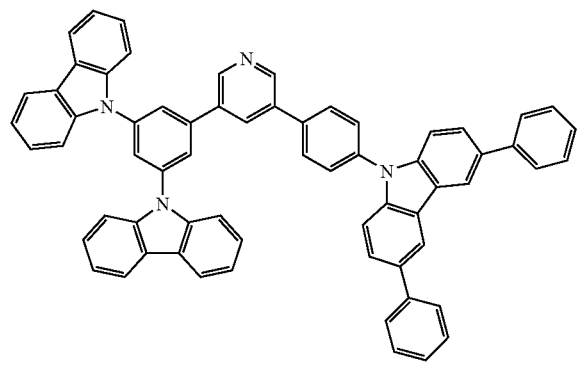
Compound (25)
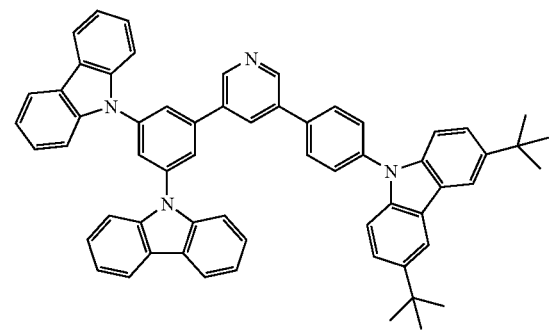
Compound (26)
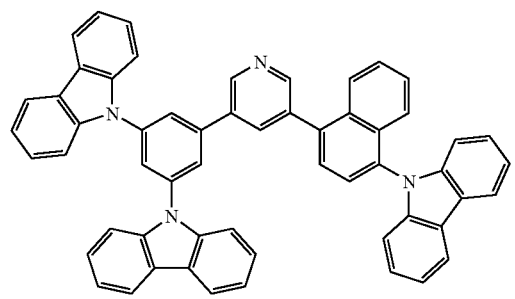
Compound (27)
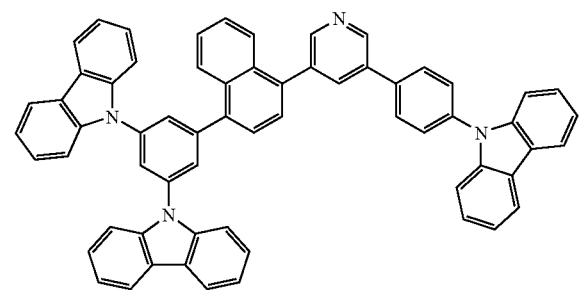

-continued
Compound (28)
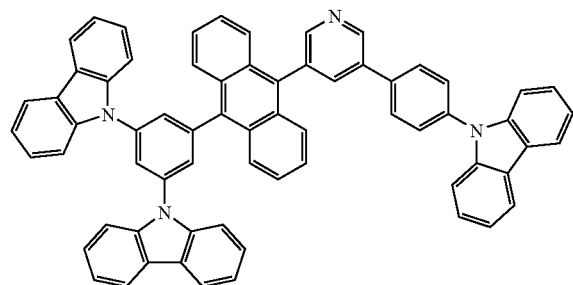
Compound (29)
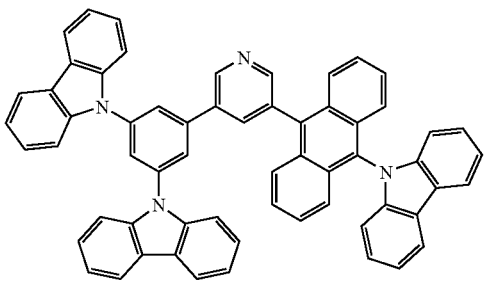
Compound (30)
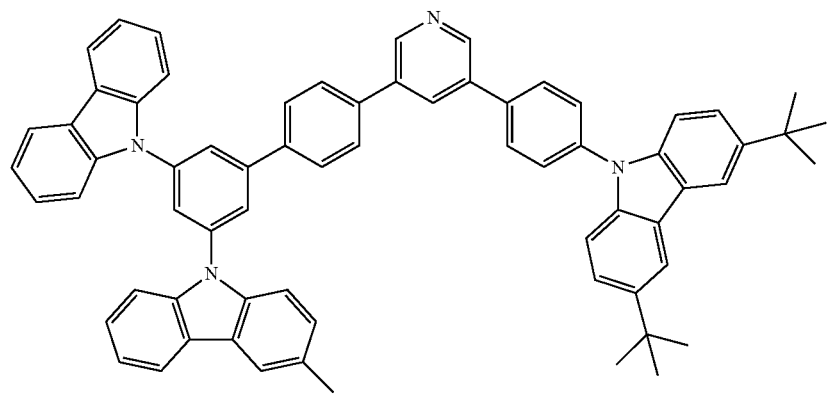
Compound (31)
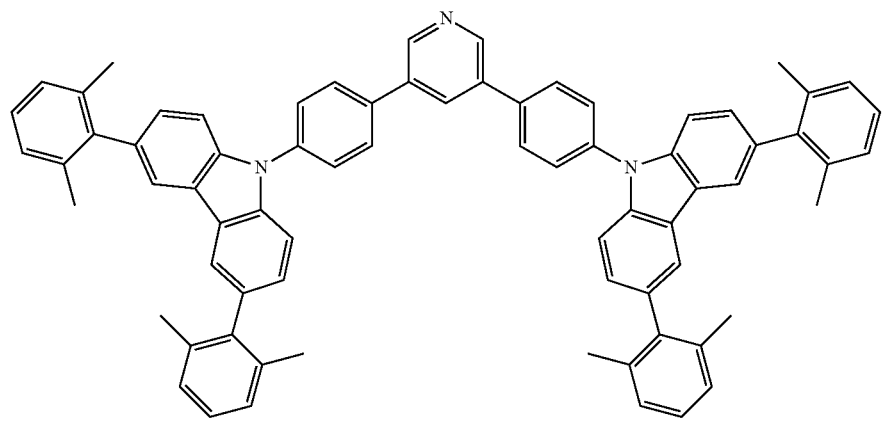
Compound (32)
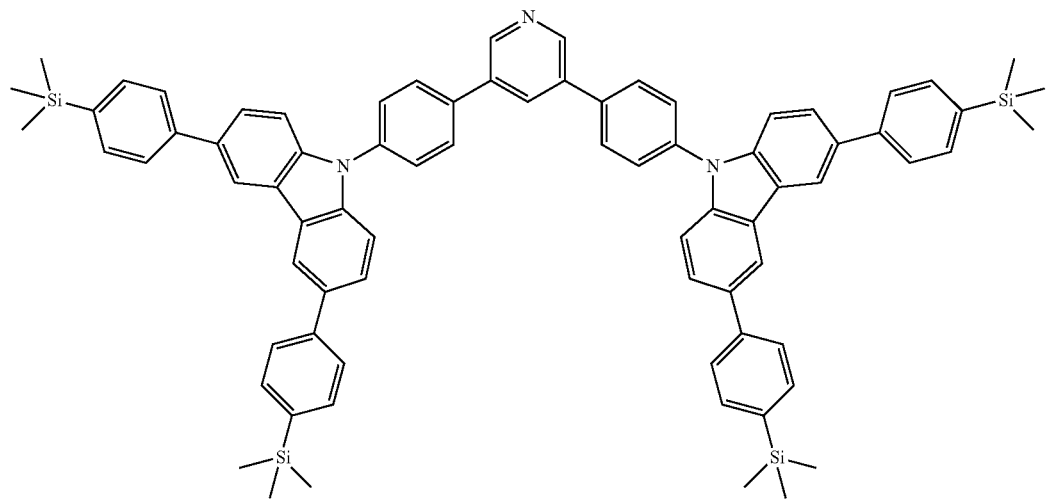

-continued
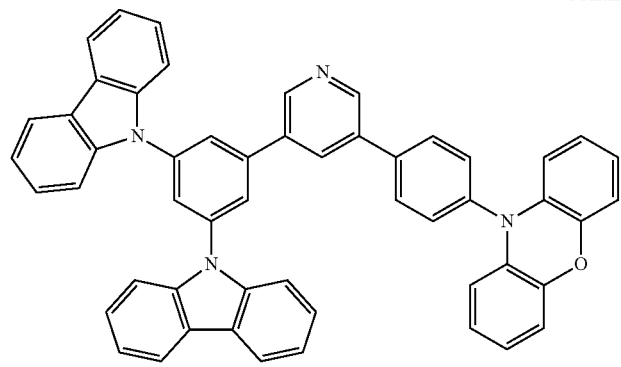
Compound (34)
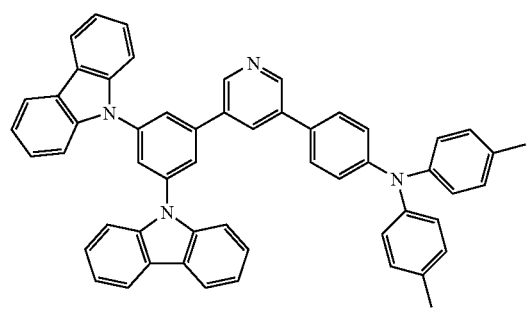
Compound (35)
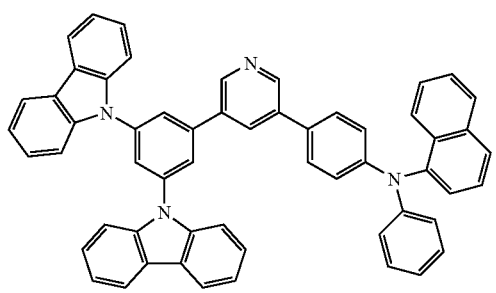
Compound (36)
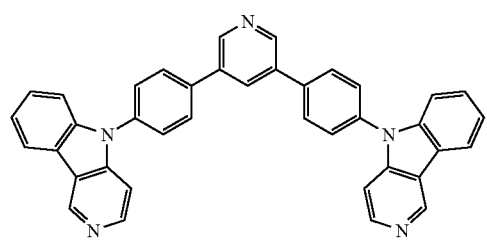
Compound (37)
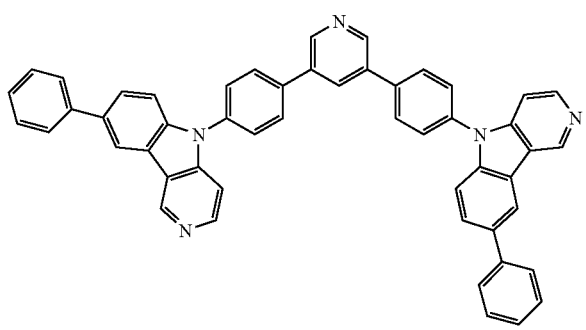
Compound (38)
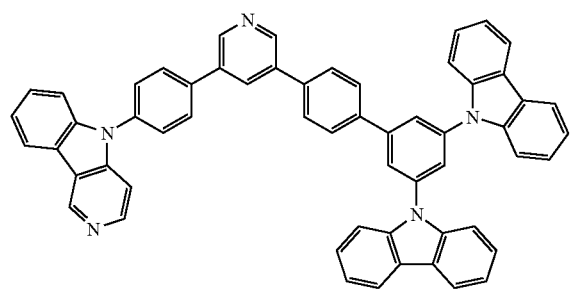
Compound (39)
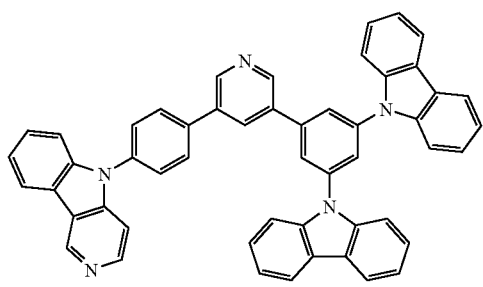

Compound (40)

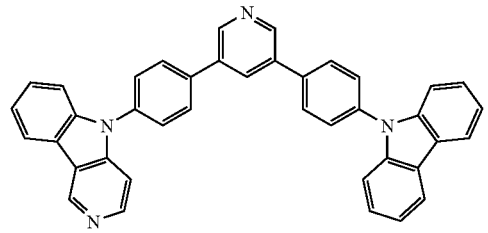

Compound (41)

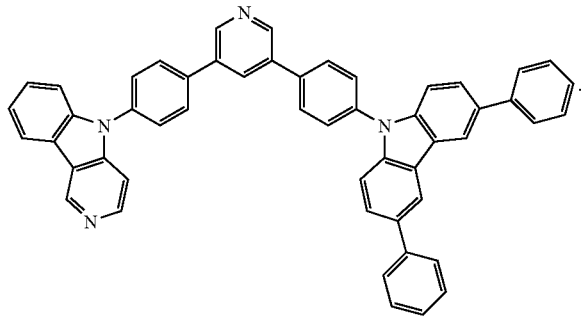

The compound represented by Formula 1 may be further represented by the following Formula 3:

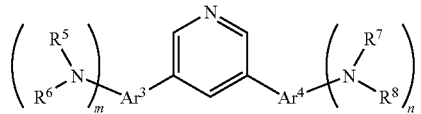

[Formula 3]

In Formula 3: $Ar^3$ and $Ar^4$ may independently be selected from the group consisting of a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene; $R^5$ to $R^8$ may be independently selected from the group consisting of a substituted or unsubstituted C6 to C30 aryl, a substituted or unsubstituted C6 to C30 arylene, a substituted or unsubstituted C2 to C30 heteroaryl, a substituted or unsubstituted C2 to C30 heteroarylene, a substituted or unsubstituted C1 to C30 alkyl, and a substituted or unsubstituted C1 to C30 alkylene, or $R^5$ and $R^6$ form a cyclic ring or $R^7$ and $R^8$ form a cyclic ring; and m and n may independently be integers ranging from 0 to 3, and m+n may be more than or equal to 1.

The compound represented by Formula 1 may be further represented by the following Formula 4:

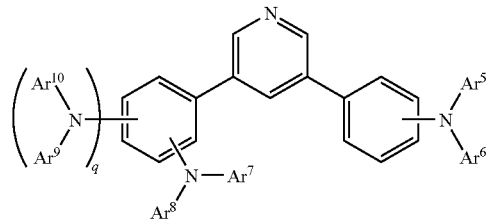

[Formula 4]

In Formula 4: $Ar^5$ to $Ar^{10}$ may independently be selected from the group consisting of a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene, or $Ar^5$ and $Ar^6$ form a cyclic ring, $Ar^7$ and $Ar^8$ form a cyclic ring, or $Ar^9$ and $Ar^{10}$ form a cyclic ring; and q may be an integer ranging from 0 to 2.

The compound represented by Formula 1 may be further represented by the following Formula 5:

[Formula 5]

In Formula 5: $Ar^{11}$ to $Ar^{15}$ may independently be selected from the group consisting of a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene, or $Ar^{12}$ and $Ar^{13}$ form a cyclic ring, or $Ar^{14}$ and $Ar^{15}$ form a cyclic ring; and r may be an integer ranging from 0 to 2.

The compound represented by Formula 5 may be a compound of the following Compounds (42) to (52), and combinations thereof:

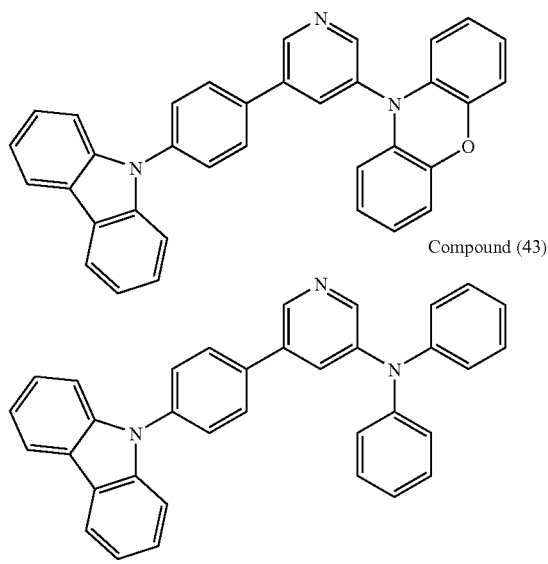

Compound (42)

Compound (43)

Compound (44)
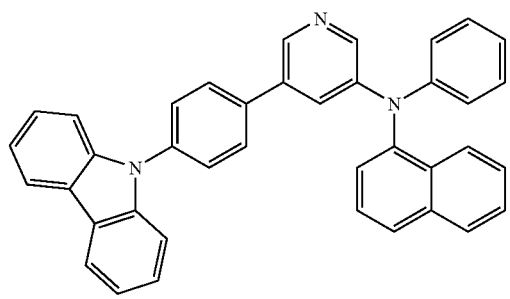
Compound (45)
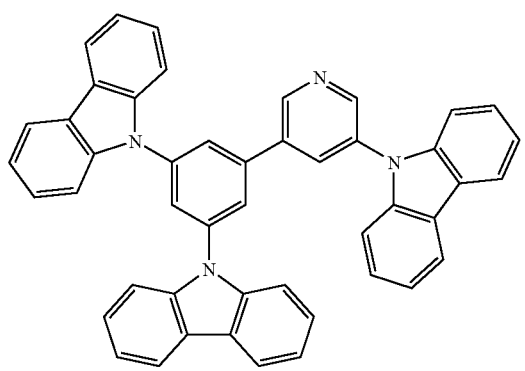
Compound (46)
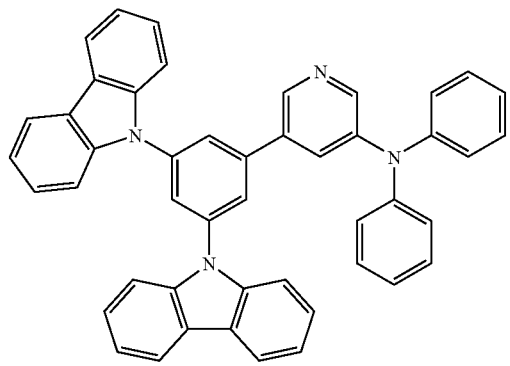
Compound (47)
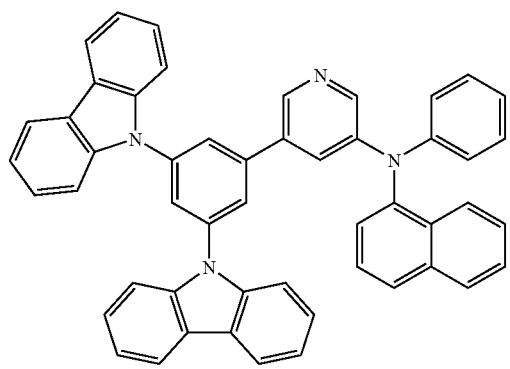
Compound (48)
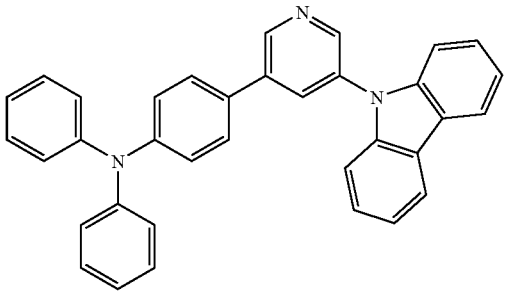
Compound (49)
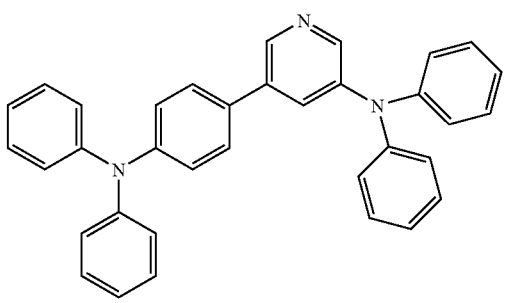
Compound (50)
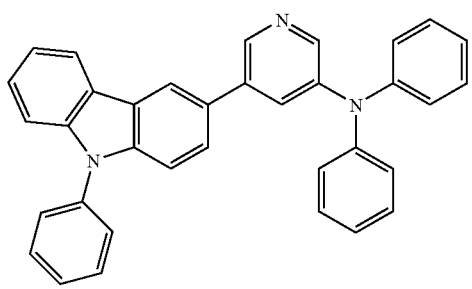
Compound (51)
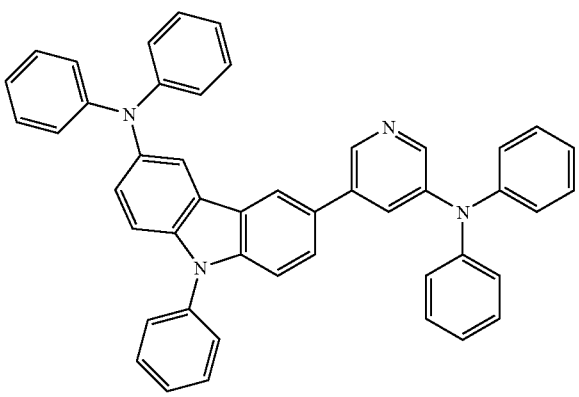

-continued

Compound (52)

The material may further include a dopant. The compound represented by Formula 1 may be a host, and the dopant may be a phosphorescent dopant selected from the group consisting of red, green, blue, and white phosphorescent dopants, and combinations thereof.

The material may further include a dopant. The compound represented by Formula 1 may be a host, and the dopant may be a fluorescent dopant selected from the group consisting of red, green, blue, and white phosphorescent dopants, and combinations thereof.

At least one of the above and other features and advantages may also be realized by providing an organic photoelectric device, including an anode, a cathode, and an organic thin layer disposed between the anode and cathode. The organic thin layer may include a material according to an embodiment.

The organic thin layer may include an emission layer, and at least one layer selected from the group consisting of a hole transport layer (HTL), a hole injection layer (HIL), an electron transport layer (ETL), an electron injection layer (EIL), and combinations thereof.

BRIEF DESCRIPTION OF THE DRAWINGS

The above and other features and advantages will become more apparent to those of skill in the art by describing in detail example embodiments thereof with reference to the attached drawings, in which:

FIGS. 9A through 9K illustrate Compounds (1) through (41);

FIGS. 14 through 19 respectively illustrate Reaction Schemes 1 through 6.

DETAILED DESCRIPTION OF THE INVENTION

Figure 1:
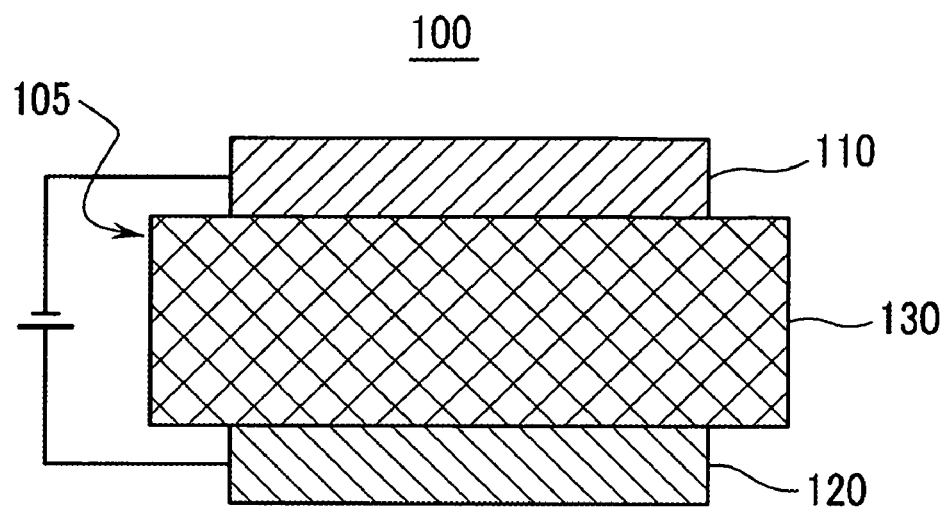
FIGS. 1 to 5 illustrate cross-sectional views of organic photoelectric devices including organic compounds according to various embodiments.

Korean Patent Application No. 10-2007-0036407, filed on Apr. 13, 2007, in the Korean Intellectual Property Office, and entitled: "Material For Organic Photoelectric Device Including Electron Transporting Unit and Hole Transporting Unit, and Organic Photoelectric Device Including the Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, the terms "a" and "an" are open terms that may be used in conjunction with singular items or with plural items.

As used herein, the expressions "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" includes the following meanings: A alone; B alone; C alone; both A and B together; both A and C together; both B and C together; and all three of A, B, and C together. Further, these expressions are open-ended, unless expressly designated to the contrary.

As used herein, the expression "or" is not an "exclusive or" unless it is used in conjunction with the term "either." For example, the expression "A, B, or C" includes A alone; B alone; C alone; both A and B together; both A and C together; both B and C together; and all three of A, B, and C together, whereas the expression "either A, B, or C" means one of A alone, B alone, and C alone, and does not mean any of both A and B together; both A and C together; both B and C together; and all three of A, B, and C together.

Hereinafter, embodiments of the present invention will be described in detail.

The material for an organic photoelectric device can provide an organic photoelectric device having high luminous efficiency at a low driving voltage.

The material for an organic photoelectric device according to one embodiment of the present invention includes a compound represented by the following Formula 1. The material is a bipolar organic compound including both a hole transporting unit and an electron transporting unit.

[Chemical Formula 1]

HTU—⟨pyridine⟩—HTU'

In the above Formula 1, the pyridine ($C_6H_5N$) is an electron transporting unit, the HTU and HTU' independently are a hole transporting unit, and the HTU and HTU' are the same or different.

The organic compound of the above Formula 1 is exemplified by the organic compound of the following Formula 2.

[Chemical Formula 2]

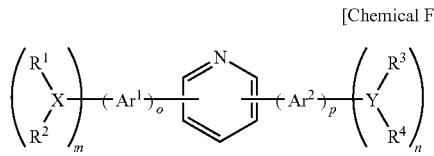

In the above Formula 2, X and Y may independently be nitrogen (N), sulfur (S), or oxygen (O).

$Ar^1$ and $Ar^2$ may independently include one or more substituents such as a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene.

$R^1$ to $R^4$ may independently include one or more substituents such as a substituted or unsubstituted C6 to C30 aryl, a substituted or unsubstituted C6 to C30 arylene, a substituted or unsubstituted C2 to C30 heteroaryl, a substituted or unsubstituted C2 to C30 heteroarylene, a substituted or unsubstituted C1 to C30 alkyl, and a substituted or unsubstituted C1 to C30 alkylene. Alternately, $R^1$ and $R^2$ may form a cyclic ring, and/or $R^3$ and $R^4$ may form a cyclic ring.

When X is sulfur or oxygen, $R^2$ is a unshared electron pair, and when Y is sulfur or oxygen, $R^4$ is a unshared electron pair.

m and n are independently integers ranging from 0 to 3, m+n is more than or equal to 1, and o and p are integers ranging from 0 to 2.

In the present specification, when specific definition is not provided, the term "substituted" refers to one substituted with at least a substituent selected from the group consisting of a halogen, a cyano, a hydroxy, an amino, a C1 to C30 alkyl, a C3 to C30 cycloalkyl, a C6 to C30 aryl, and a C2 to C30 heteroaryl.

In the present specification, when specific definition is not provided, the term "hetero" refers to one including 1 to 3 heteroatoms selected from nitrogen (N), oxygen (O), sulfur (S), phosphorus (P), and Si (silicon) instead of carbon.

In the above Formula 2, when X and Y are nitrogen, and o and p are 1, the organic compound having the above Formula 2 may be represented by the following Formula 3.

[Chemical Formula 3]

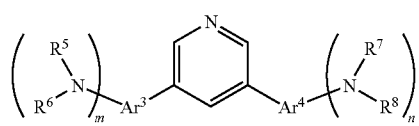

In the above Formula 3, $Ar^3$ and $Ar^4$ may independently include one or more substituents such as a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene.

$R^5$ to $R^8$ may independently include one or more substituents such as a substituted or unsubstituted C6 to C30 aryl, a substituted or unsubstituted C6 to C30 arylene, a substituted or unsubstituted C2 to C30 heteroaryl, a substituted or unsubstituted C2 to C30 heteroarylene, a substituted or unsubstituted C1 to C30 alkyl, and a substituted or unsubstituted C1 to C30 alkylene. Alternately, $R^5$ and $R^6$ form a cyclic ring or $R^7$ and $R^8$ form a cyclic ring.

m and n are independently integers ranging from 0 to 3, and m+n is more than or equal to 1.

In the above Formula 3, when m+n is more than or equal to 2 and $Ar^a$ and $Ar^4$ are phenyl, the organic compound having the above Formula 3 may be represented by the following Formula 4.

[Chemical Formula 4]

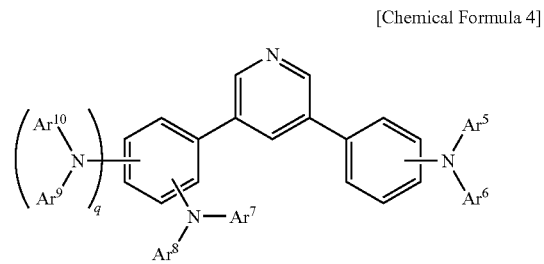

In the above Formula 4, $Ar^5$ to $Ar^{10}$ may independently include one or more substituents such as a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene. Alternately, $Ar^5$ and $Ar^6$ form a cyclic ring, $Ar^7$ and $Ar^8$ form a cyclic ring, or $Ar^9$ and $Ar^{10}$ form a cyclic ring.

q is an integer ranging from 0 to 2.

In the above Formula 3, when m+n is more than or equal to 2, o is 1, and p is 0, the organic compound having the above Formula 3 may be represented by the following Formula 5.

[Chemical Formula 5]

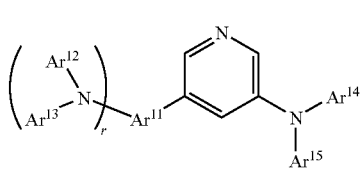

In the above Formula 5, $Ar^{11}$ to $Ar^{15}$ may independently include one or more substituents such as a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene. Alternately, $Ar^{12}$ and $Ar^{13}$ form a cyclic ring, or $Ar^{14}$ and $Ar^{15}$ form a cyclic ring.

r is an integer ranging from 0 to 2.

In the organic compound of the above Formula 2, at least one substituent selected from the group consisting of $XR^1R^2$, $YR^3R^4$, and a combination thereof may be selected from the following Formulae 6a to 6d.

[Chemical Formula 6a]

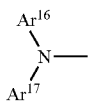

[Chemical Formula 6b]

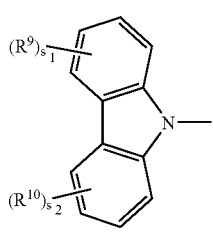

[Chemical Formula 6c]

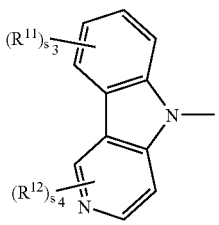

[Chemical Formula 6d]

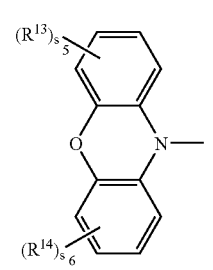

In the above Formulae 6a to 6d, $Ar^{16}$ and $Ar^{17}$ may independently include one or more of, e.g., a substituted or unsubstituted C6 to C30 aryl and a substituted or unsubstituted C2 to C30 heteroaryl.

$R^9$ to $R^{14}$ may independently include one or more substituents such as a substituted or unsubstituted C6 to C30 aryl, a substituted or unsubstituted C2 to C30 heteroaryl, a substituted or unsubstituted C1 to C30 alkyl, a substituted or unsubstituted C2 to C20 alkoxy, and $SiR_{15}R_{16}R_{17}$ (where $R_{15}$ to $R_{17}$ are independently selected from the group consisting of a substituted or unsubstituted C1 to C30 alkyl, a substituted or unsubstituted C1 to C30 aryl, a substituted or unsubstituted C2 to C30 heteroaryl, a substituted or unsubstituted C3 to C30 cycloalkyl, a nitrile, a cyano, a nitro, a carbonyl, and an amide). $s_1$ to $s_6$ are independently integers ranging from 0 to 4.

The organic compounds having the above Formulae 1 to 5 have thermal stability such as a glass transition temperature (Tg) of 120° C. or more, and a thermal decomposition temperature (Td) of 400° C. or more.

The organic compounds having the above Formula 2 may be a Compound of the following compounds (1) to (41), and combinations thereof, but are not limited thereto.

Compound (1)

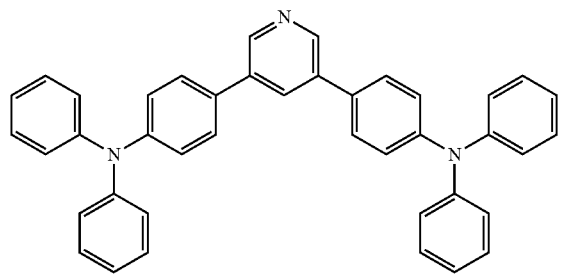

Compound (2)

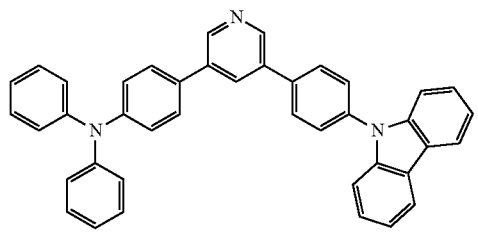

Compound (3)

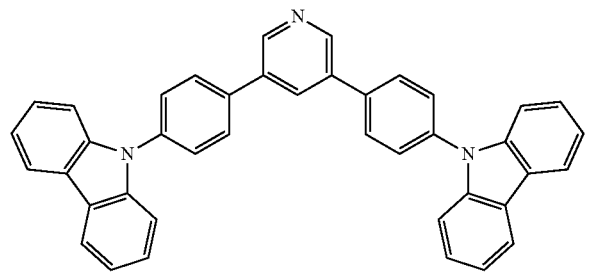

Compound (4)

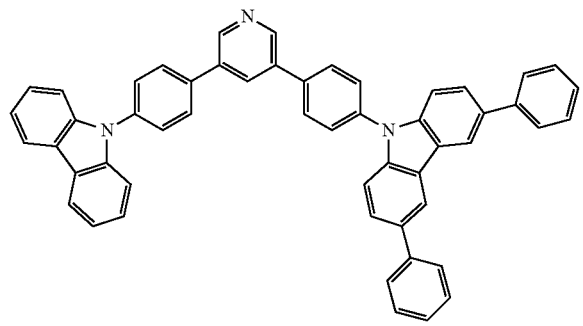

Compound (5)
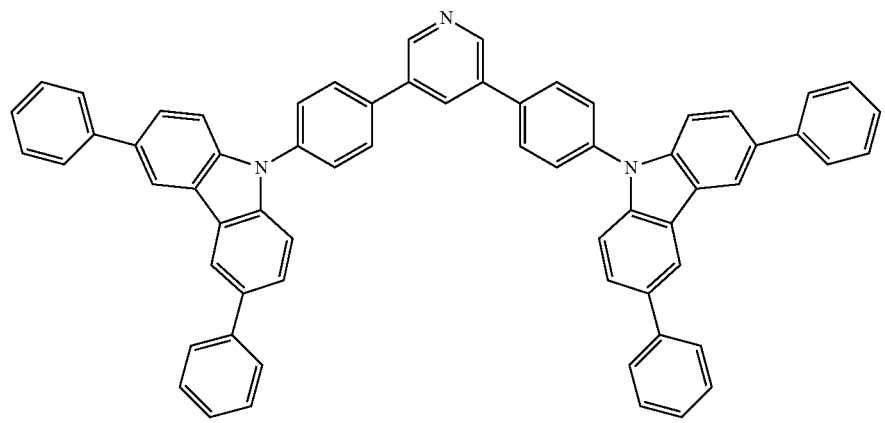
Compound (6) Compound (7)
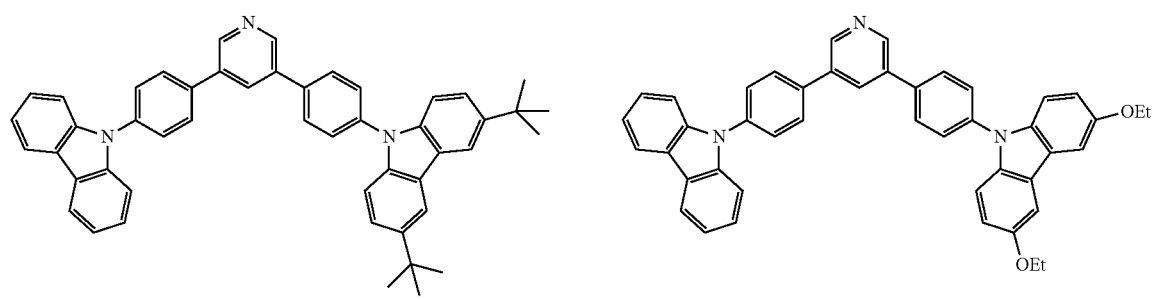
Compound (8) Compound (9)
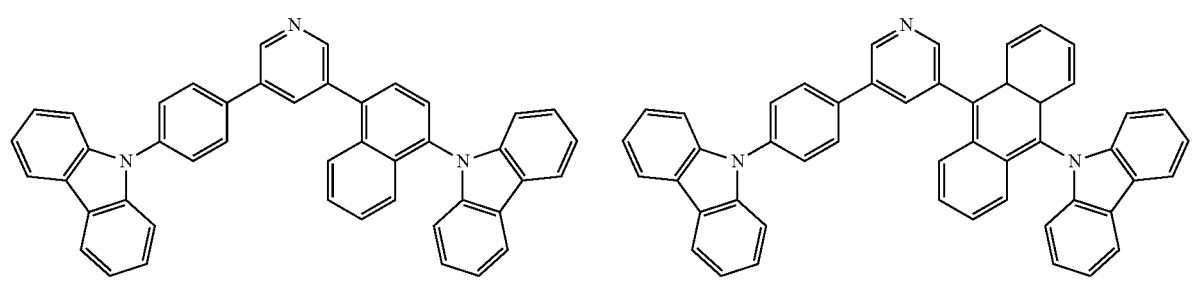
Compound (10) Compound (11)
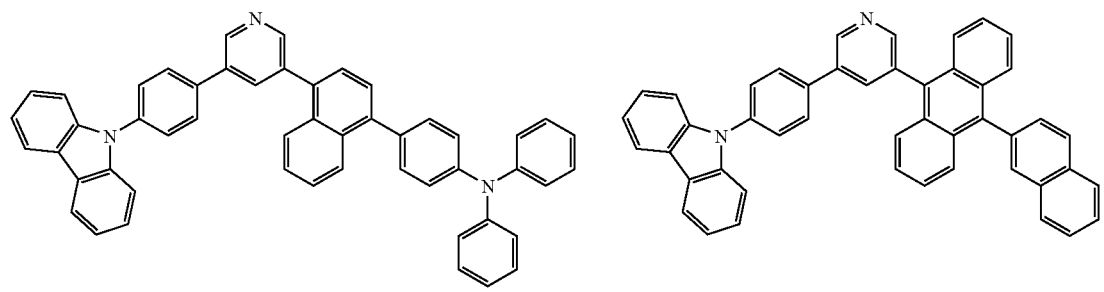

-continued
Compound (12)
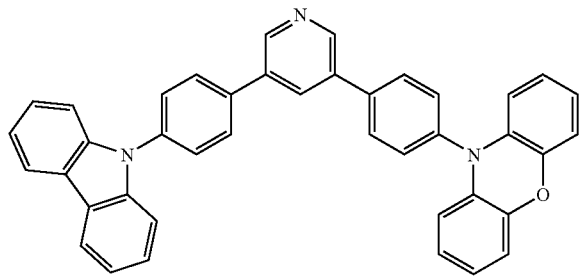
Compound (13)
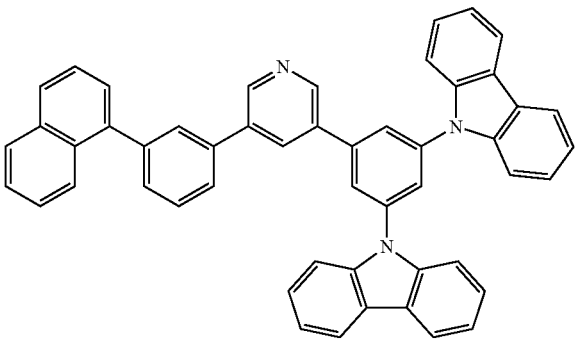
Compound (14)
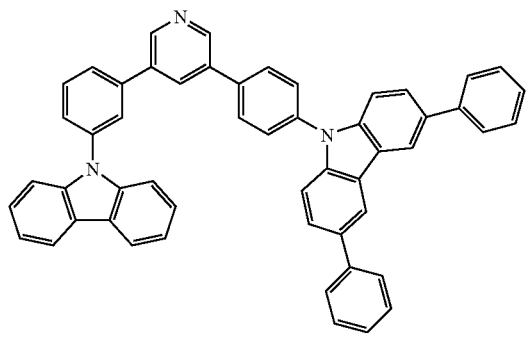
Compound (15)
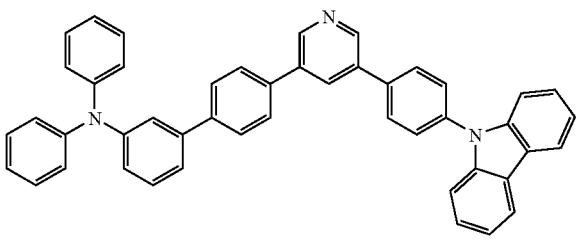
Compound (16)
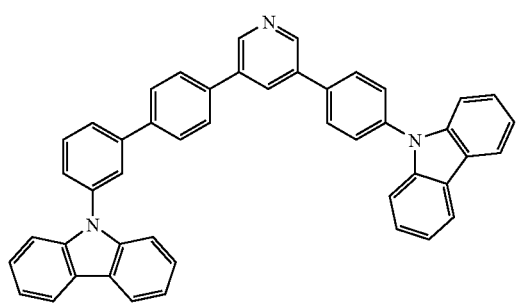
Compound (17)
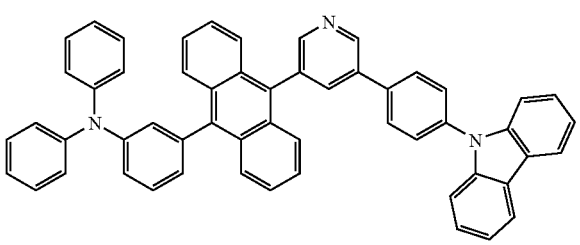
Compound (18)
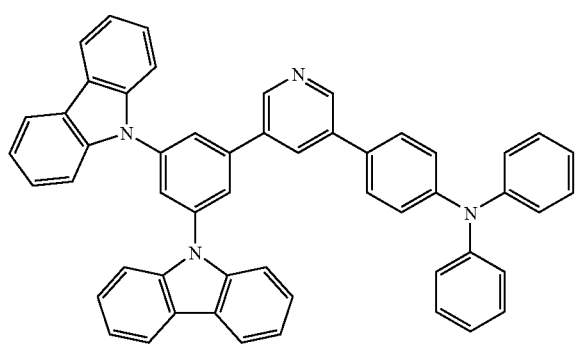
Compound (19)
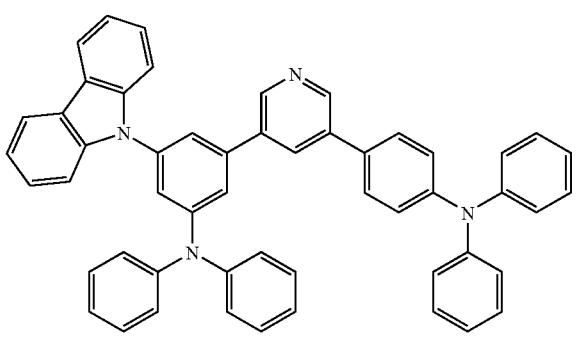

-continued
Compound (20)
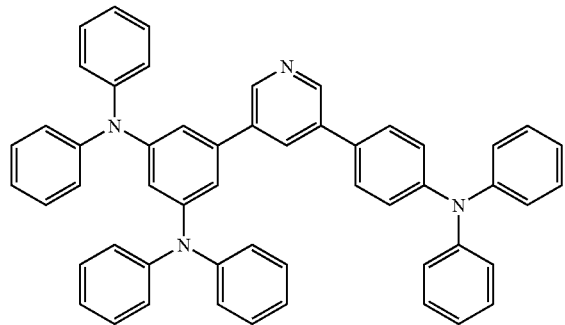
Compound (21)
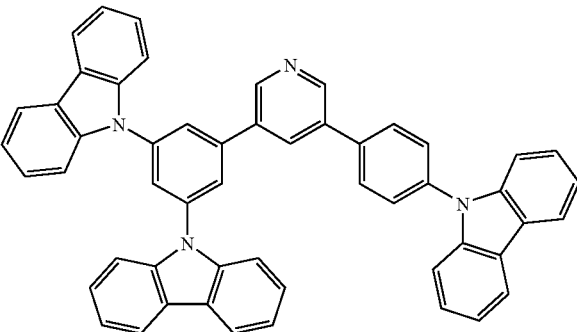
Compound (22)
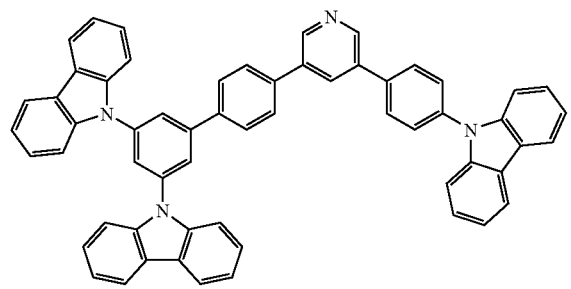
Compound (23)
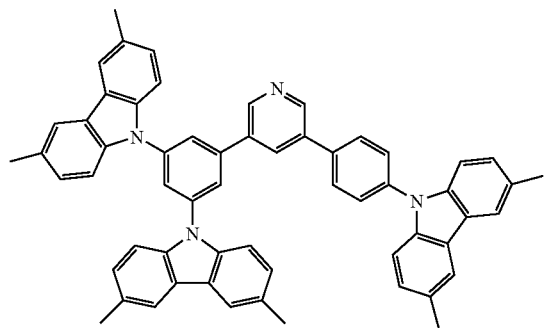
Compound (24)
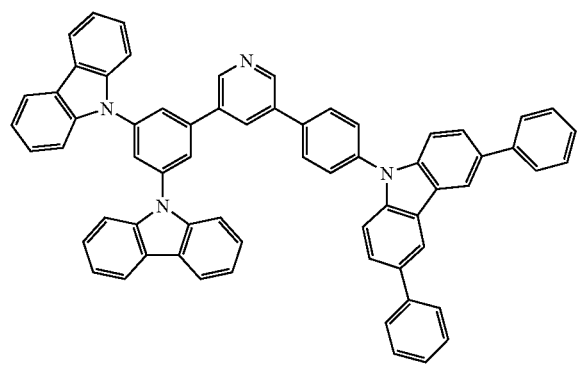
Compound (25)
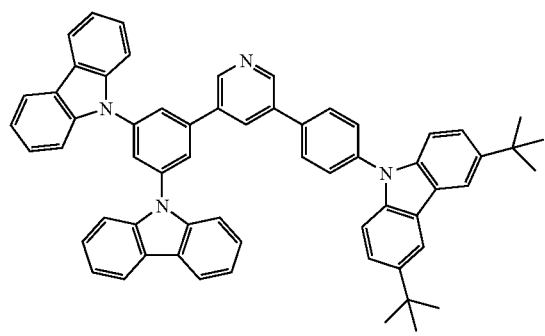
Compound (26)
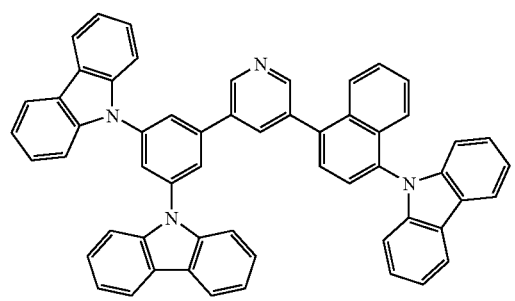
Compound (27)
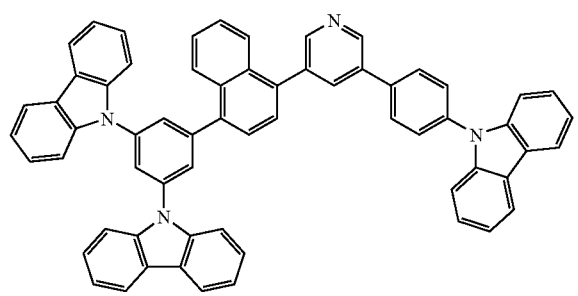

-continued
Compound (28)
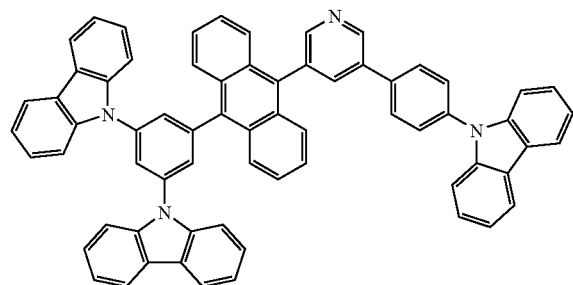
Compound (29)
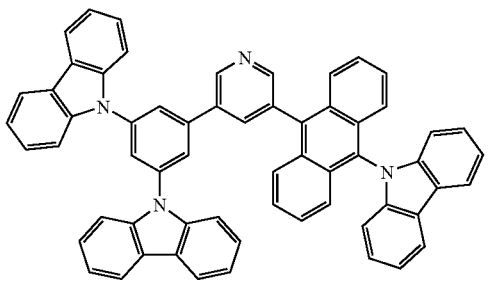
Compound (30)
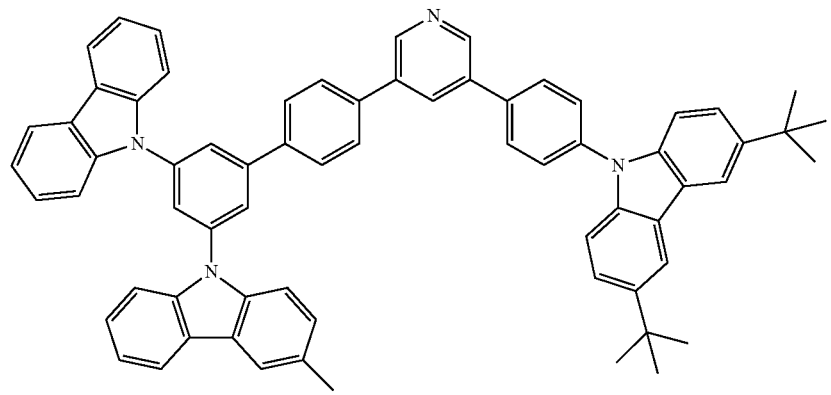
Compound (31)
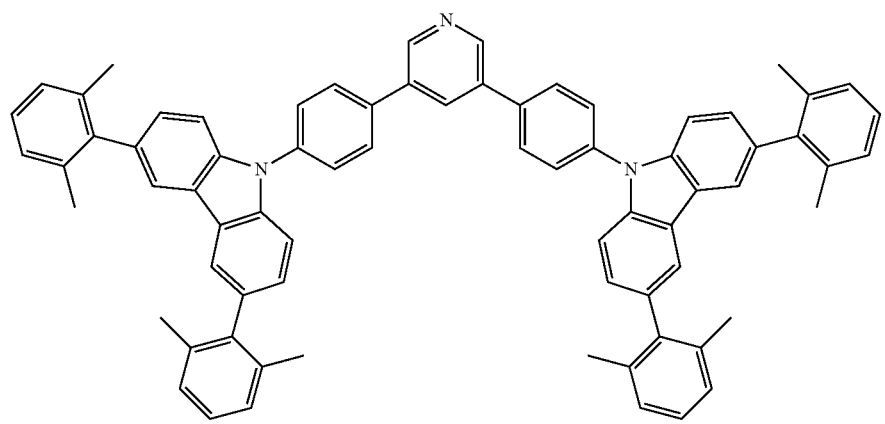
Compound (32)
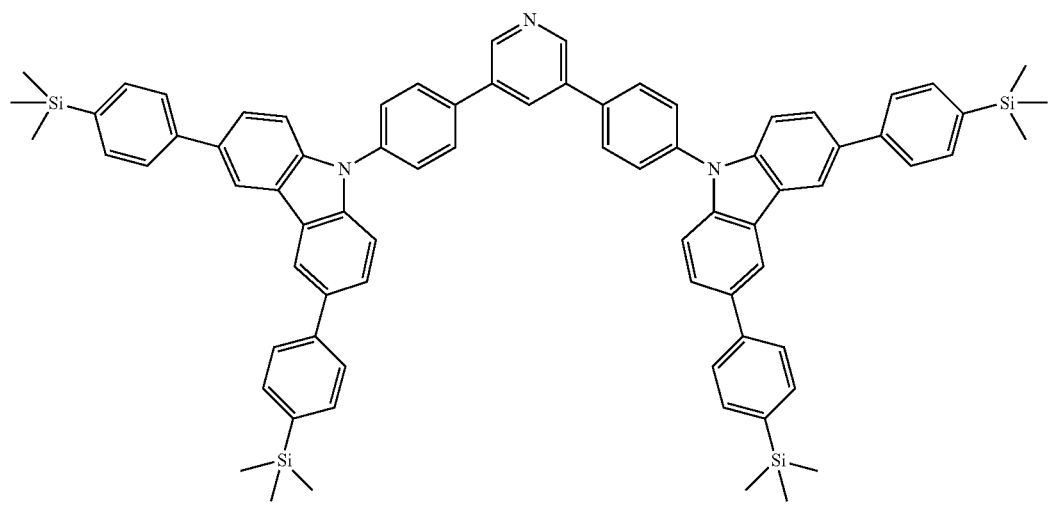

Compound (33)
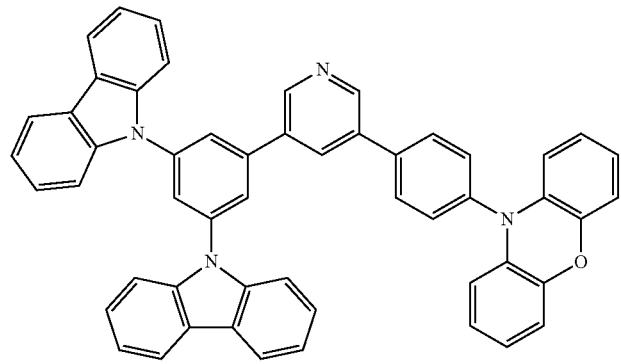
Compound (34)
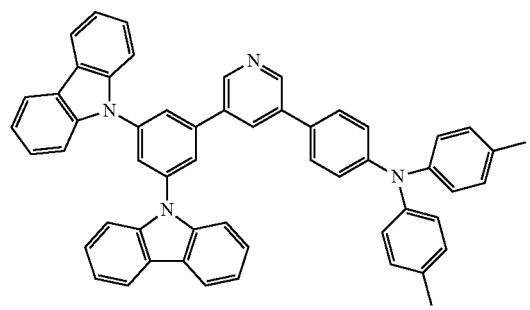
Compound (35)
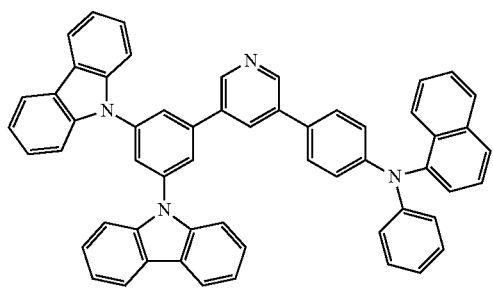
Compound (36)
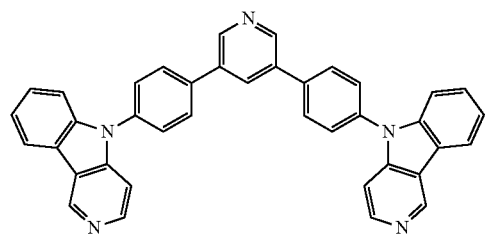
Compound (37)
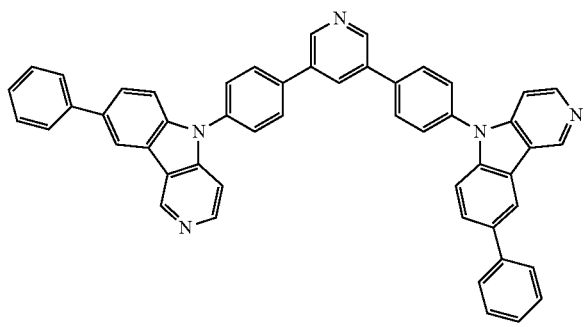
Compound (38)
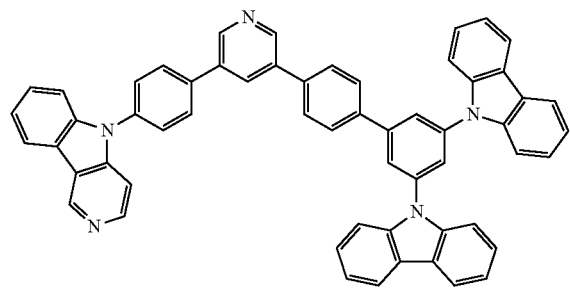
Compound (39)
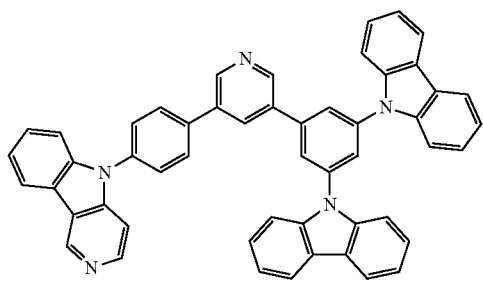

Compound (40)
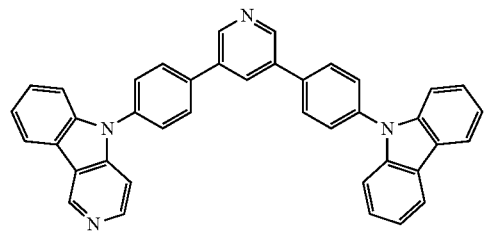
Compound (41)
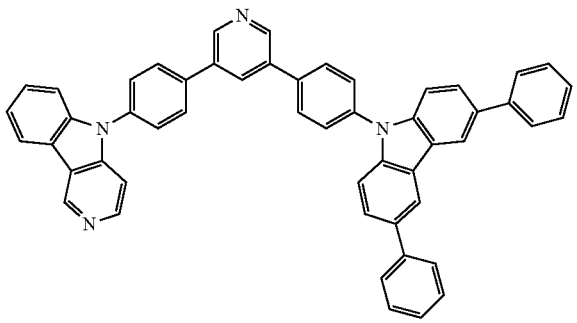
The organic compounds having the above Formula 5 may be a Compound of the following compounds (42) to (52), and combinations thereof, but are not limited thereto.
Compound (42)
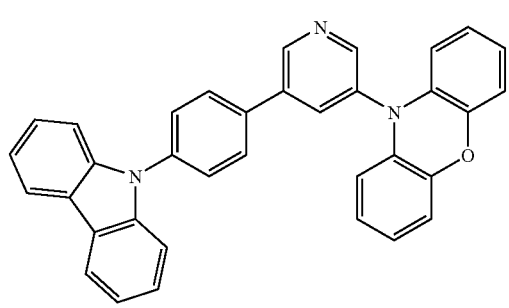
Compound (45)
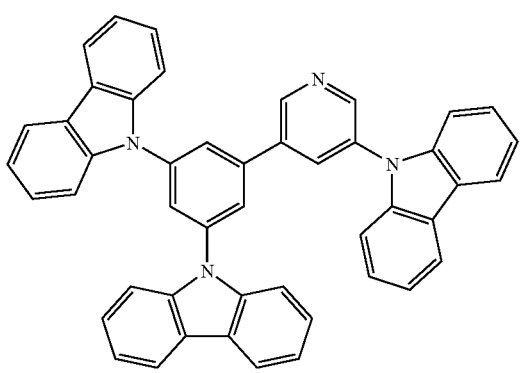
Compound (43)
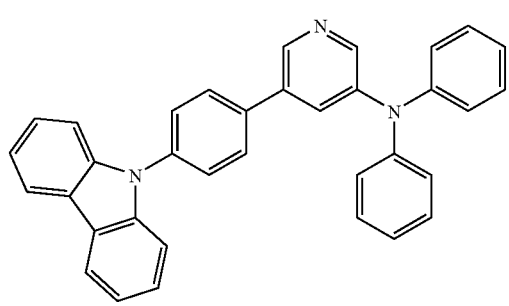
Compound (46)
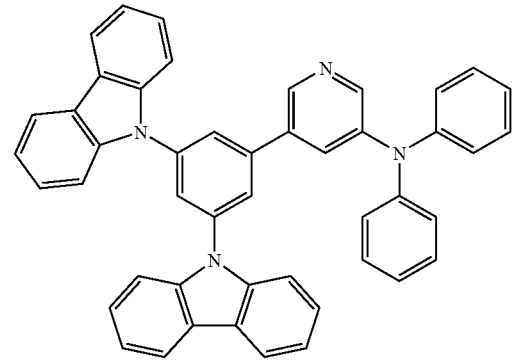
Compound (44)
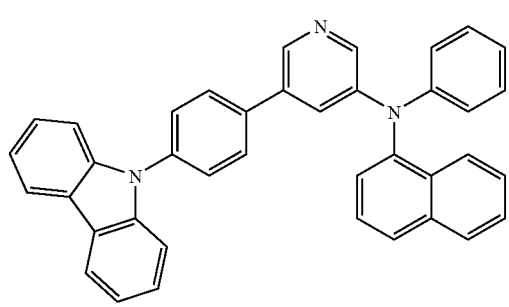
Compound (47)
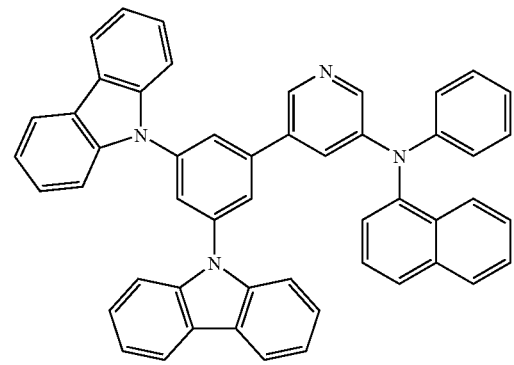

Compound (48)

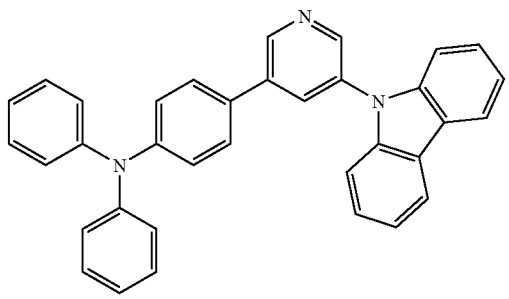

Compound (49)

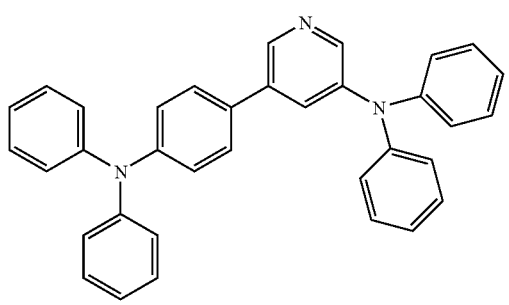

Compound (50)

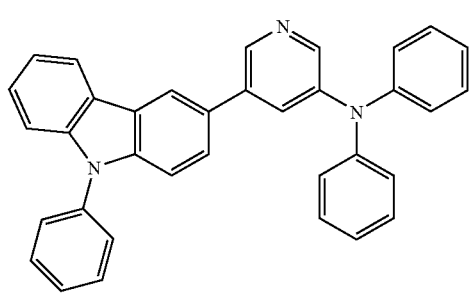

Compound (51)

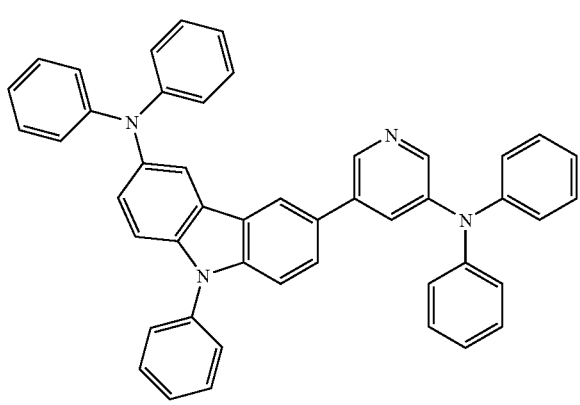

Compound (52)

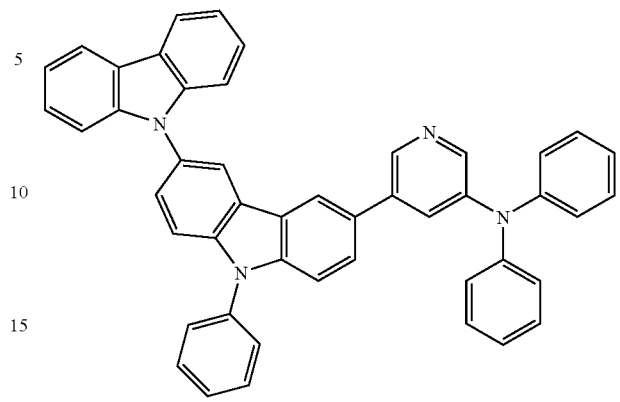

FIGS. 6, 7, 8, 9A through 9L, 10, 11, 12 and 13A through 13C illustrate the above-described Formulae 1-5 and 6a-6d, and Compounds (1)-(52).

The exemplary organic compound, e.g., a compound as represented by Formula 1, may be used by itself, or as a host material that is capable of binding with a dopant.

The dopant is a compound having a high emission property, by itself. However, it is usually added to a host in a minor amount, so it is also called a guest or dopant. In other words, the dopant is a material that is doped to the host material to emit light, and generally includes a metal complex that emits light due to multiplet excitation into a triplet or higher state.

When the organic compounds represented by the above Formulae 1 to 5 are used for a light emitting host material, all red (R), green (G), and blue (B) colors and white (W) fluorescent or phosphorescent dopant materials are available for a dopant. According to one embodiment, the dopant includes a phosphorescent dopant material. Generally, the material should satisfy the requirement to have a high light emitting quantum efficiency, to be rarely agglomerated, and to be distributed uniformly in the host material.

According to one embodiment, the phosphorescent dopant is an organic metal compound including at least element selected from the group consisting of Ir, Pt, Os, Ti, Zr, Hf, Eu, Tb, Tm, and combinations thereof.

Specifically, the red phosphorescent dopant may include PtOEP, Ir(Piq)$_2$(acac) (Piq=1-phenylisoquinoline, acac=pentane-2,4-dione), Ir(Piq)$_3$, and RD 61 from UDC; the green phosphorescent dopant may include Ir(PPy)$_3$ (PPy=2-phenylpyridine), Ir(PPy)$_2$(acac), and GD48 from UDC; and the blue phosphorescent dopant may include (4,6-F$_2$PPy)$_2$Irpic (reference: Appl. Phys. Lett., 79, 2082-2084, 2001).

FIGS. 1 to 5 illustrate cross-sectional views of organic photoelectric devices including the organic compounds according to various embodiments.

An organic photoelectric device according to one embodiment of the present invention includes at least one layer of an organic thin layer interposed between an anode and a cathode. The anode includes a transparent electrode such as ITO (indium tin oxide), and the cathode includes a metal electrode such as aluminum.

Referring to FIG. 1, the organic photoelectric device 100 includes an organic thin layer 105 including only an emission layer 130.

Figure 2:
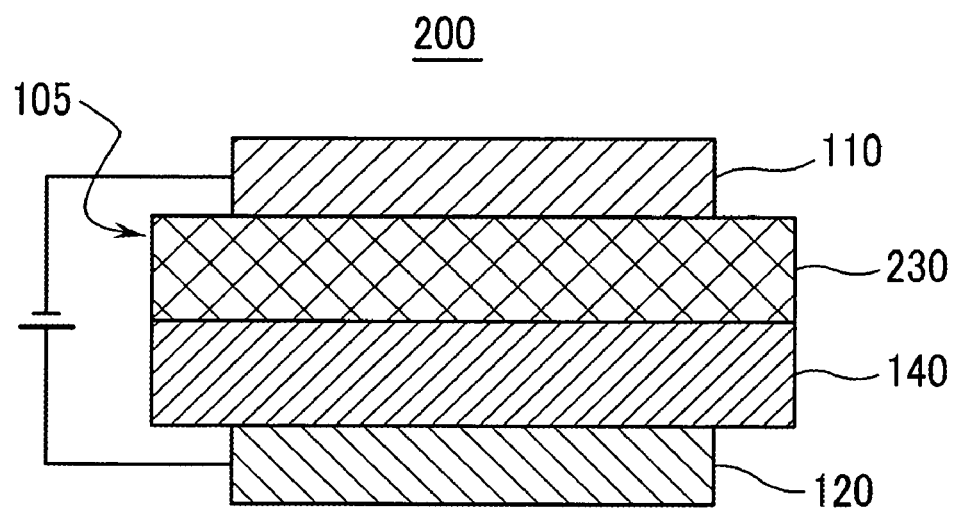

Referring to FIG. 2, a double-layered organic photoelectric device 200 includes an organic thin layer 105 including an emission layer 230 including an electron transport layer (ETL) (not shown), and a hole transport layer (HTL) 140. The hole transport layer (HTL) 140 is a separate layer having an excellent binding property with a transparent electrode such as ITO or a excellent hole transporting property.

Figure 3:
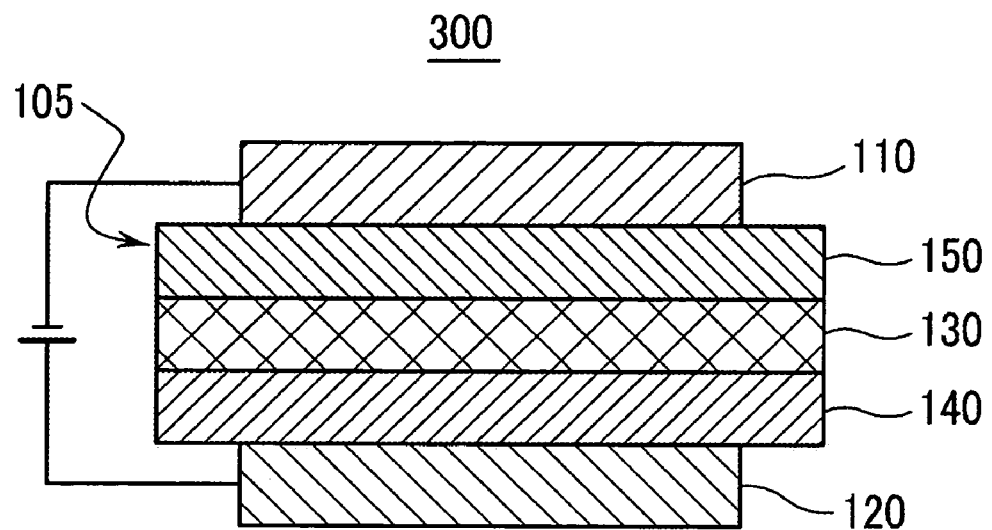

Referring to FIG. 3, a three-layered organic photoelectric device 300 includes the organic thin layer 105 including an electron transport layer (ETL) 150, an emission layer 130, and a hole transport layer (HTL) 140. The emission layer 130 is independently installed, and layers having an excellent electron transporting property or an excellent hole transporting property are separately stacked.

Figure 4:
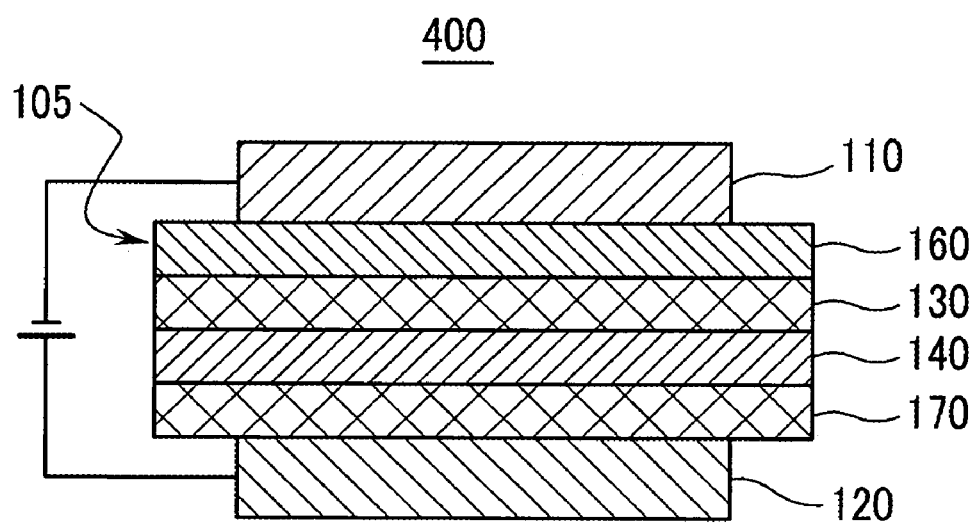

As shown in FIG. 4, a four-layered organic photoelectric device 400 includes the organic thin layer 105 including an electron injection layer (EIL) 160, an emission layer 130, a hole transport layer (HTL) 140, and a hole injection layer (HIL) 170 for binding with the cathode of ITO, different from the structure of the three-layered organic photoelectric device 300 shown in FIG. 3.

Figure 5:
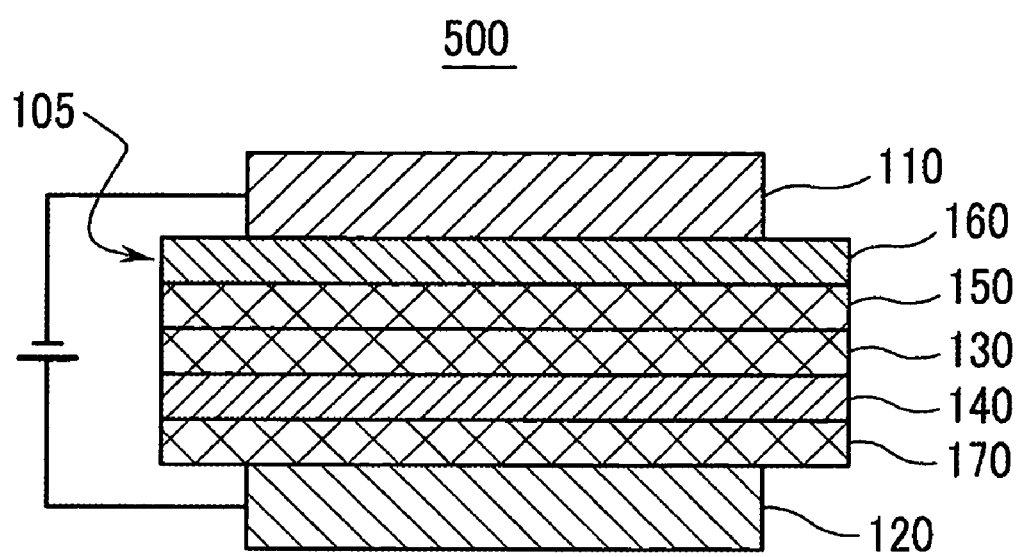
Figure 6:
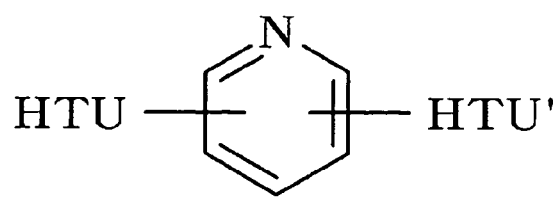
FIG. 6 illustrates Formula 1.
Figure 7:
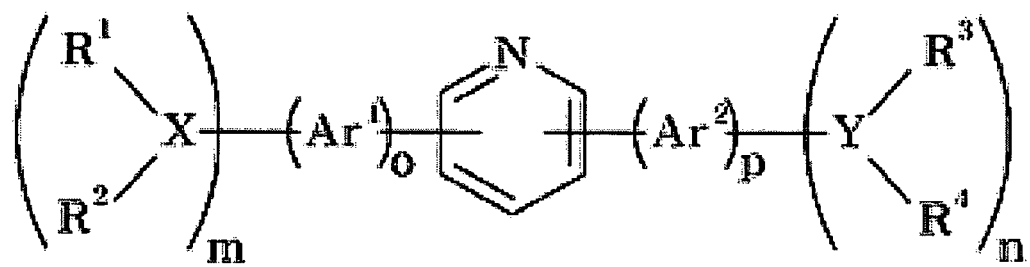
FIG. 7 illustrates Formula 2.
Figure 8:
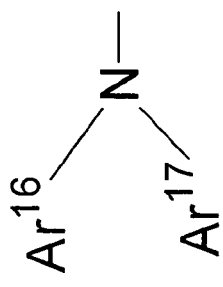
FIG. 8 illustrates Formulae 6a through 6d.
Figure 8:
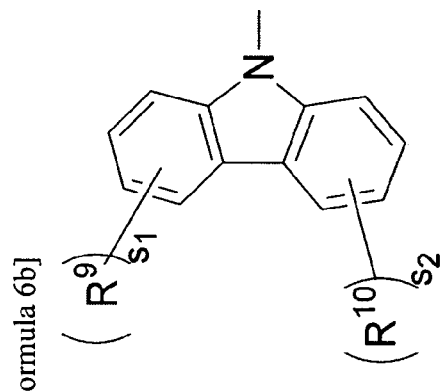
Figure 8:
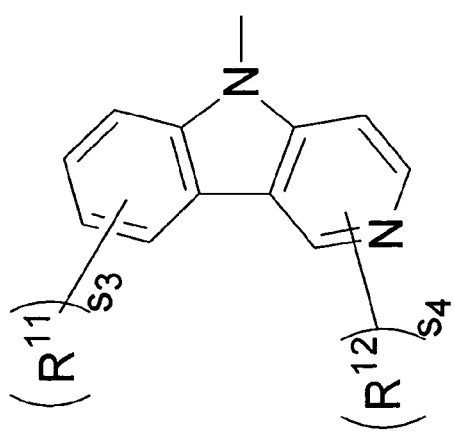
Figure 8:
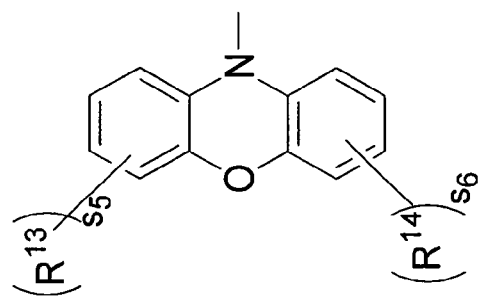
Figure 9A:
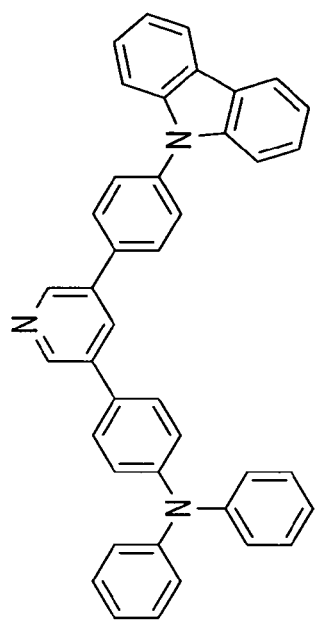
Figure 9A:
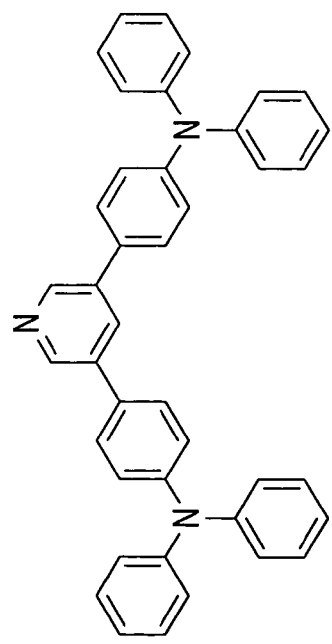
Figure 9A:
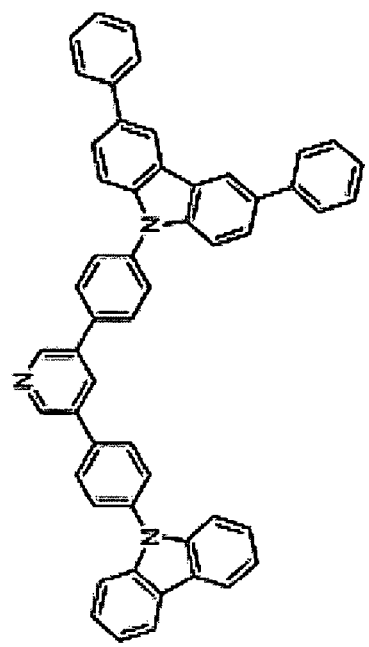
Figure 9A:
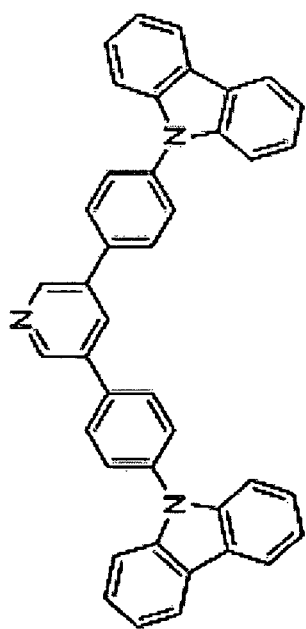
Figure 9B:
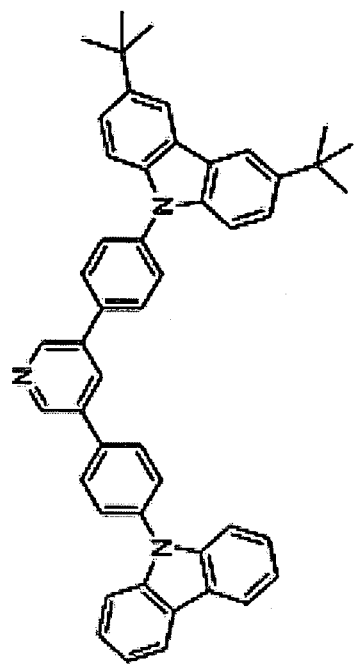
Figure 9B:
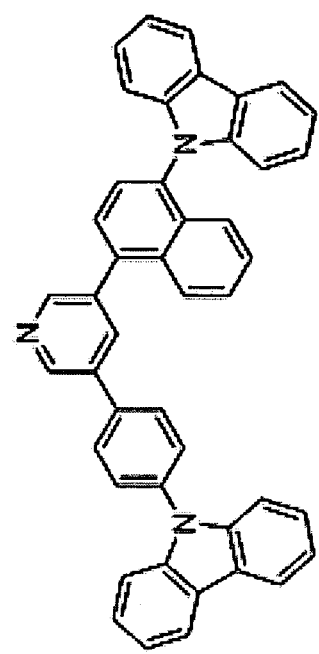
Figure 9B:
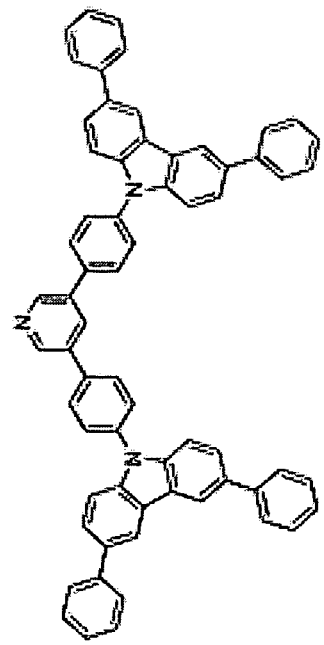
Figure 9B:
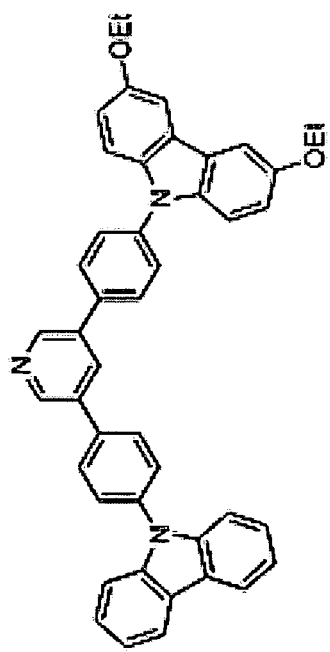
Figure 9C:
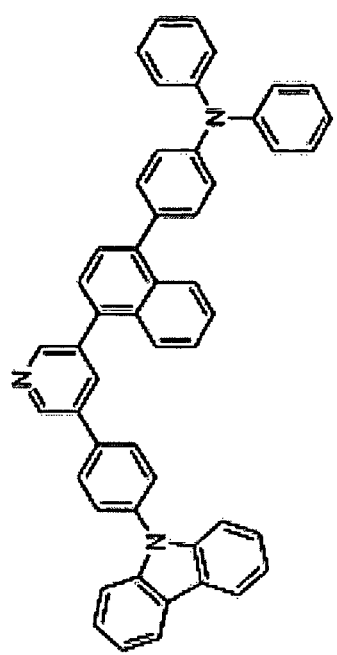
Figure 9C:
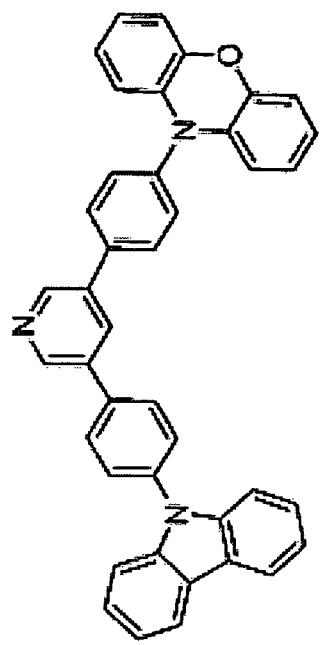
Figure 9C:
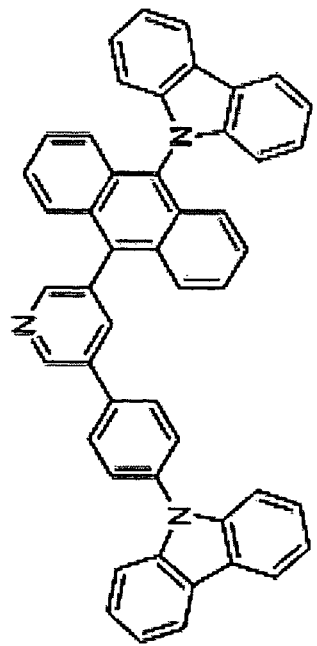
Figure 9C:
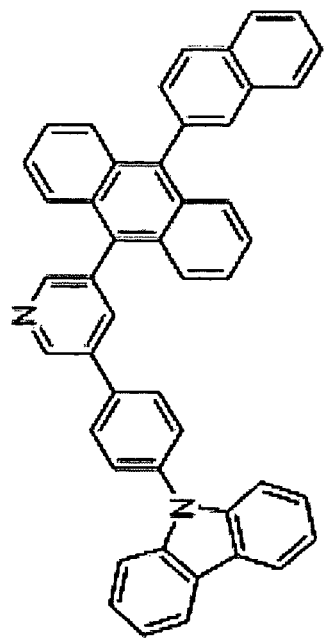
Figure 9D:
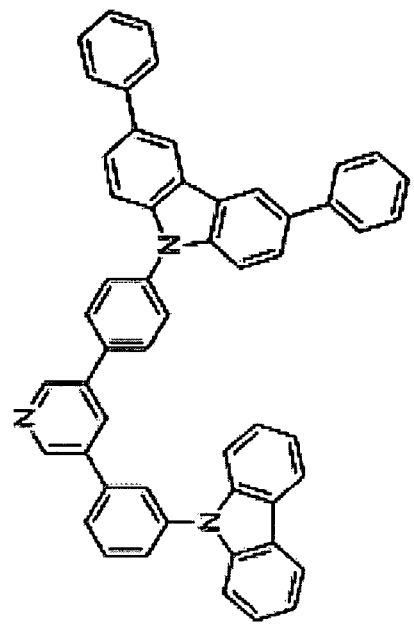
Figure 9D:
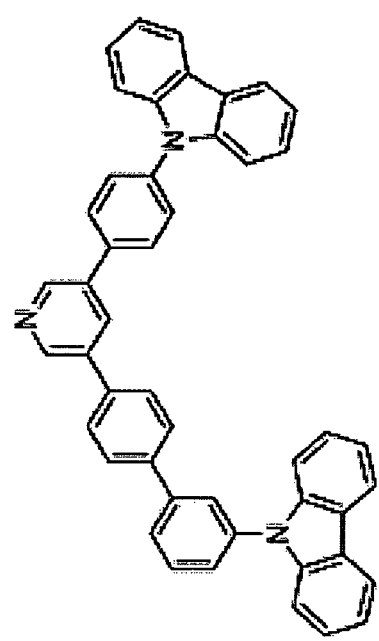
Figure 9D:
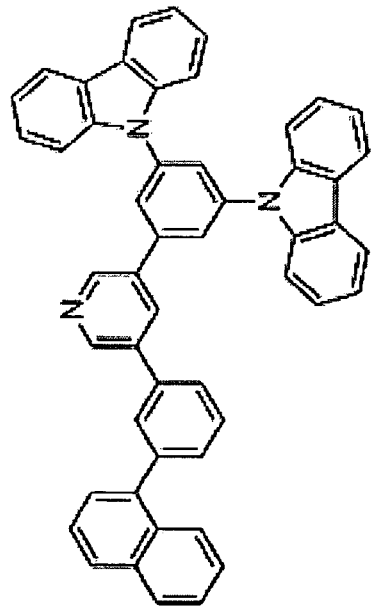
Figure 9D:
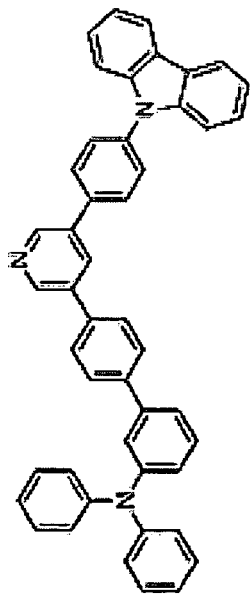
Figure 9E:
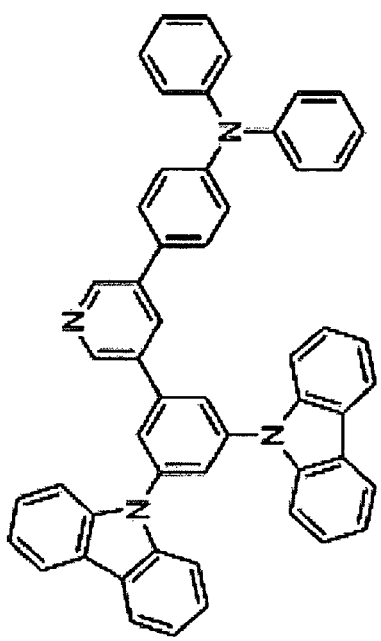
Figure 9E:
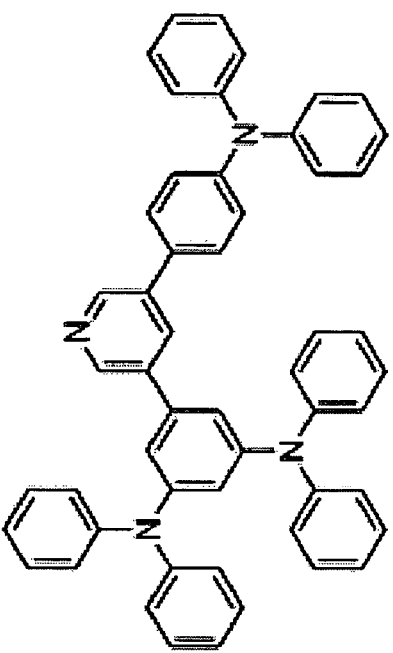
Figure 9E:
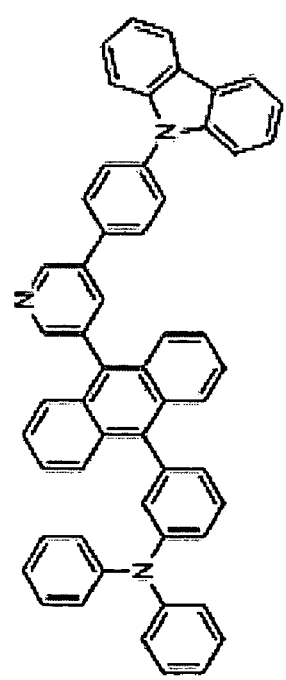
Figure 9E:
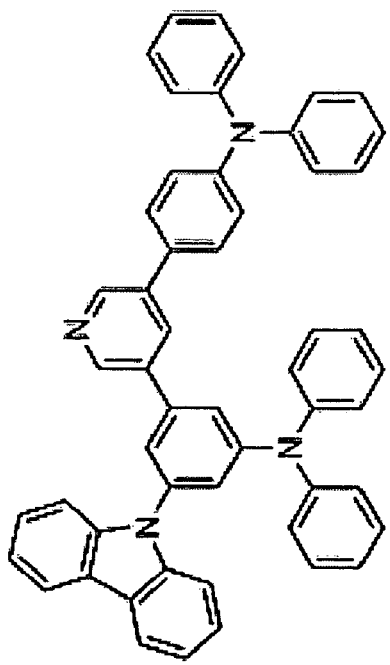
Figure 9F:
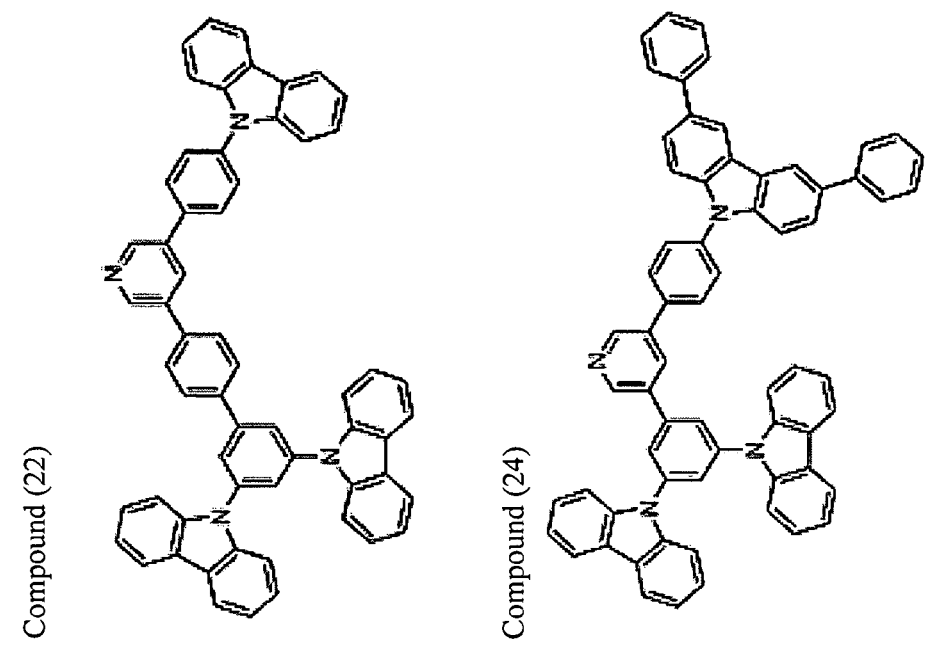
Figure 9F:
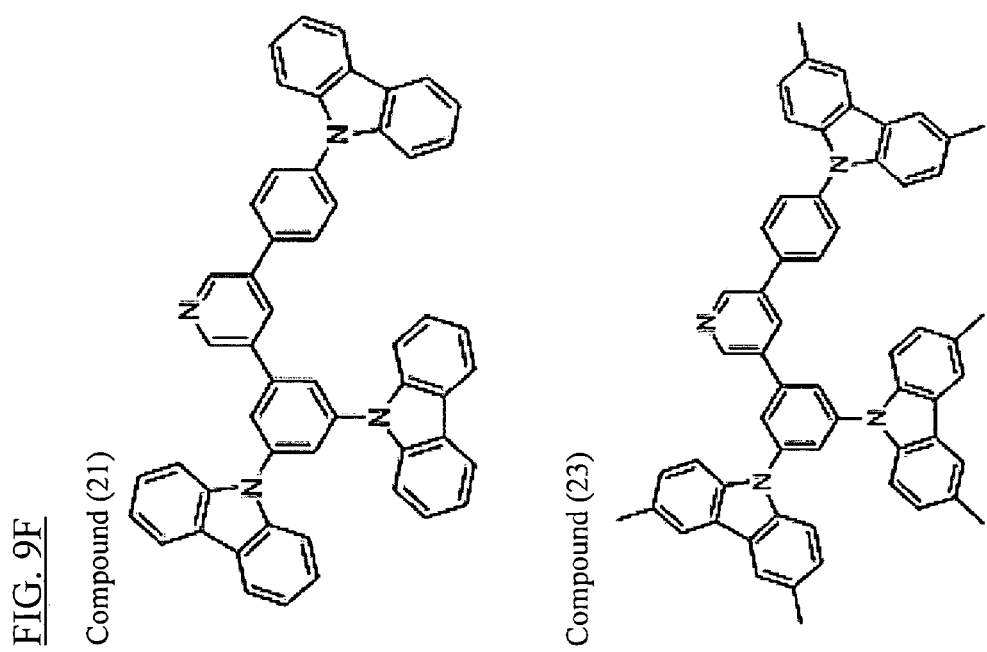
Figure 9G:
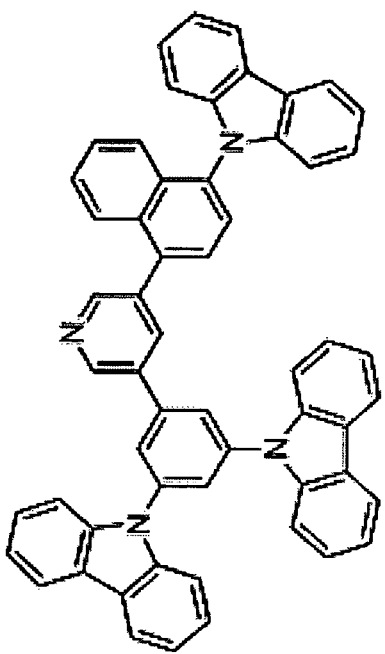
Figure 9G:
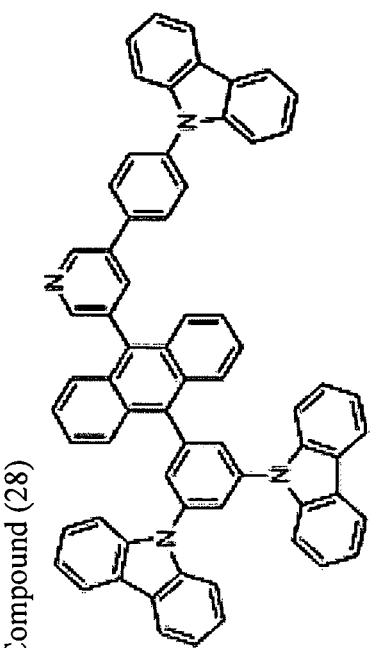
Figure 9G:
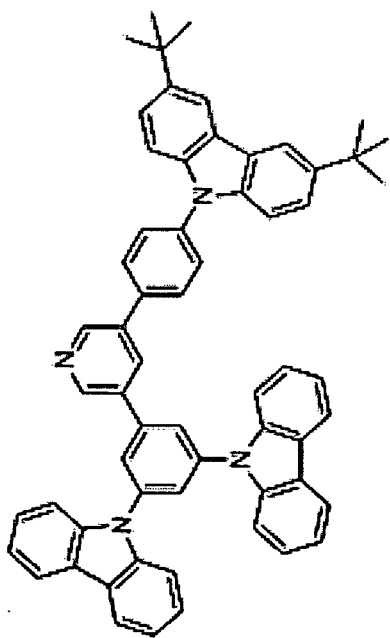
Figure 9G:
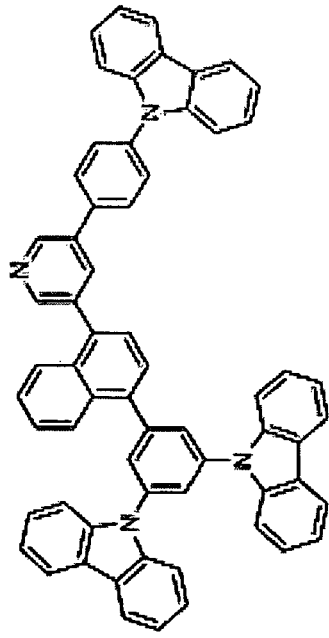
Figure 9H:
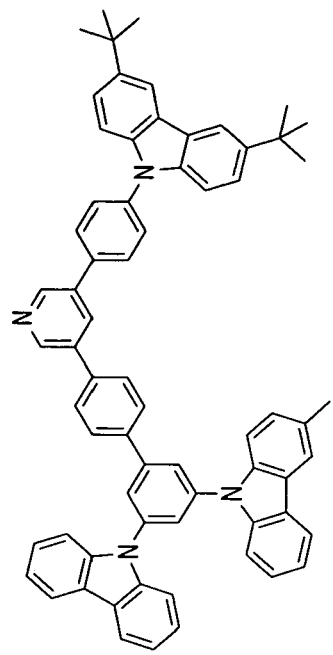
Figure 9H:
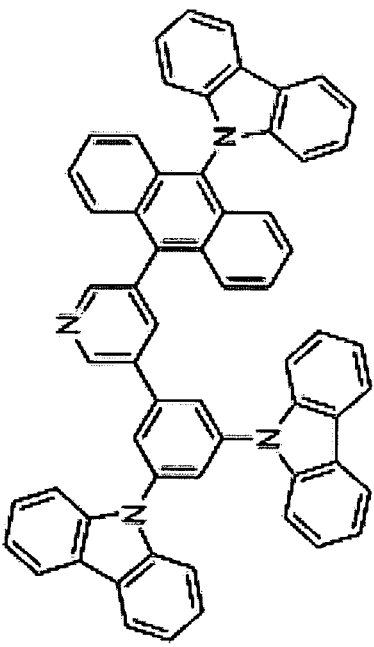
Figure 9H:
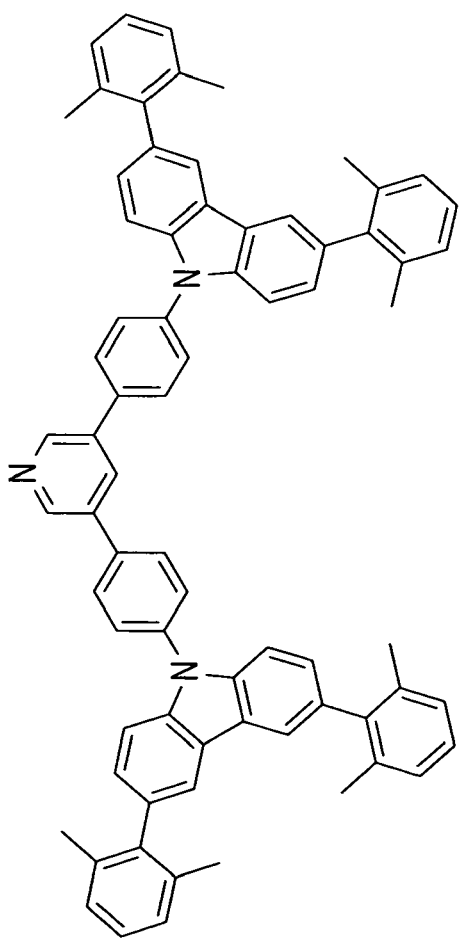
Figure 9I:
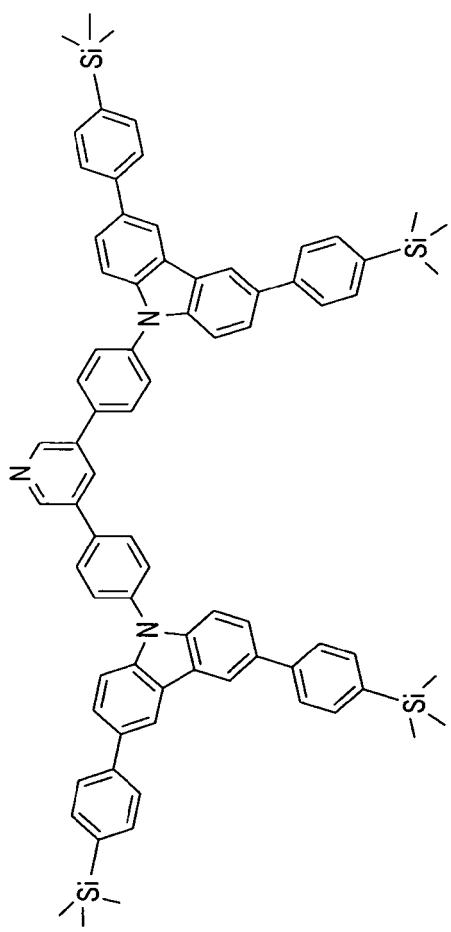
Figure 9I:
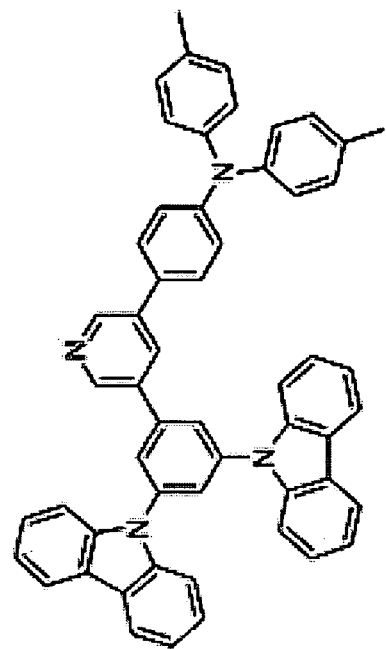
Figure 9I:
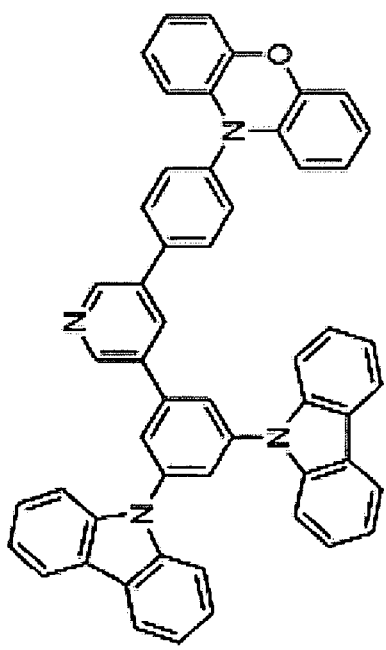
Figure 9J:
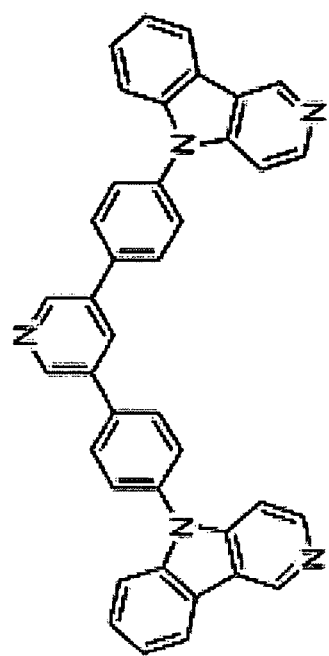
Figure 9J:
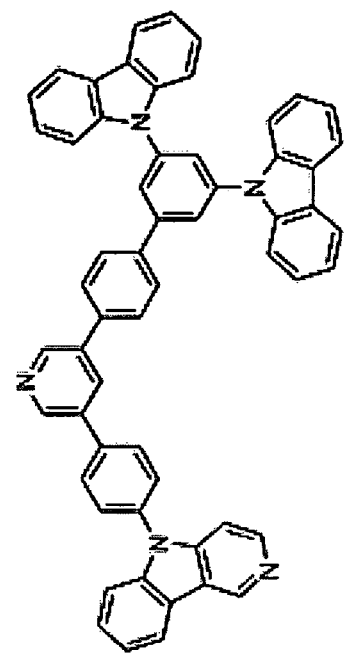
Figure 9J:
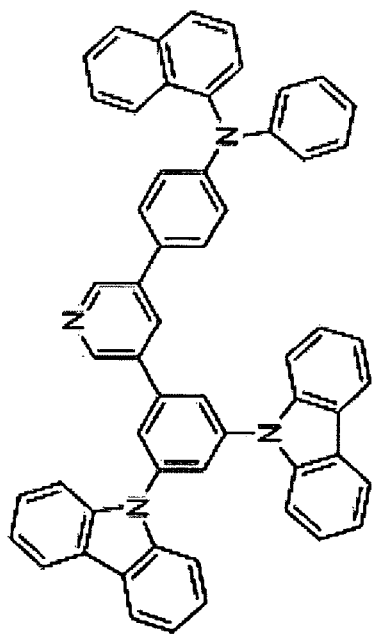
Figure 9J:
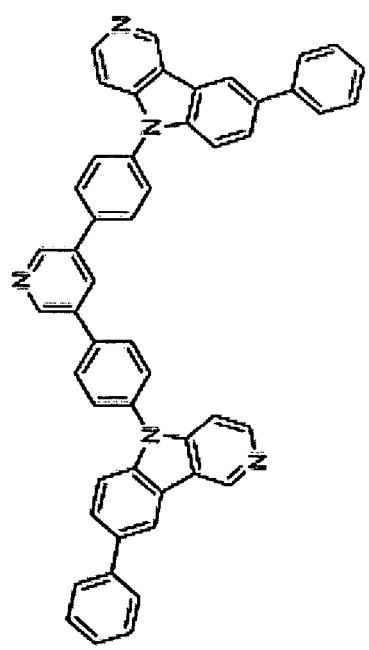
Figure 10:
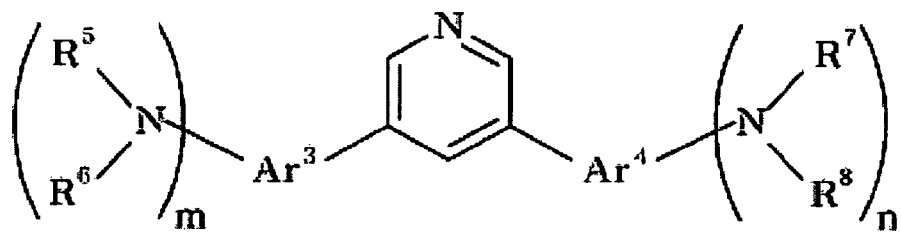
FIG. 10 illustrates Formula 3.
Figure 11:
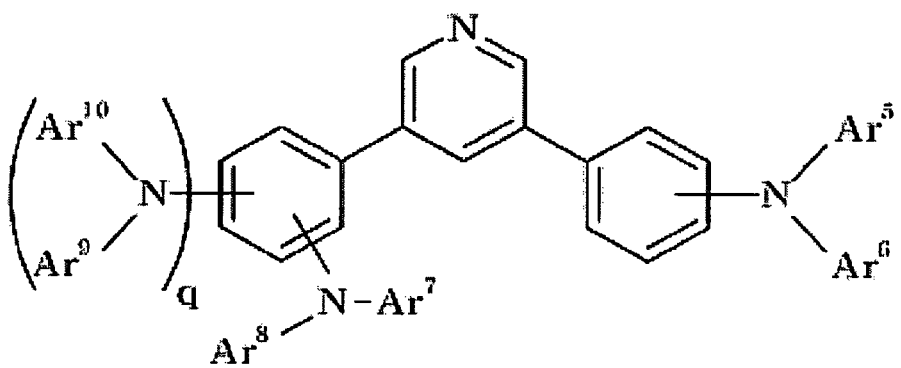
FIG. 11 illustrates Formula 4.
Figure 12:
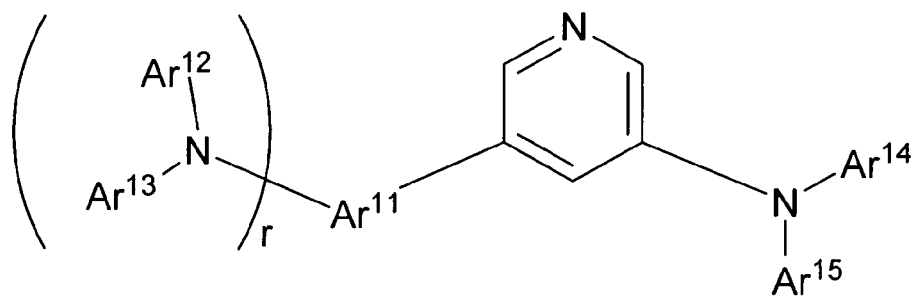
FIG. 12 illustrates Formula 5.
Figure 13A:
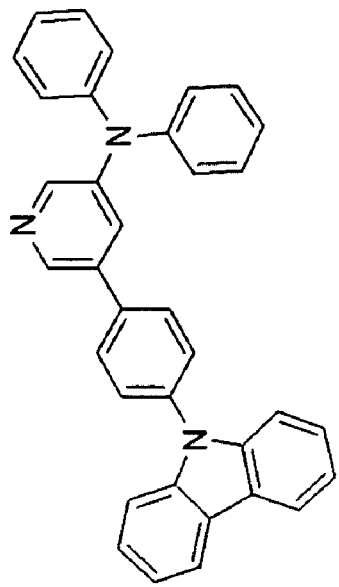
FIGS. 13A through 13C illustrate Compounds (42) through (52)
Figure 13A:
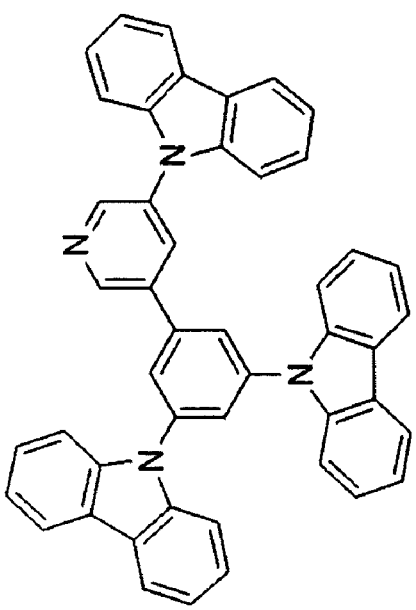
Figure 13A:
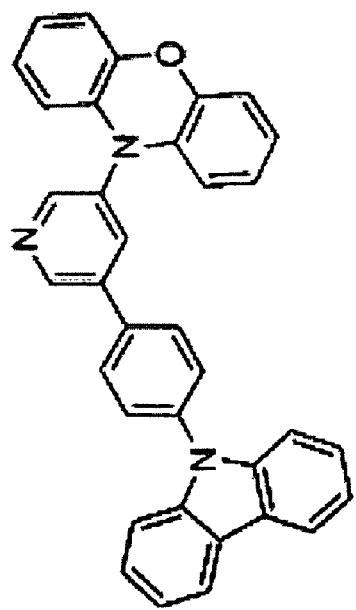
Figure 13A:
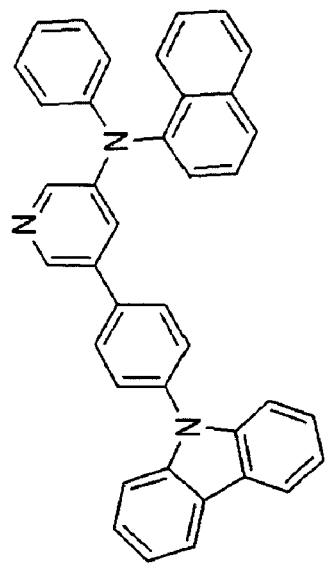
Figure 13B:
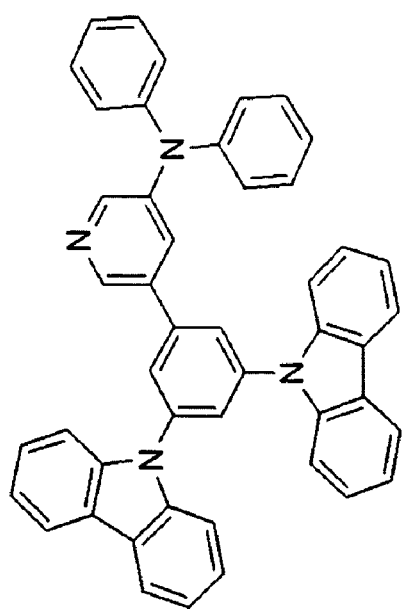
Figure 13B:
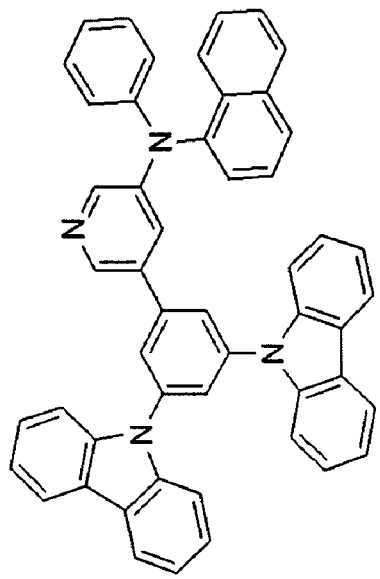
Figure 13B:
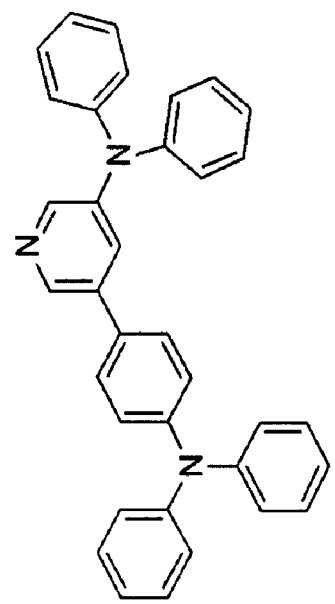
Figure 13B:
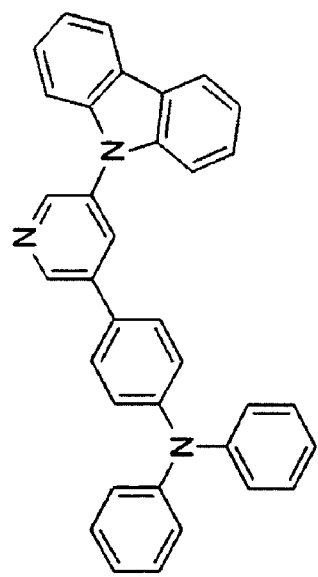
Figure 13C:
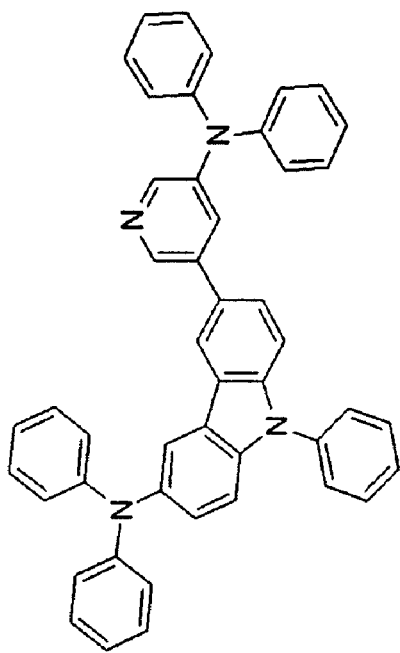
Figure 13C:
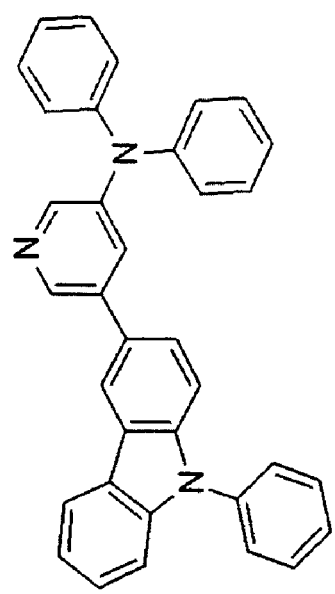
Figure 13C:
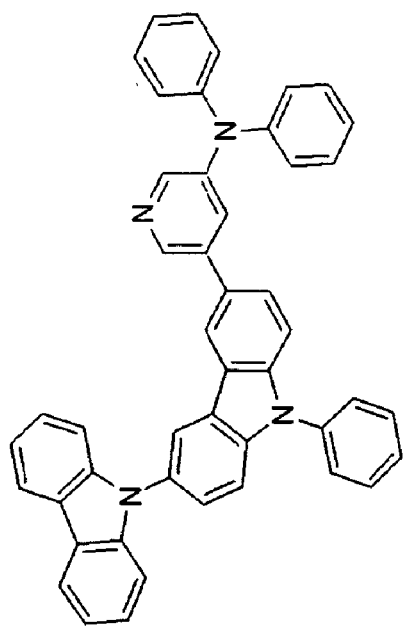
Figure 14:
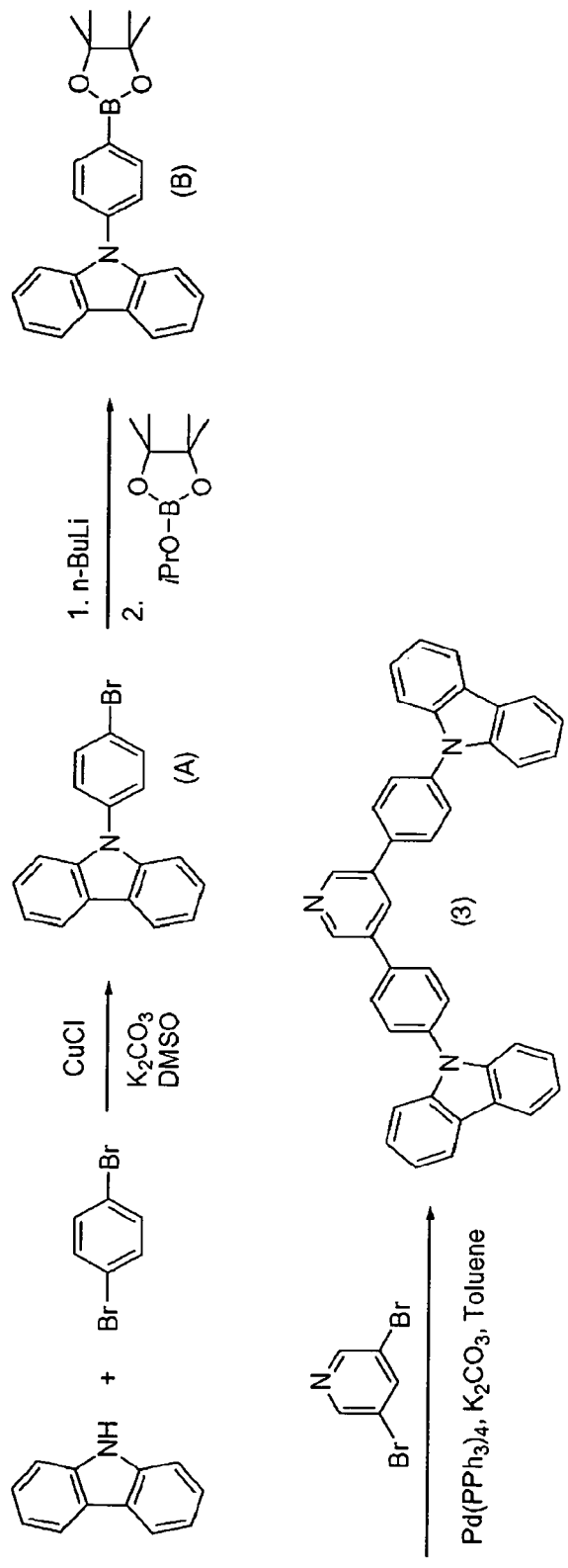
Figure 15:
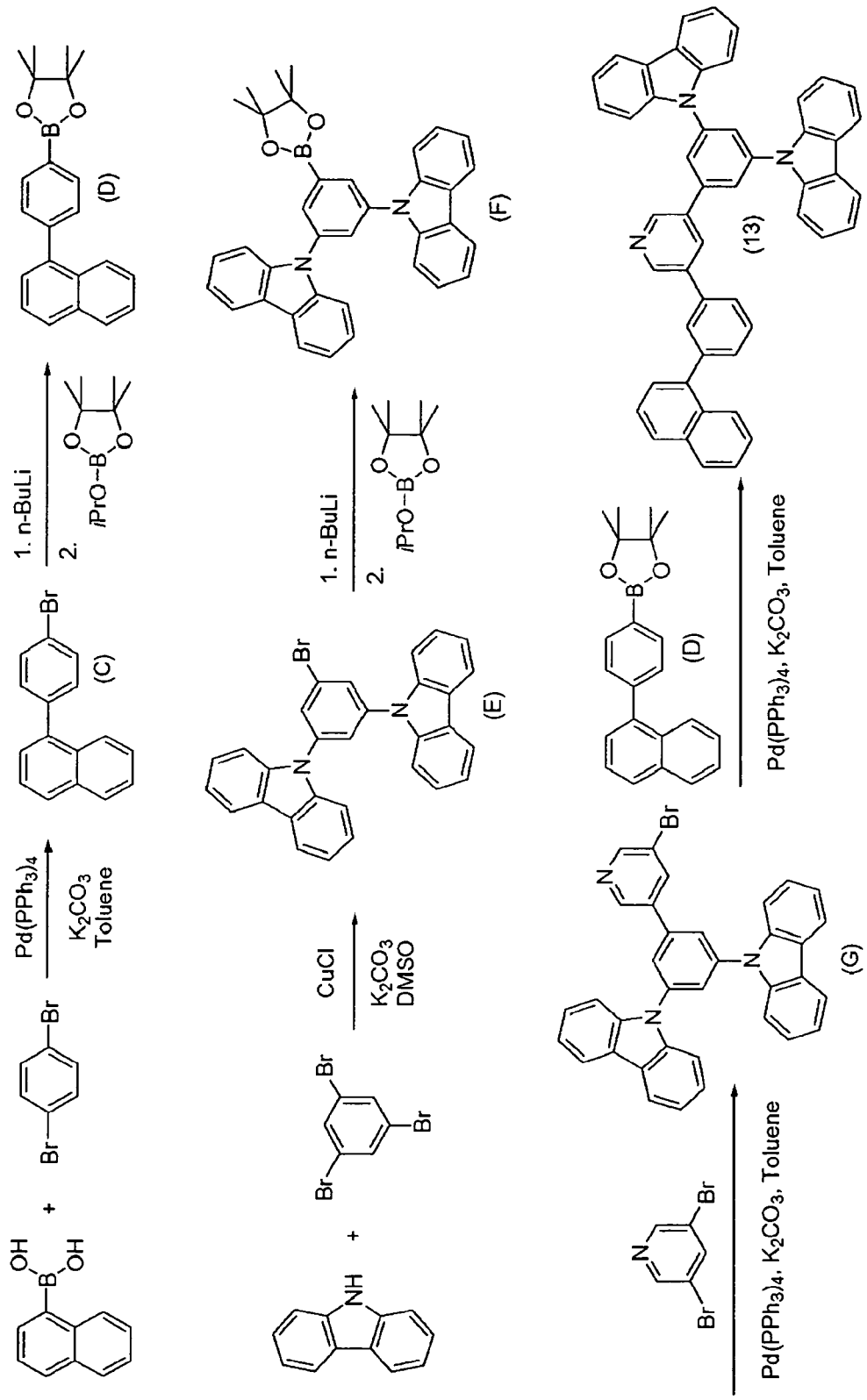
Figure 16:
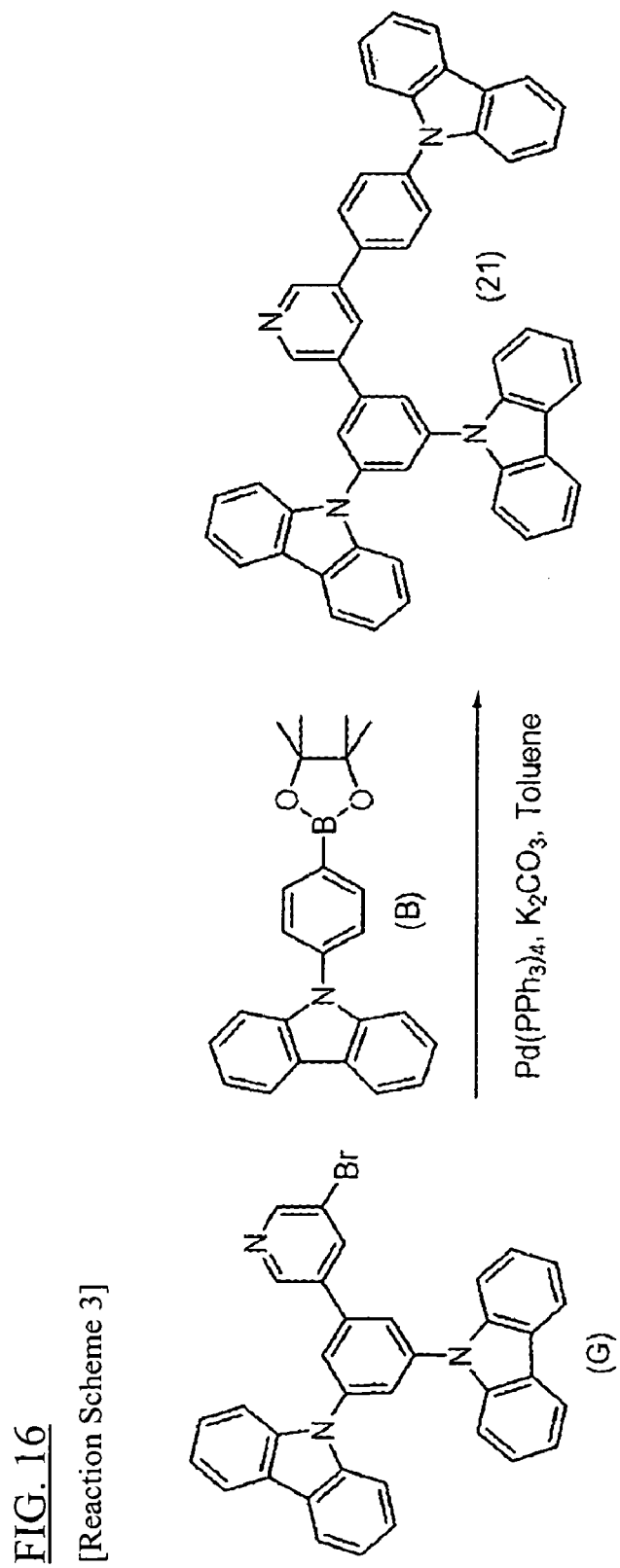
Figure 17:
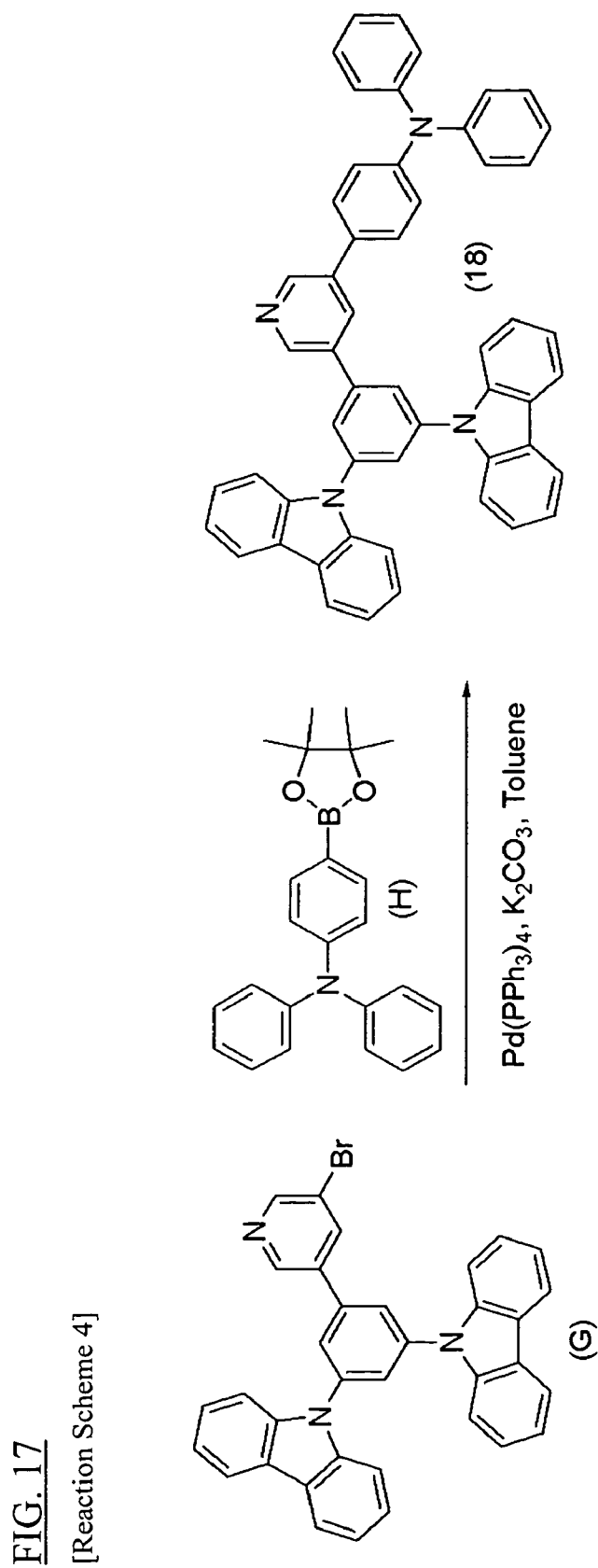
Figure 18:
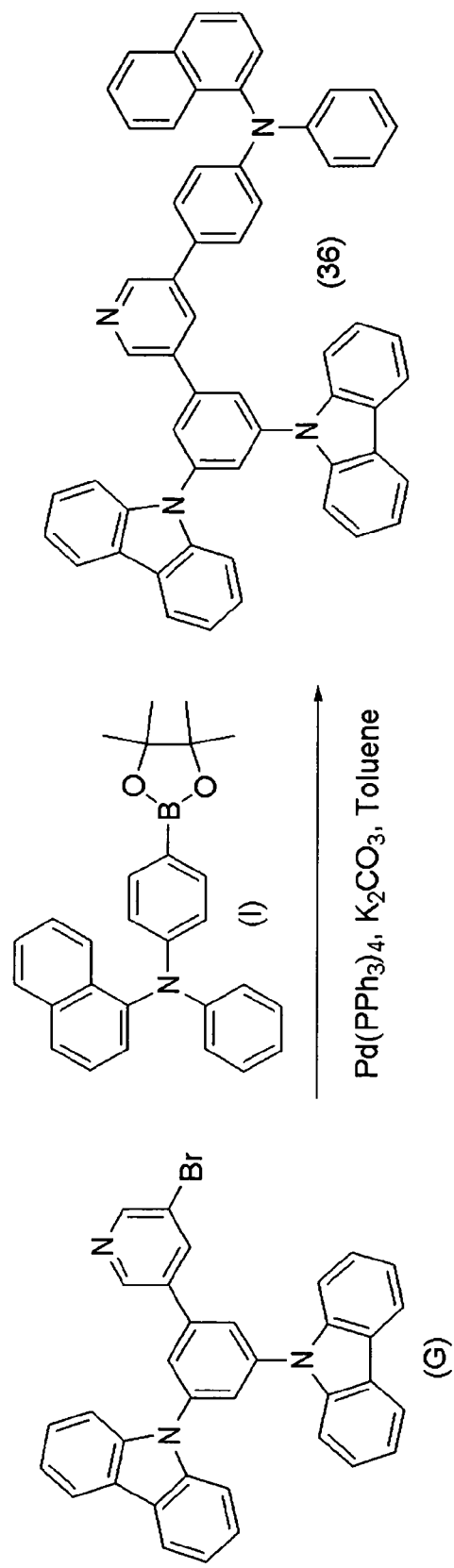

As shown in FIG. 5, a five layered organic photoelectric device 500 includes the organic thin layer 105 including an electron transport layer (ETL) 150, an emission layer 130, a hole transport layer (HTL) 140, and a hole injection layer (HIL) 170, and further includes an electron injection layer (EIL) 160 to achieve the low voltage.

In order to form the organic thin layer 105 having one to five layers, the method may follow a dry coating method such as evaporation, sputtering, plasma plating, and ion plating, or a wet coating method such as spin coating, dipping, and flow coating.

In one embodiment of the present invention, at least one layer such as the emission layer, electron transport layer (ETL), electron injection layer (EIL), hole transport layer (HTL), hole injection layer (HIL), hole blocking layer, and includes a material for the organic photoelectric device according to an embodiment, e.g., including a compound represented by Formula 1.

The organic thin layer includes the phosphorescent light emitting compound such as a metal complex that emits light due to the multiple excitation into a triplet or higher state.

The following examples illustrate the present invention in more detail. However, it is understood that the present invention is not limited by these examples.

FIGS. 14 through 19 respectively illustrate Reaction Schemes 1 through 6, which are described below.

1. Synthesis of Material for an Organic Photoelectric Device

Example 1

Synthesis of Compound (3)

Compound (3) as a material for an organic photoelectric device was synthesized as shown in the following Reaction Scheme 1.

[Reaction Scheme 1]

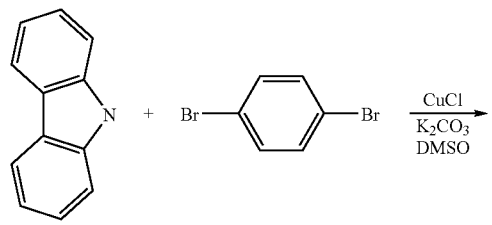

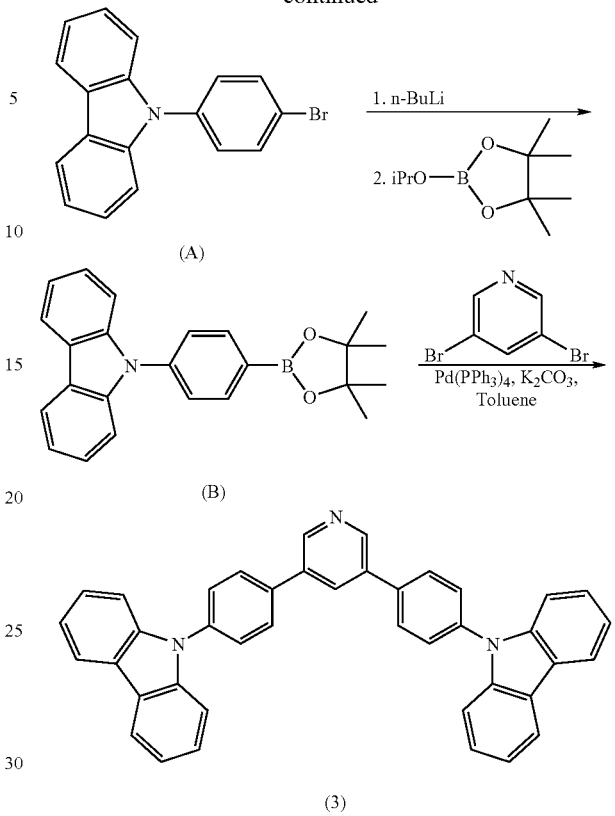

Step 1: Synthesis of Intermediate (A)

50.8 g (304 mmol) of carbazole, 71.6 g (304 mmol) of 1,4-dibromobenzene, 3.76 g (38 mmol) of cuprous chloride, and 83.9 g (607 mmol) of potassium carbonate were suspended in 322 ml of dimethylsulfoxide, and heated and refluxed under a nitrogen atmosphere for 8 hours. The reaction fluid was cooled to room temperature and recrystallized with methanol.

The precipitated crystals were separated by filtration and the obtained residue was purified by silica gel column chromatography, providing 59.9 g of the intermediate (A) (yield 61.3%).

Step 2: Synthesis of Intermediate (B)

37.8 g (117 mmol) of the intermediate (A) was dissolved in 378 ml of tetrahydrofuran; then 100.5 ml (161 mmol) of n-butyl lithium hexane solution (1.6M) was added thereto under an argon atmosphere at −70° C. The obtained solution was agitated at −70° C. to 40° C. for 1 hour. The reaction fluid was frozen to −70° C., and 47.9 ml (235 mmol) of isopropyl tetramethyl dioxaborolane was slowly added thereto in a dropwise fashion. The obtained solution was agitated at −70° C. for 1 hour and heated to room temperature, and then agitated for 6 hours. To the obtained reaction solution, 200 ml of water was added and agitated for 20 minutes.

The reaction solution was separated into two liquid layers, and an organic layer thereof was dried with anhydrous sodium sulfate. After the organic solvent was removed under a reduced pressure, the obtained residue was purified with silica gel column chromatography to provide 28.9 g of the intermediate (B) (yield 66.7%).

Step 3: Synthesis of Compound (3)

10.3 g (28 mmol) of the intermediate (B), 3.0 g (13 mmol) of 3,5-dibromopyridine, and 0.73 g (0.6 mmol) of tetrakis-(triphenyl phosphine) palladium were suspended in 90 ml of tetrahydrofuran and 60 ml of toluene, then added with a solution of 7.0 g (51 mmol) of potassium carbonate dissolved in 60 ml of water. The obtained mixture was heated and refluxed for 9 hours.

The reaction fluid was separated into two layers, and an organic layer thereof was cleaned with a sodium chloride saturated aqueous solution and dried with anhydrous sodium sulfate. Subsequently, the organic solvent was removed by distillation under reduced pressure, and the residue was recrystallized with toluene. The precipitated crystals were separated by filtration and cleaned with toluene to provide 5.5 g (77.3%) of the compound (3).

Example 2

Synthesis of Compound (13)

Compound (13) as a material for an organic photoelectric device was synthesized as shown in the following Reaction Scheme 2.

[Reaction Scheme 2]

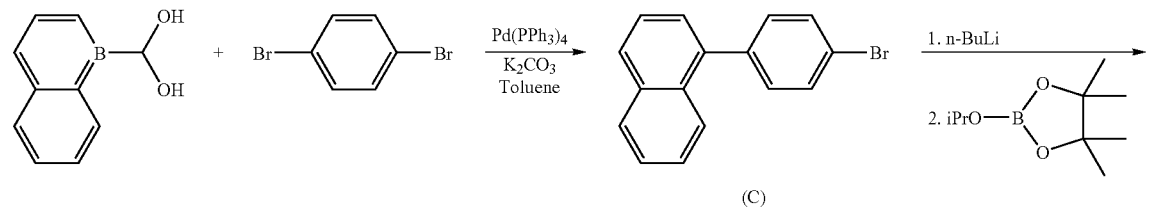

(C)

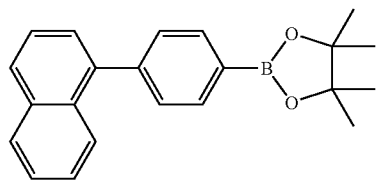

(D)

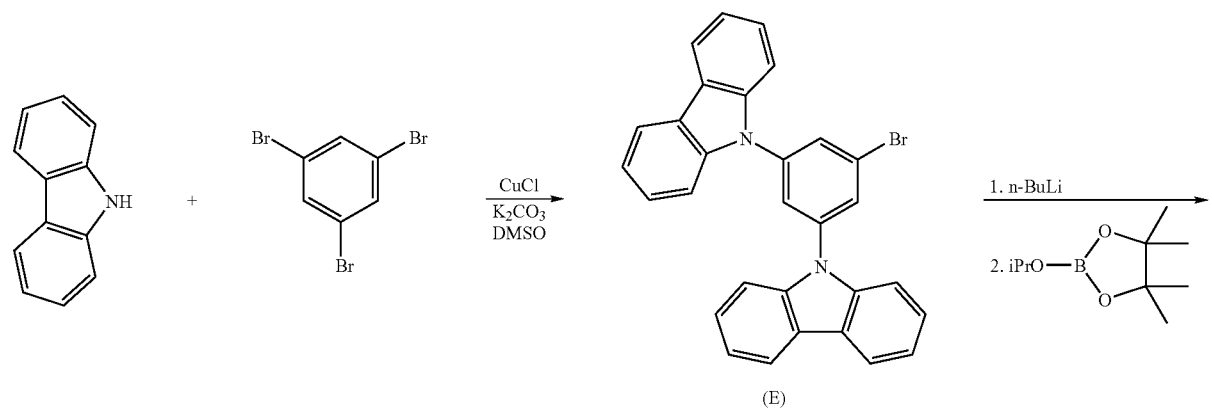

(E)

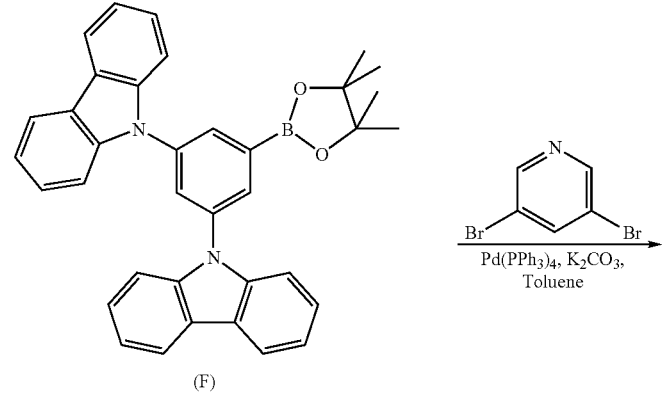

(F)

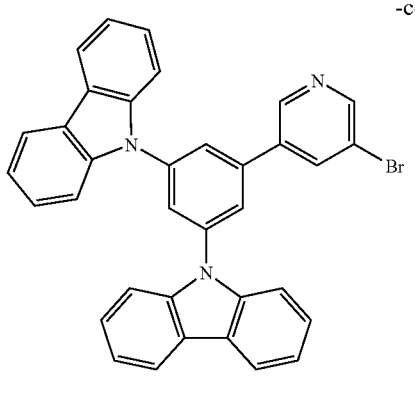

(G)

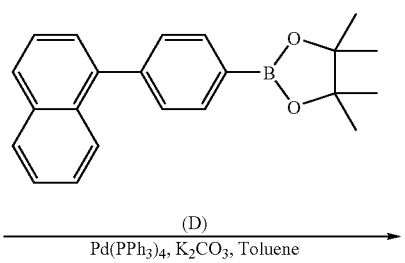

(D)

Pd(PPh₃)₄, K₂CO₃, Toluene

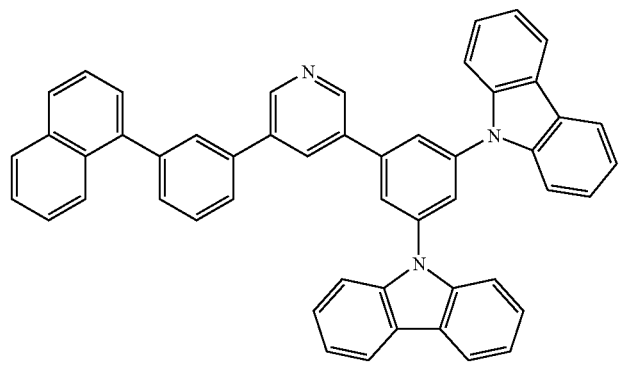

(13)

Step 1: Synthesis of Intermediate (C)

15 g (63 mmol) of 1,4-dibromobenzene, 7.66 g (44 mmol) of 1-naphthaleneboron acid, 17.58 g (127 mmol) of potassium carbonate, and 1.83 g (50 mmol) of tetrakis-(triphenylphosphine) palladium were suspended in a mixed solvent including 200 ml of tetrahydrofuran, 200 ml of toluene, and 50 ml of purified water, and heated and refluxed under a nitrogen atmosphere for 24 hours.

The reaction fluid was cooled to room temperature, and separated into two layers. Then, the solvent of an organic layer thereof was removed under a reduced pressure to provide a fluid. The fluid was separated by column chromatography (hexane) to remove the solvent and to provide 15 g of a gel intermediate (C) at a yield of 83%.

Step 2: Synthesis of Intermediate (D)

7 g (24 mmol) of the intermediate (C) was dissolved in 50 ml of tetrahydrofuran, and added with 15 ml (24 mmol) of an n-butyl lithium hexane solution (1.6M) under an argon atmosphere at −70° C. The obtained solution was agitated at −70° C. for 30 minutes, and the reaction fluid was slowly added with 47.9 ml (235 mmol) of isopropyl tetramethyl dioxaborolane in a dropwise fashion. After the obtained solution was agitated at −70° C. for 1 hour, it was heated to room temperature and agitated for 6 hours. To the obtained reaction solution, 200 ml of water was added and agitated for 20 minutes.

After the reaction solution was separated into two liquid layers, an organic solvent thereof was removed under a reduced pressure. The obtained residue was purified with silica gel column chromatography to provide 6 g of the intermediate (D) at a yield of 73%.

Step 3: Synthesis of Intermediate (E)

40.4 g (241 mmol) of carbazole, 38.0 g (121 mmol) of 1,3,5-tribromobenzene, 2.99 g (30 mmol) of cuprous chloride, and 66.7 g (483 mmol) of potassium carbonate were suspended in 171 ml of dimethylsulfoxide, and heated and refluxed under a nitrogen atmosphere for 8 hours.

The reaction fluid was cooled to room temperature and recrystallized with methanol. The precipitated crystals were separated by filtration, and the obtained residue was purified with silica gel column chromatography to provide 36.7 g of the intermediate (E) at a yield of 62.4%.

Step 4: Synthesis of Intermediate (F)

35.0 g (72 mmol) of the intermediate (E) was dissolved in 350 ml of tetrahydrofuran and added with 61.5 ml (98 mmol) of an n-butyllithium hexane solution (1.6M) under an argon atmosphere at −70° C. The obtained solution was agitated at −70° C. to 40° C. for 1 hour. The reaction flux was frozen to −70° C. and slowly added with 29.3 ml (144 mmol) of isopropyl tetramethyl dioxaborolane in a dropwise fashion. The obtained solution was agitated at −70° C. for 1 hour, and heated to room temperature and agitated for 6 hours. The obtained reaction solution was added with 200 ml of water and agitated for 20 minutes.

After the reaction solution was separated into two liquid layers, an organic layer thereof was dried with anhydrous sodium sulfate. After the organic solvent was removed under a reduced pressure, the obtained residue was purified with silica gel column chromatography to provide 25.1 g (yield 65.4%) of the intermediate (F).

Step 5: Synthesis of Intermediate (G)

45.1 g (84 mmol) of the intermediate (F), 20.0 g (84 mmol) of 3,5-dibromopyridine, and 2.44 g (2.1 mmol) of tetrakis-(triphenyl phosphine) palladium were suspended in 600 ml of tetrahydrofuran and 400 ml of toluene, and then the suspension was added with a solution in which 23.3 g (169 mmol) of potassium carbonate was dissolved in 400 ml of water. The obtained mixture was heated and refluxed for 9 hours. The reaction fluid was separated into two layers, and an organic layer thereof was cleaned with a sodium chloride saturated aqueous solution and dried with anhydrous sodium sulfate.

The organic solvent was removed by distillation under a reduced pressure, and the residue was recrystallized by toluene. The precipitated crystals were separated by filtration and cleansed with toluene to provide 30.7 g (64.4%) of the intermediate (G).

Step 6: Synthesis of Compound (13)

4 g (7 mmol) of intermediate (G), 2.81 g (8.5 mmol) of the intermediate (D), 1.96 g (14 mmol) of potassium carbonate, and 0.41 g (0.3 mmol) of tetrakis-(triphenylphosphine) palladium were suspended in 200 ml of toluene, 200 ml of tetrahydrofuran, and 50 ml of purified water, then heated and agitated for 24 hours.

After the reaction temperature was lowered to room temperature, the resultant was separated to two layers and a solvent of an organic layer thereof was removed under a reduced pressure. The obtained residue was purified by silica gel column chromatography to provide 4 g (82%) of the compound (13).

Example 3

Synthesis of Compound (21)

Compound (21) as a material for an organic photoelectric device was synthesized in accordance with a process as shown in the following Reaction Scheme 3.

[Reaction Scheme 3]

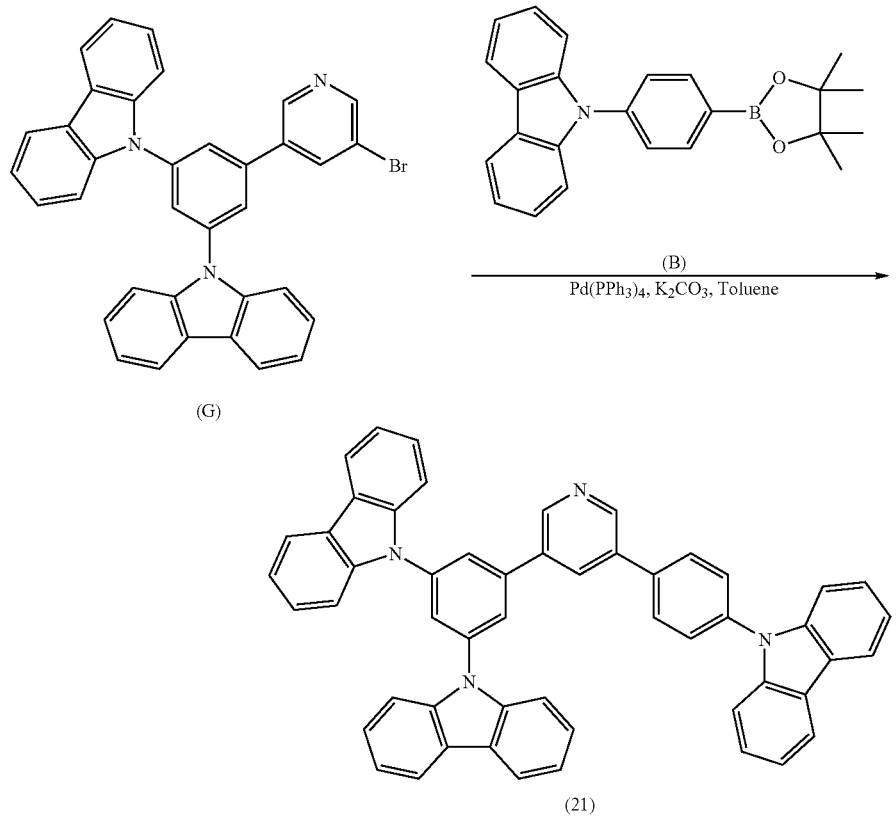

8.64 g (23 mmol) of the intermediate (B), 12.0 g (21 mmol) of the intermediate (G), and 0.74 g (0.6 mmol) of tetrakis-(triphenylphosphine)palladium were suspended in 360 ml of tetrahydrofuran and 240 ml of toluene, and it was added with a solution of 5.88 g (43 mmol) of sodium carbonate dissolved in 240 ml of water. The obtained mixture was heated and refluxed for 9 hours.

After the reaction fluid was separated into two layers, an organic layer thereof was washed with a sodium chloride saturated aqueous solution and dried with anhydrous sodium sulfate. After the organic solvent was removed by distillation under a reduced pressure, the residue was recrystallized with toluene. The precipitated crystals were separated by filtration and washed with toluene to provide 9.8 g (63.4%) of the compound (21). MS (ESI) m/z 727.24 (M+H)$^+$

Example 4
Synthesis of Compound (18)
Compound (18) as a material for an organic photoelectric device was synthesized as shown in the following Reaction Scheme 4.
[Reaction Scheme 4]
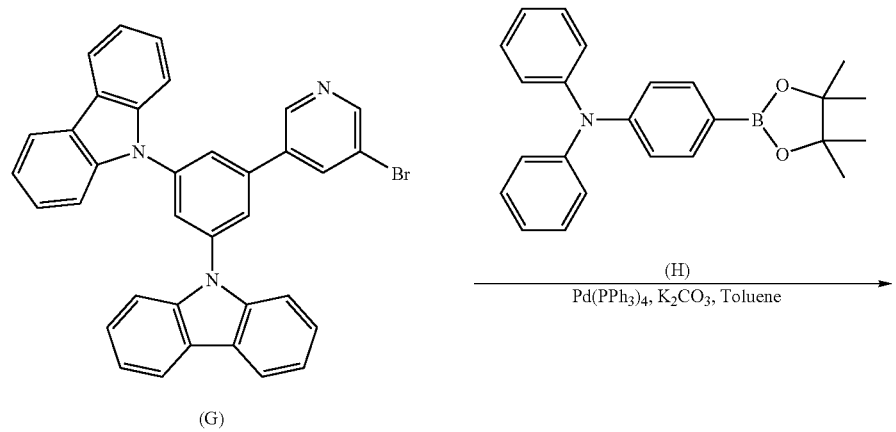
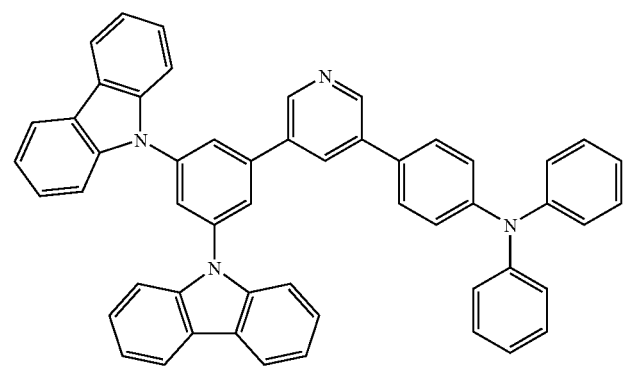

The compound 18 was synthesized according to the same method as in Example 3, except that an intermediate (H) was used instead of the intermediate (B). MS (ESI) m/z 729.25 (M+H)⁺
Example 5
Synthesis of Compound (36)
The compound (36) as a material for an organic photoelectric device was synthesized as shown in the following Reaction Scheme 5.
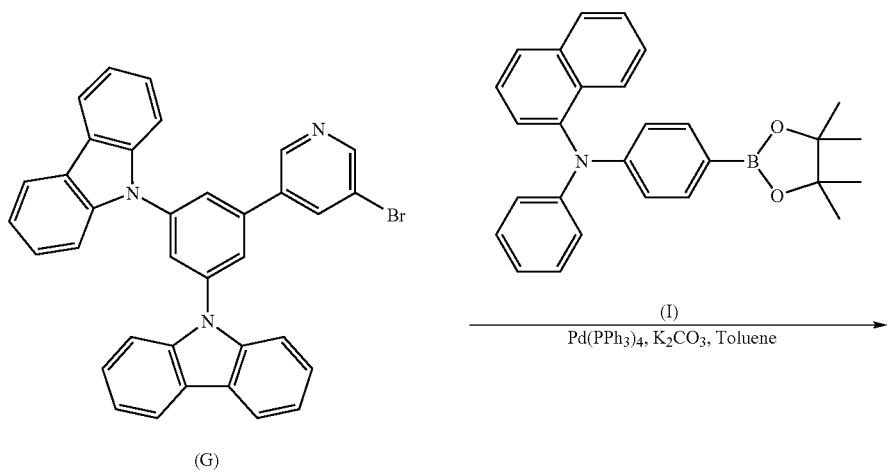
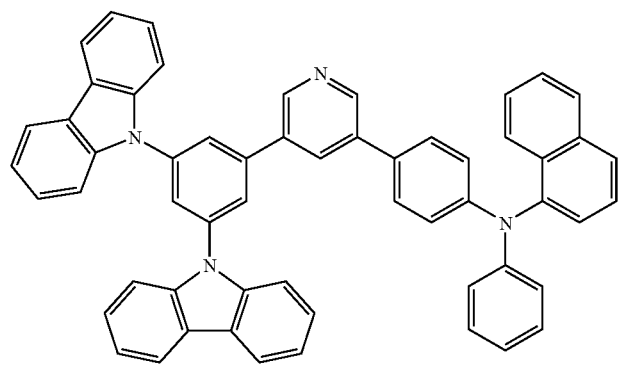

A compound (36) was prepared in accordance with the same procedure as in Example 3, except that an intermediate (I) was used instead of the intermediate (B). MS (ESI) m/z 779.26 (M+H)⁺

Example 6

Synthesis of Compound (22)

Compound (22) was synthesized in accordance with the following Reaction Scheme 6.

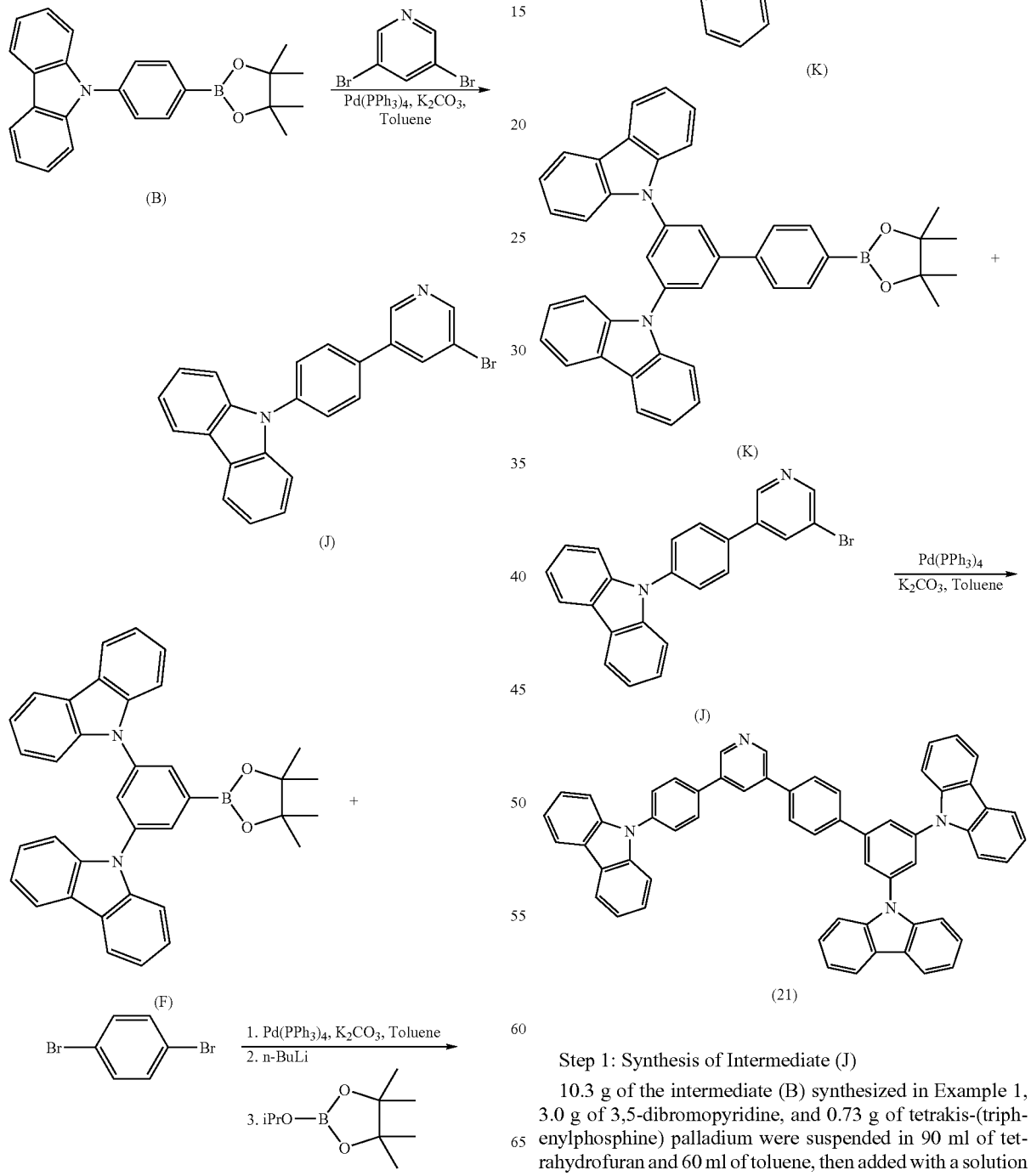

Step 1: Synthesis of Intermediate (J)

10.3 g of the intermediate (B) synthesized in Example 1, 3.0 g of 3,5-dibromopyridine, and 0.73 g of tetrakis-(triphenylphosphine) palladium were suspended in 90 ml of tetrahydrofuran and 60 ml of toluene, then added with a solution of 7.0 g of potassium carbonate dissolved in 60 ml of water.

The obtained mixture was heated and refluxed for 9 hours.

The reaction fluid was separated into two layers, and an organic layer thereof was cleaned with a sodium chloride saturated aqueous solution and dried with anhydrous sodium sulfate. Subsequently, the organic solvent was removed by distillation under reduced pressure, and the residue was recrystallized with toluene. The precipitated crystals were separated by filtration and cleaned with toluene to provide 5.5 g of the intermediate (J).

Step 2: Synthesis of Intermediate (K)

10.3 g of the intermediate (F) synthesized in Example 2, 3.0 g of 1,4-dibromobenzene, 17.58 g of potassium carbonate, and 0.73 g of tetrakis-(triphenylphosphine) palladium were suspended in 200 ml of tetrahydrofuran, 200 ml of toluene, and 50 ml of purified water, and heated and refluxed under a nitrogen atmosphere for 24 hours.

15 ml of an n-butyl lithium hexane solution (1.6M) was added and then the obtained solution was agitated at −70° C. for 30 minutes, and the reaction fluid was slowly added with 47.9 ml (235 mmol) of isopropyl tetramethyl dioxaborolane in a dropwise fashion. After the obtained solution was agitated at −70° C. for 1 hour, it was heated to room temperature and agitated for 6 hours. To the obtained reaction solution, 200 ml of water was added and agitated for 20 minutes. After the reaction solution was separated into two liquid layers, an organic solvent thereof was removed under a reduced pressure. The obtained residue was purified with silica gel column chromatography to provide 6 g of the intermediate (K).

Step 3: Synthesis of Compound (22)

10.3 g of the intermediate (J) synthesized at Step 1, 12.0 g of the intermediate (K), and 0.74 g of tetrakis-(triphenylphosphine) palladium were suspended in 90 ml of tetrahydrofuran and 60 ml of toluene, then added with a solution of 5.88 g of potassium carbonate dissolved in 240 ml of water. The obtained mixture was heated and refluxed for 9 hours.

The reaction fluid was separated into two layers, and an organic layer thereof was cleaned with a sodium chloride saturated aqueous solution and dried with anhydrous sodium sulfate. Subsequently, the organic solvent was removed by distillation under reduced pressure, and the residue was recrystallized with toluene. The precipitated crystals were separated by filtration and cleaned with toluene to provide 9.8 g of the compound (22). MS (ESI) m/z 803.26 (M+H)$^+$ 2. Measurement of Glass Transition Temperature and Thermal Decomposition Temperature Organic compounds synthesized from Examples 1 to 3 and comparative material of CBP were measured for glass transition temperature (Tg) and thermal decomposition temperature Td through differential scanning calorimetry (DSC) and thermalgravimetry (TGA), and the results are shown in the following Table 1.

TABLE 1

| Material | Compound 3 | Compound 13 | Compound 21 | CBP |
|---|---|---|---|---|
| Tg (° C.) | 120 | 144 | 164 | 110 |
| Td (° C.) | 436 | 510 | 500 | 392 |

In Table 1, CBP is a compound represented by the following Formula.

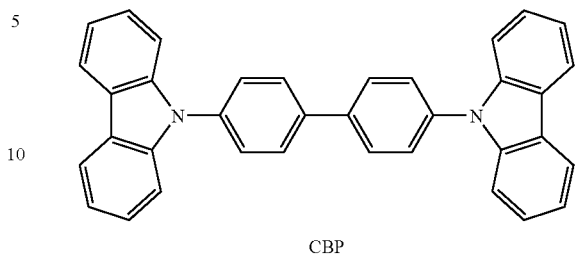

CBP

Referring to Table 1, the organic compounds according to the above Examples of the present invention had a glass transition temperature (Tg) of 120° C. or more and a thermal decomposition temperature (Td) of 430° C. or more according to the DSC and TGA measurement results, which shows that the organic compounds had much higher thermal stability than that of the comparative material, CBP.

3. Fabrication of Phosphorescent Green-Emitting Organic Photoelectric Device, and Evaluation Thereof Organic compounds prepared from Examples 1 to 6 and comparative material, CBP, were used as a host, and Ir(PPy)$_3$ was used as a dopant to provide a phosphorescent green-emitting organic photoelectric device. The obtained device was analyzed for characteristics thereof.

ITO was provided in a thickness of 1000 Å for an anode, and aluminum (Al) was provided in a thickness of 1000 Å for a cathode.

The method of manufacturing an organic photoelectric device may be described in detail as follows: cutting an ITO glass substrate having a sheet resistance value of 15 Ψ/cm$^2$ into a size of 50 mm×50 mm×0.7 mm for a cathode; ultrasonic wave cleaning the same in acetone, isopropyl alcohol, and pure water for 15 minutes, respectively; and UV ozone cleaning for 30 minutes.

N,N'-di(1-naphthyl)-N,N-diphenylbenzidine (NPD) was deposited on the upper surface of the substrate under the conditions of a vacuum degree of 650×10$^{-7}$ Pa and a deposition speed of 0.1 to 0.3 nm/s to provide a hole transport layer (HTL).

Subsequently, under the same vacuum deposition condition, the host material and the phosphorescent dopant were simultaneously deposited to provide an emission layer having a thickness of 300 Å. During this process, a phosphorescent dopant of Ir(PPy)$_3$ was deposited at the same time, and the adding amount of the phosphorescent dopant was adjusted to 5 wt %.

Bis(2-methyl-8-quinolinolate)-4-(phenylphenolate)aluminum (BAlq) and Alg$_a$ were deposited on the upper surface of the emission layer under the same vacuum deposition conditions to provide a hole blocking layer and an electron transport layer (ETL). On the upper surface of the electron transport layer (ETL), LiF and Al were sequentially deposited to provide an organic photoelectric device having the following structure A.

Structure A: NPD 700 Å/EML (5 wt %, 300 Å)/BAlq 50 Å/Alq$_3$ 200 Å/LiF 5 Å/Al

Organic photoelectric devices having the structures B and C were fabricated in accordance with the same process as in the above. TCTA denotes 4,4',4"-tris(N-carbazolyl)tripheny-lamine (4,4',4"-tris(N-carbazolyl)triphenylamine).

Structure B: NPD 700 Å/EML (5 wt %, 300 Å)/Alq₃ 250 Å/LiF 5 Å/Al

Structure C: NPD 600 Å/TCTA 100 Å/EML (5 wt %, 300 Å)/Alq₃ 250 Å/LiF 5 Å/Al

Current density, luminance, and luminous efficiency of each organic photoelectric device in accordance with voltage were measured. Specific measurements were performed as follows.

1) Current Density According to Voltage Change

Each of obtained organic photoelectric devices was measured for a current value passing through the unit device using a current-voltage meter (Keithley 2400) while increasing the voltage from 0V to 10V. The results are calculated by dividing the measured current value by the area.

2) Luminance According to a Voltage Change

Each of obtained organic photoelectric devices was measured for luminance by a luminance meter (Minolta Cs-1000 Å) while increasing the voltage from 0V to 10V.

3) Luminous Efficiency Measurement

Luminous efficiency was calculated from the luminance, current density, and voltage.

Luminous efficiency of the organic photoelectric device having the structure A is shown in the following Table 2. Luminance, driving voltages, and color coordinates are also shown in the following Table 2.

TABLE 2

| | Host material | Luminance (nit) | Driving voltage (V) | Luminous efficiency (lm/W) | Color coordinate (x, y) |
|---|---|---|---|---|---|
| Example 1 | Compound 3 | 100 | 4.1 | 17 | 0.31, 0.60 |
| Example 2 | Compound 13 | 100 | 5.0 | 22 | 0.32, 0.60 |
| Example 3 | Compound 21 | 100 | 4.3 | 30 | 0.32, 0.60 |
| Example 6 | Compound 22 | 100 | 3.9 | 36 | 0.32, 0.62 |
| Comparative Example 1 | CBP | 100 | 6.1 | 14 | 0.30, 0.59 |

As shown in Table 2, devices including hosts of the organic compounds according to the above Examples of the present invention had driving voltages of 5V or less (3.9-5.0V), which were around 2V less than that of comparative material at the same luminance of 100 nit, and improved luminous efficiency that was significantly more than that of comparative material.

The following Table 3 shows the results of measuring characteristics of the organic photoelectric device having structure B.

TABLE 3

| | Host material | Luminance nit | Driving voltage V | Luminous efficiency Lm/W | Color coordinate (x, y) |
|---|---|---|---|---|---|
| Example 1 | Compound 3 | 1000 | 8.6 | 7.4 | 0.26, 0.61 |
| Example 3 | Compound 21 | 1000 | 7.1 | 10.7 | 0.27, 0.61 |
| Example 6 | Compound 22 | 1000 | 7.2 | 9.7 | 0.27, 0.61 |
| Comparative Example 1 | CBP | 1000 | 9.5 | 9.4 | 0.26, 0.63 |

As shown in Table 3, devices including hosts of the organic compounds according to the above Examples of the present invention improved device characteristics in that the driving voltages (7.1-8.6V) were decreased to around 2V less than that of the comparative material, and the luminous efficiency was significantly improved at the same luminance of 1000 nit.

The following Table 4 shows the results for assessing characteristics of the organic photoelectric device having structure C.

TABLE 4

| | Host material | Luminance nit | Driving voltage V | Luminous efficiency | | Color coordinate (x, y) |
|---|---|---|---|---|---|---|
| | | | | cd/A | lm/W | |
| Example 1 | Compound (3) | 1000 | 6.5 | 61.2 | 32.7 | 0.26, 0.61 |
| Example 3 | Compound (21) | 1000 | 6.3 | 58.9 | 32.5 | 0.27, 0.61 |
| Example 6 | Compound (22) | 1000 | 6.4 | 50.2 | 27.4 | 0.27, 0.61 |
| Comparative Example 1 | CBP | 1000 | 7.8 | 42.9 | 19.1 | 0.26, 0.63 |

As shown in Table 4, devices including host materials of the organic compounds according to the above Examples of the present invention showed device characteristics in which the driving voltages (6.3-6.5V) were decreased to maximumally 1.4V less than that of the comparative material, and the luminous efficiency was significantly improved at the same luminance of 1000 nit.

Furthermore, the flowing Table 4 shows results for assessing lifetime of the organic photoelectric device having structure C.

TABLE 5

| | Host material | Initial luminance (nit) | Current (mA) | Half-life (hr) |
|---|---|---|---|---|
| Example 1 | Compound (3) | 3000 | 0.22 | 411 |
| Example 6 | Compound (22) | 3000 | 0.26 | 205 |
| Comparative Example 1 | CBP | 3000 | 0.46 | 82 |

As shown in Table 5, devices including a host of the organic compound according to one embodiment of the present invention improved the lifetime of the device to 500% of that of the comparative material.

4. Fabrication of Phosphorescent Red-Emitting Organic Photoelectric Device, and Evaluation Thereof Organic compounds obtained from Examples 1 to 6 and a comparative material of CBP were used for a host material and Ir(Piq)₃ was used for a red dopant to provide a red phosphorescent organic photoelectric device having structure A, and the characteristics thereof were evaluated. The device was manufactured under the same conditions as in the green phosphorescent device. The obtained devices were measured for characteristics, and the results are shown in the following Table 6:

TABLE 6

| | Host material | Luminance (nit) | Driving voltage (V) | Luminous efficiency (lm/W) | Color coordinate (x, y) |
|---|---|---|---|---|---|
| Example 4 | Compound (18) | 1000 | 9.5 | 1.9 | 0.68, 0.31 |
| Example 5 | Compound (36) | 1000 | 8 | 2.7 | 0.68, 0.31 |

TABLE 6-continued

| | Host material | Luminance (nit) | Driving voltage (V) | Luminous efficiency (lm/W) | Color coordinate (x, y) |
|---|---|---|---|---|---|
| Comparative Example 1 | CBP | 1000 | 10 | 1.6 | 0.68, 0.32 |

As shown in Table 6, devices including a host of organic compound according to one embodiment of the present invention improved device characteristics such as driving voltage and luminous efficiency compared to those of comparative material of CBP at the same luminance of 1000 nit.

As described above, the material for an organic photoelectric device is a phosphorescent material having thermal stability due to a glass transition temperature (Tg) of 120° C. or more and a thermal decomposition temperature of 400° C. or more. The material is capable of realizing a high efficiency organic photoelectric device. The material for an organic photoelectric device includes a bipolar organic compound including both a hole transporting unit and an electron transporting unit. An organic photoelectric device including a material for the organic photoelectric device is also provided. Another embodiment of the present invention provides an organic photoelectric device that includes an anode, a cathode, and organic thin layers disposed between the anode and cathode. The organic thin layer includes the above material for an organic photoelectric device.

Example embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:
1. A material for an organic photoelectric device, the material comprising:
a compound including a pyridine

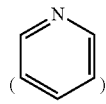

moiety, the compound being a bipolar organic compound including both a hole transporting unit and an electron transporting unit, the compound being represented by the following Formula 1:

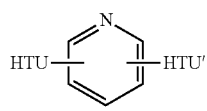

[Formula 1]

wherein, in Formula 1:
the pyridine moiety is an electron transporting unit,
the HTU and HTU' independently function as a hole transporting unit, and
the HTU and HTU' are the same or different; and
a dopant, wherein the compound represented by Formula 1 is a host, and the dopant is a phosphorescent or fluorescent dopant selected from the group consisting of red, green, blue, and white phosphorescent or fluorescent dopants, and combinations thereof.

2. The material as claimed in claim 1, wherein the compound represented by Formula 1 is further represented by the following Formula 2:

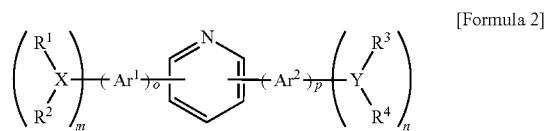

[Formula 2]

wherein, in Formula 2:
X and Y are independently selected from the group consisting of nitrogen (N), sulfur (S), and oxygen (O),
$Ar^1$ and $Ar^2$ are independently selected from the group consisting of a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene,
$R^1$ to $R^4$ are independently selected from the group consisting of a substituted or unsubstituted C6 to C30 aryl, a substituted or unsubstituted C6 to C30 arylene, a substituted or unsubstituted C2 to C30 heteroaryl, a substituted or unsubstituted C2 to C30 heteroarylene, a substituted or unsubstituted C1 to C30 alkyl, a substituted or unsubstituted C1 to C30 alkylene, or $R^1$ and $R^2$ form a cyclic ring or $R^3$ and $R^4$ form a cyclic ring,
when X is sulfur or oxygen, $R^2$ is a unshared electron pair, and when Y is sulfur or oxygen, $R^4$ is a unshared electron pair, and
m and n are independently integers ranging from 0 to 3, m+n is more than or equal to 1, and o and p are integers ranging from 0 to 2.

3. The material as claimed in claim 2, wherein at least one of the groups $XR^1R^2$ and $YR^3R^4$ in Formula 2 is represented by the following Formula 6a:

[Formula 6a]

wherein, in Formula 6a:
$Ar^{16}$ and $Ar^{17}$ are independently selected from the group consisting of a substituted or unsubstituted C6 to C30 aryl and a substituted or unsubstituted C2 to C30 heteroaryl.

4. The material as claimed in claim 2, wherein at least one of the groups $XR^1R^2$ and $YR^3R^4$ in Formula 2 is represented by the following Formula 6b:

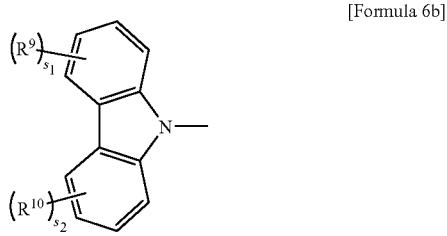

[Formula 6b]

wherein, in Formula 6b:
R$^9$ and R$^{10}$ are independently substituents selected from the group consisting of a substituted or unsubstituted C6 to C30 aryl, a substituted or unsubstituted C2 to C30 heteroaryl, a substituted or unsubstituted C1 to C30 alkyl, a substituted or unsubstituted C2 to C20 alkoxy, and SiR$_{15}$R$_{16}$R$_{17}$(where R$_{15}$ to R$_{17}$ are independently selected from the group consisting of a substituted or unsubstituted C1 to C30 alkyl, a substituted or unsubstituted C1 to C30 aryl, a substituted or unsubstituted C2 to C30 heteroaryl, a substituted or unsubstituted C3 to C30 cycloalkyl, a nitrile, a cyano, a nitro, a carbonyl, and an amide), and
s$_1$ and s$_2$ are independently integers ranging from 0 to 4.

5. The material as claimed in claim 2, wherein at least one of the groups XR$^1$R$^2$ and YR$^3$R$^4$ in Formula 2 is represented by the following Formula 6c:

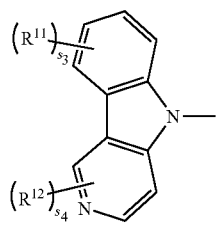

[Formula 6c]

wherein, in Formula 6c:
R$^{11}$ and R$^{12}$ are independently substituents selected from the group consisting of a substituted or unsubstituted C6 to C30 aryl, a substituted or unsubstituted C2 to C30 heteroaryl, a substituted or unsubstituted C1 to C30 alkyl, a substituted or unsubstituted C2 to C20 alkoxy, and SiR$_{15}$R$_{16}$R$_{17}$ (where R$_{15}$ to R$_{17}$ are independently selected from the group consisting of a substituted or unsubstituted C1 to C30 alkyl, a substituted or unsubstituted C1 to C30 aryl, a substituted or unsubstituted C2 to C30 heteroaryl, a substituted or unsubstituted C3 to C30 cycloalkyl, a nitrile, a cyano, a nitro, a carbonyl, and an amide), and
s$_3$ and s$_4$ are independently integers ranging from 0 to 4.

6. The material as claimed in claim 2, wherein at least one of the groups XR$^1$R$^2$ and YR$^3$R$^4$ in Formula 2 is represented by the following Formula 6d:

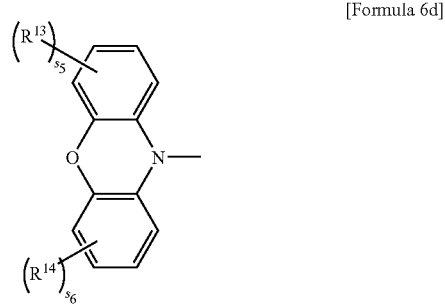

[Formula 6d]

wherein, in Formula 6d:
R$^{13}$ and R$^{14}$ are independently substituents selected from the group consisting of a substituted or unsubstituted C6 to C30 aryl, a substituted or unsubstituted C2 to C30 heteroaryl, a substituted or unsubstituted C1 to C30 alkyl, a substituted or unsubstituted C2 to C20 alkoxy, and SiR$_{15}$R$_{16}$R$_{17}$ (where R$_{15}$ to R$_{17}$ are independently selected from the group consisting of a substituted or unsubstituted C1 to C30 alkyl, a substituted or unsubstituted C1 to C30 aryl, a substituted or unsubstituted C2 to C30 heteroaryl, a substituted or unsubstituted C3 to C30 cycloalkyl, a nitrile, a cyano, a nitro, a carbonyl, and an amide), and
s$_5$ and s$_6$ are independently integers ranging from 0 to 4.

7. The material as claimed in claim 2, wherein the compound represented by Formula 2 is selected from the group consisting of the following Compounds (1) to (41), and combinations thereof:

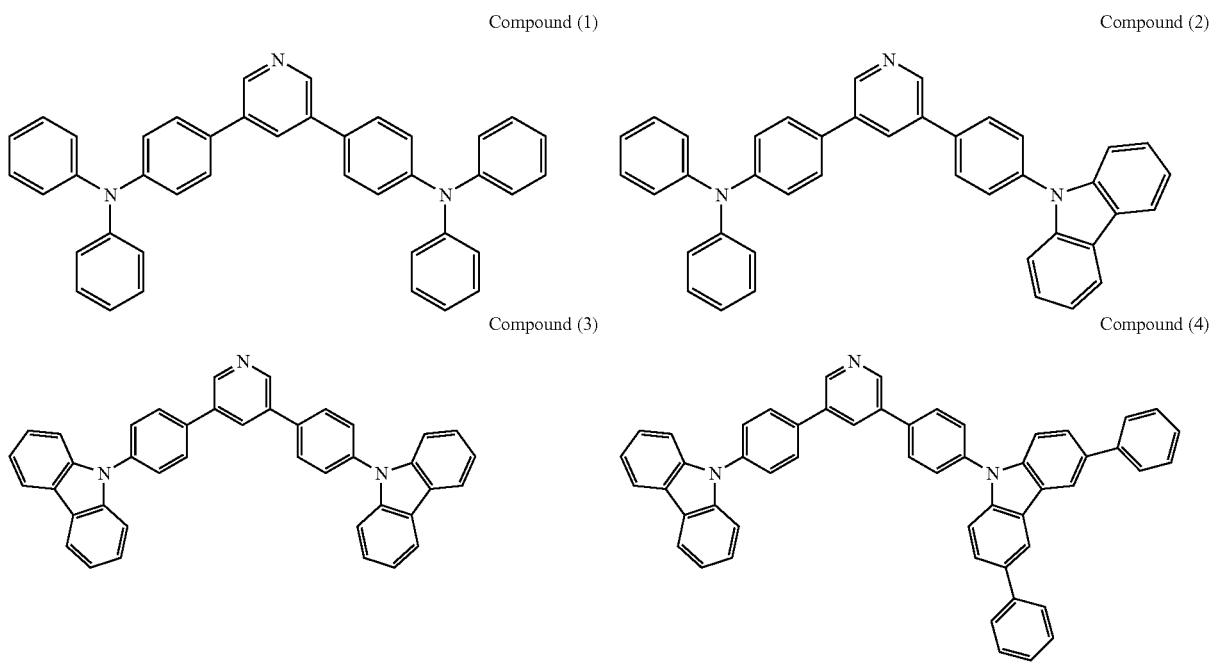

Compound (1)

Compound (2)

Compound (3)

Compound (4)

-continued
Compound (5)
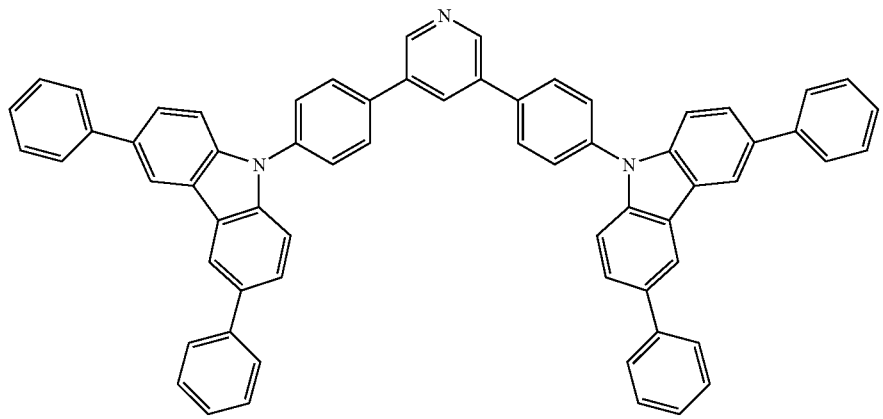
Compound (6)
Compound (7)
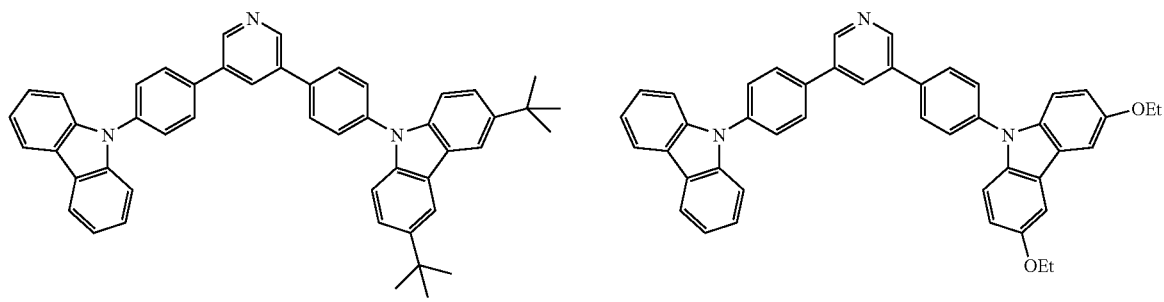
Compound (8)
Compound (9)
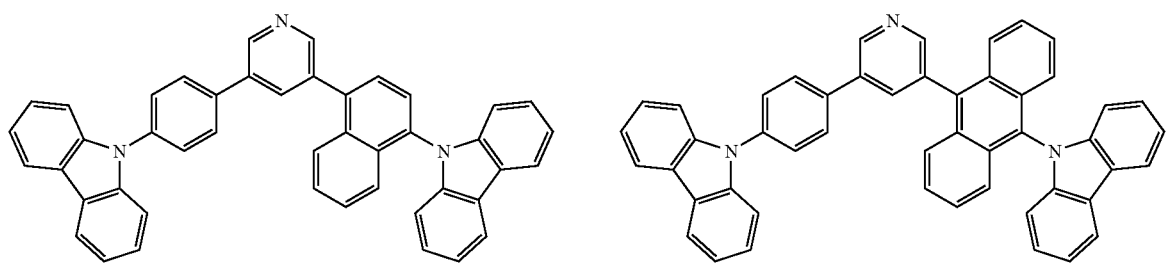
Compound (10)
Compound (11)
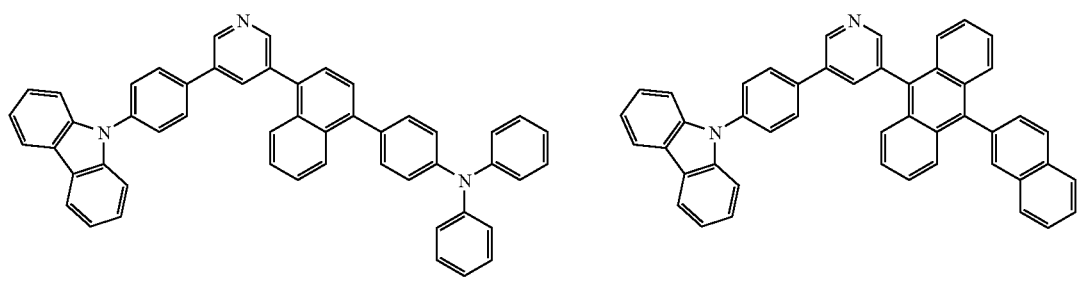

-continued
Compound (12)
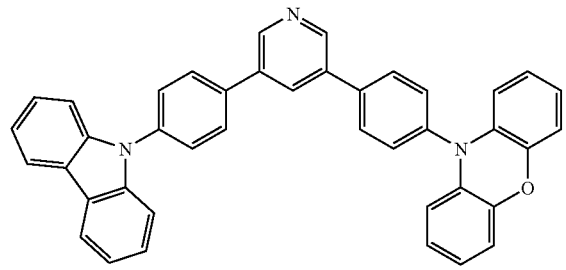
Compound (13)
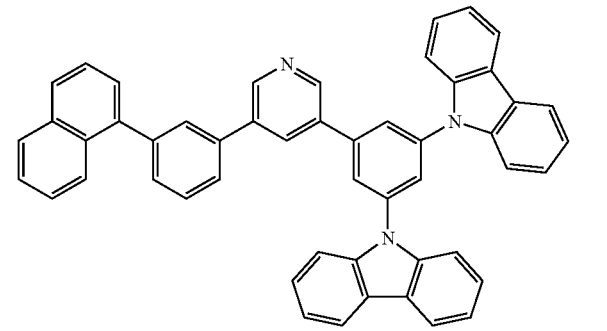
Compound (14)
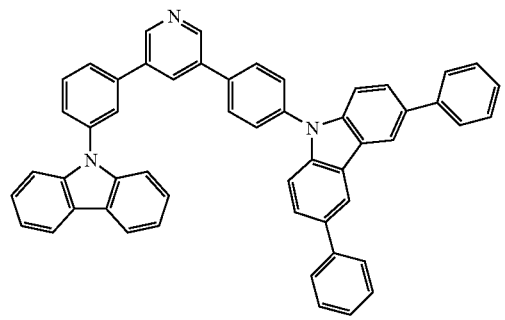
Compound (15)
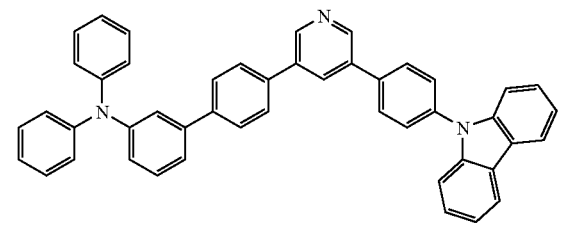
Compound (16)
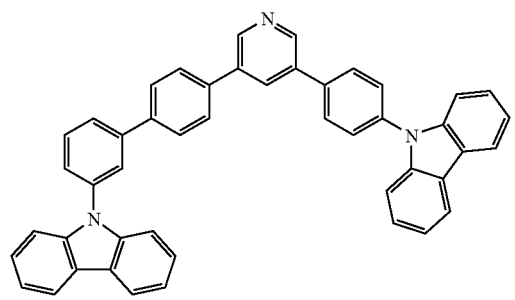
Compound (17)
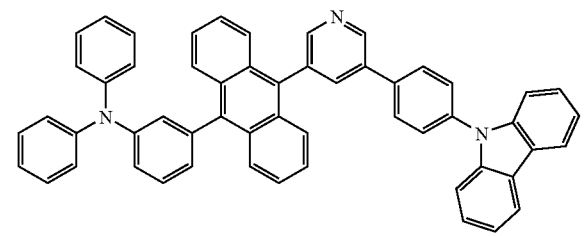
Compound (18)
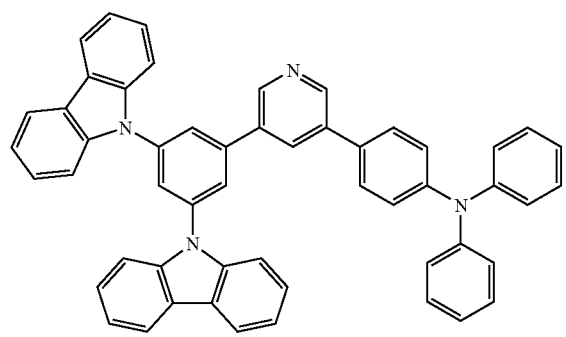
Compound (19)
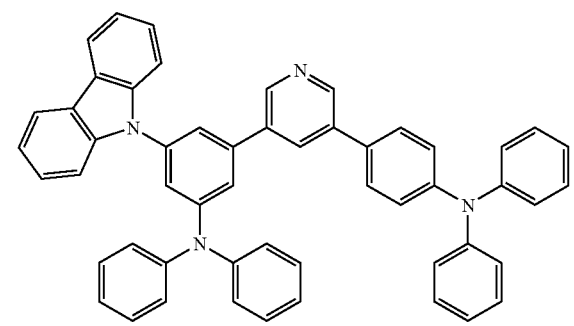

-continued
Compound (20)
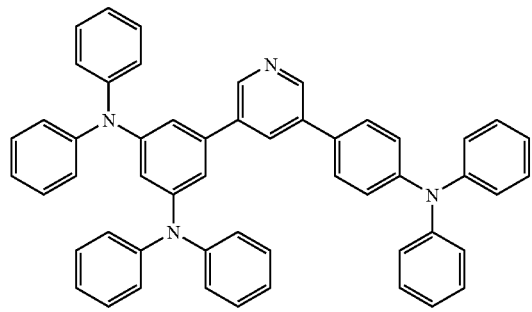
Compound (21)
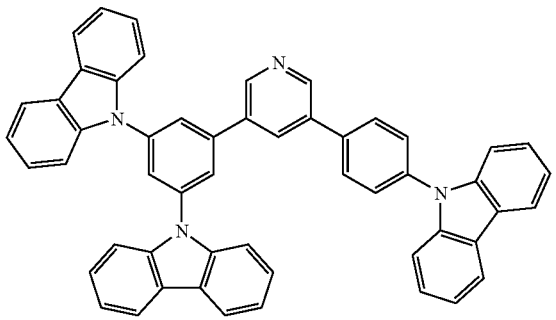
Compound (22)
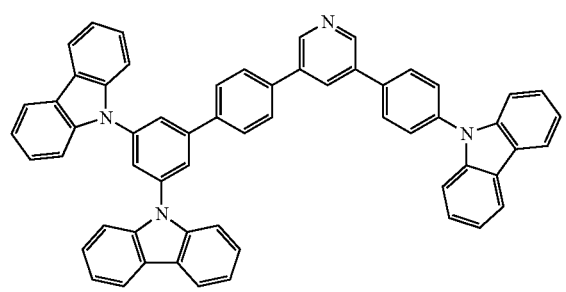
Compound (23)
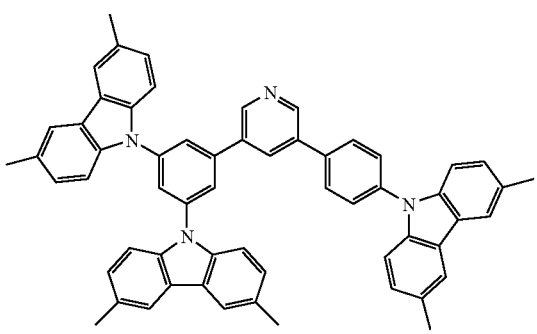
Compound (24)
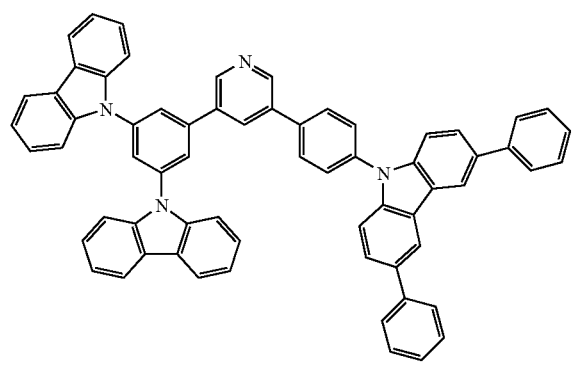
Compound (25)
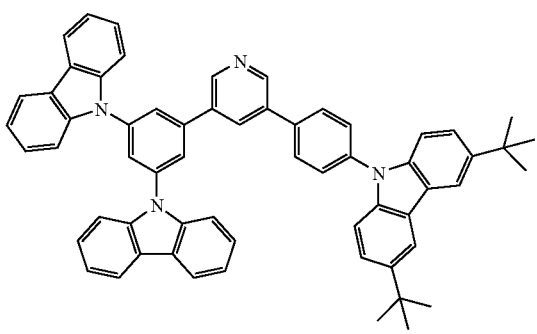
Compound (26)
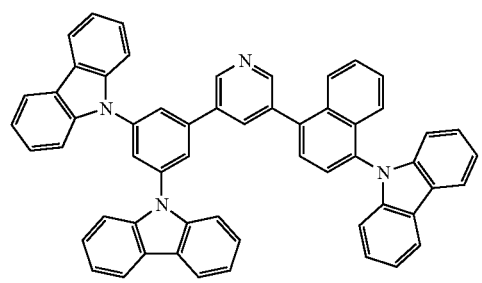
Compound (27)
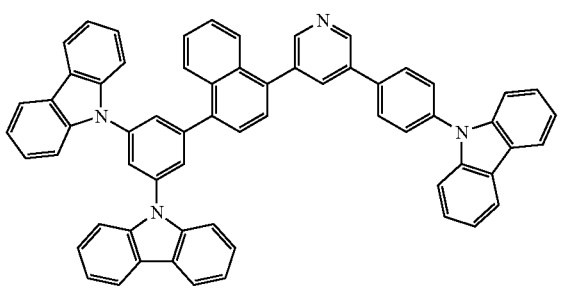

-continued
Compound (28)
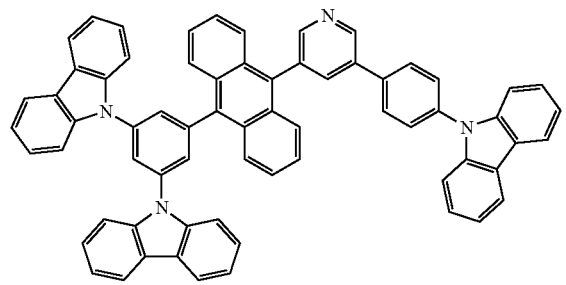
Compound (29)
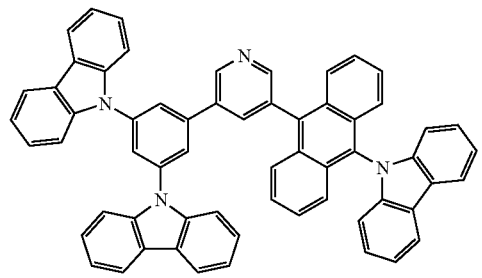
Compound (30)
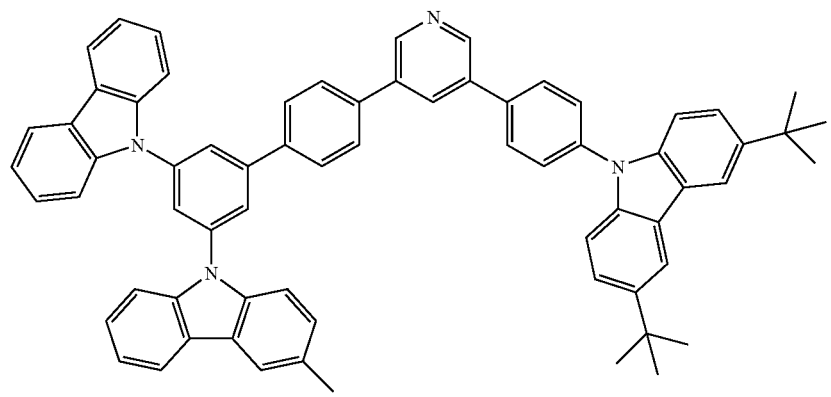
Compound (31)
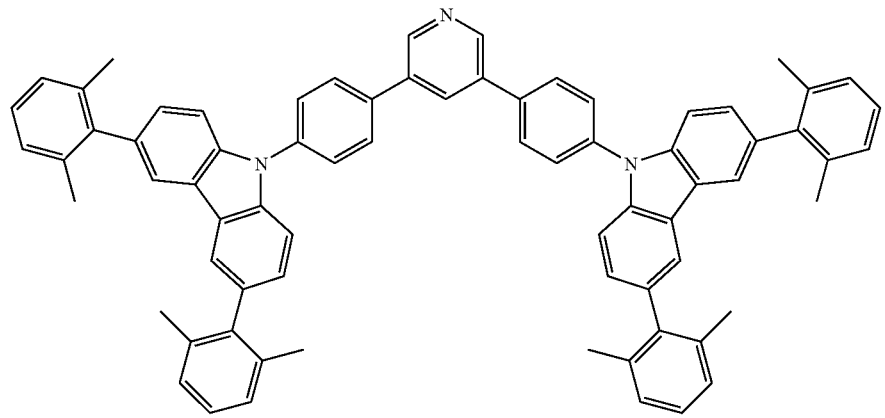
Compound (32)
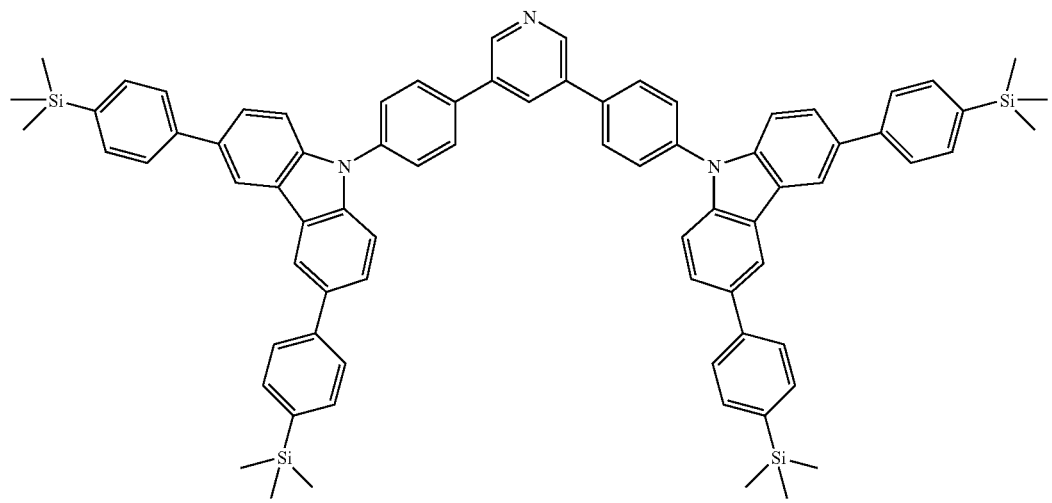

-continued
Compound (33)
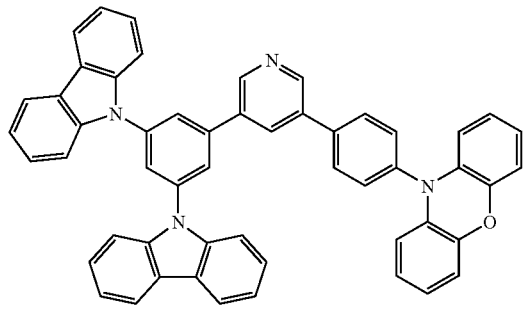
Compound (34)
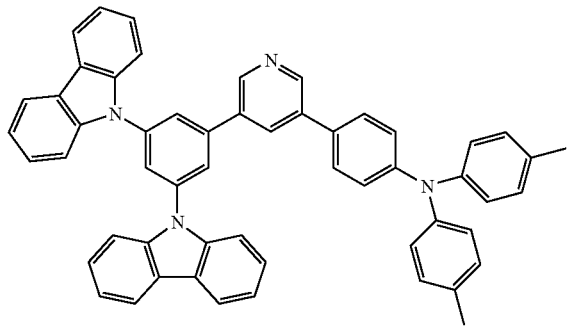
Compound (35)
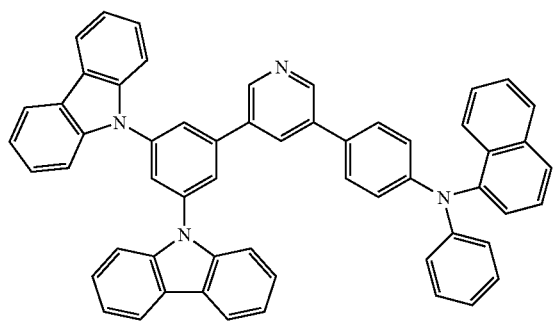
Compound (36)
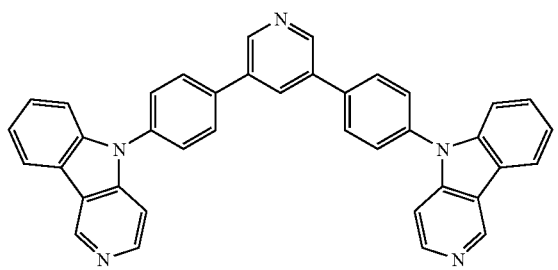
Compound (37)
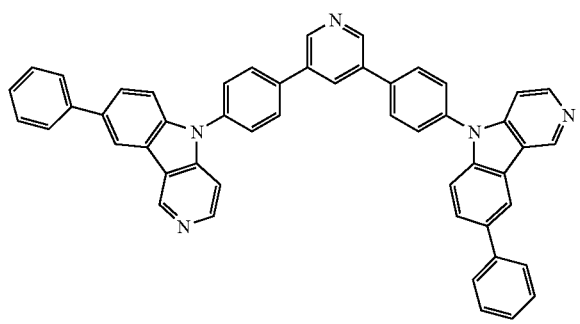
Compound (38)
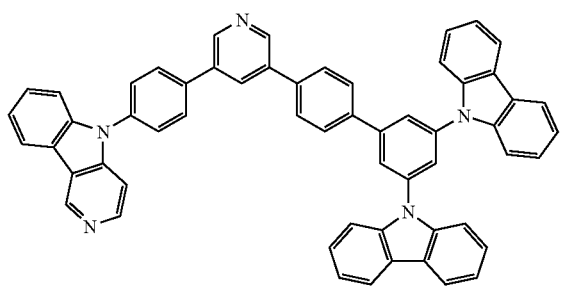
Compound (39)
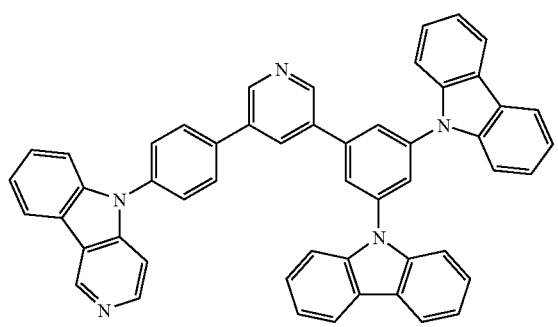
Compound (40)
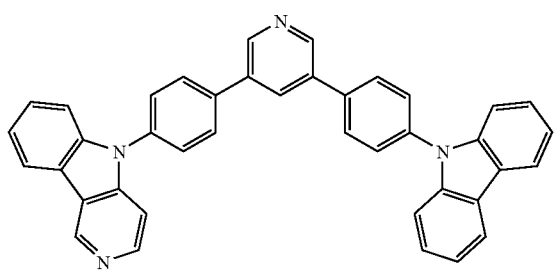

Compound (41)

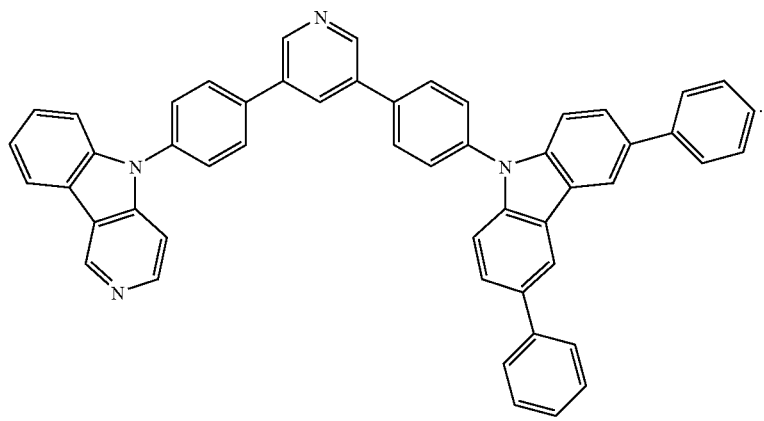

8. The material as claimed in claim 1, wherein the compound represented by Formula 1 is further represented by the following Formula 3:

[Formula 3]

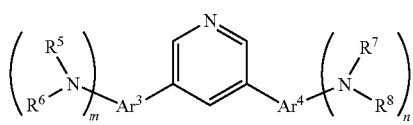

wherein, in Formula 3:
Ar³ and Ar⁴ are independently selected from the group consisting of a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene,
$R^5$ to $R^8$ are independently selected from the group consisting of a substituted or unsubstituted C6 to C30 aryl, a substituted or unsubstituted C6 to C30 arylene, a substituted or unsubstituted C2 to C30 heteroaryl, a substituted or unsubstituted C2 to C30 heteroarylene, a substituted or unsubstituted C1 to C30 alkyl, and a substituted or unsubstituted C1 to C30 alkylene, or $R^5$ and $R^6$ form a cyclic ring or $R^7$ and $R^8$ form a cyclic ring, and
m and n are independently integers ranging from 0 to 3, and m+n is more than or equal to 1.

9. The material as claimed in claim 1, wherein the compound represented by Formula 1 is further represented by the following Formula 4:

[Formula 4]

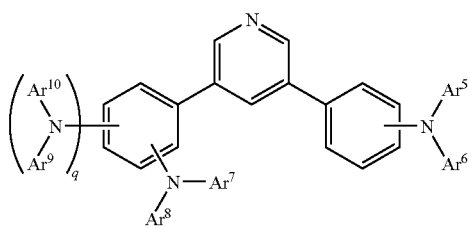

wherein, in Formula 4:
$Ar^5$ to $Ar^{10}$ are independently selected from the group consisting of a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene, or $Ar^5$ and $Ar^6$ form a cyclic ring, $Ar^7$ and $Ar^8$ form a cyclic ring, or $Ar^9$ and $Ar^{10}$ form a cyclic ring, and
q is an integer ranging from 0 to 2.

10. The material as claimed in claim 1, wherein the compound represented by Formula 1 is further represented by the following Formula 5:

[Formula 5]

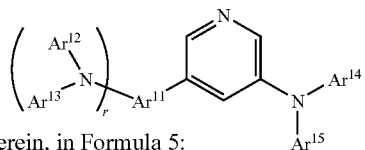

wherein, in Formula 5:
$Ar^{11}$ to $Ar^{15}$ are independently selected from the group consisting of a substituted or unsubstituted C6 to C30 aryl, a substituted or unsubstituted C6 to C30 arylene, a substituted or unsubstituted C1 to C30 alkyl, a substituted or unsubstituted C1 to C30 alkylene, a substituted or unsubstituted C2 to C30 heteroaryl, and a substituted or unsubstituted C2 to C30 heteroarylene, or $Ar^{12}$ and $Ar^{13}$ form a cyclic ring, or $Ar^{14}$ and $Ar^{15}$ form a cyclic ring, and
r is an integer ranging from 0 to 2.

11. The material as claimed in claim 10, wherein the compound represented by Formula 5 is selected from the group consisting of the following Compounds (42) to (52), and combinations thereof:

Compound (42)

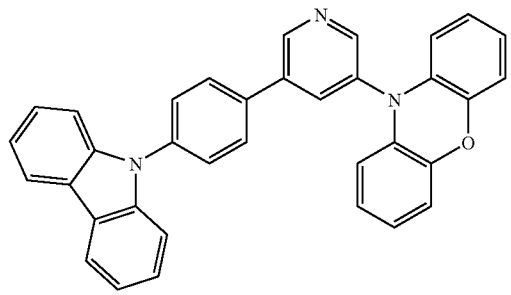

Compound (43)
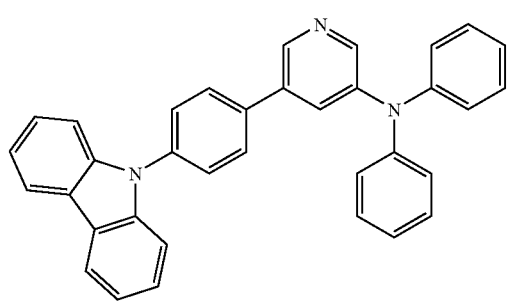
Compound (44)
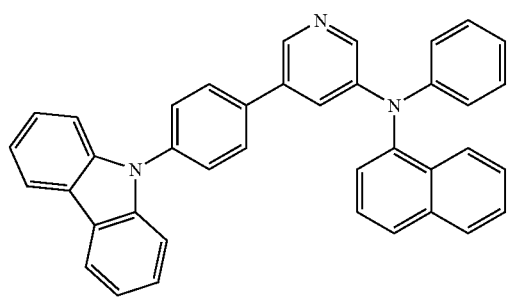
Compound (45)
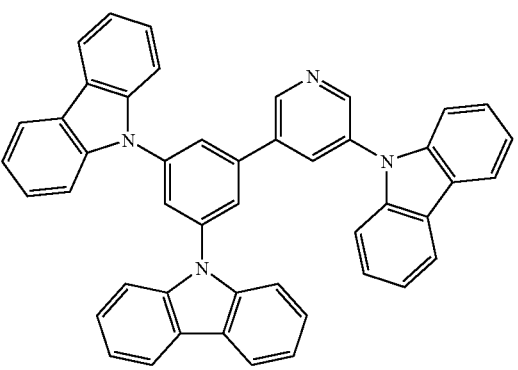
Compound (46)
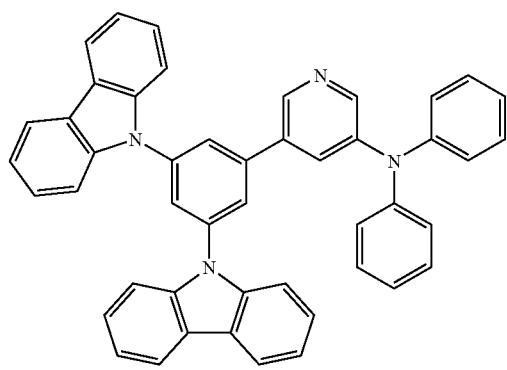
Compound (47)
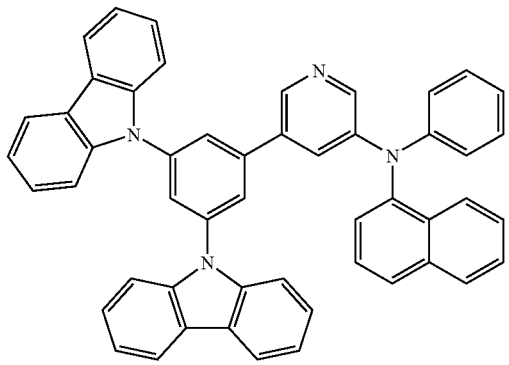
Compound (48)
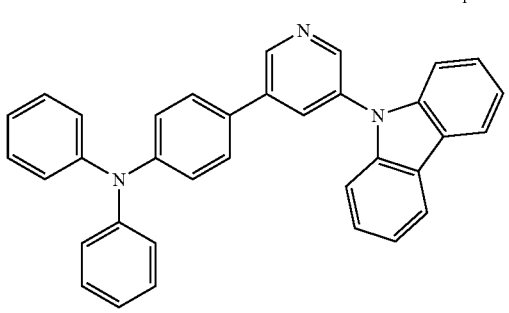
Compound (49)
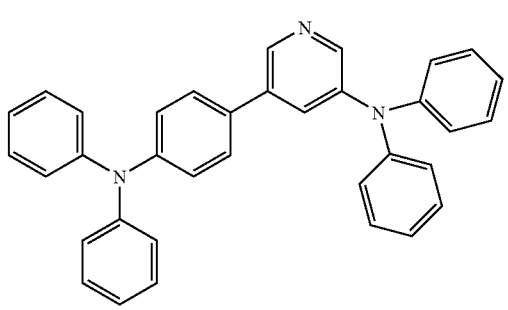
Compound (50)
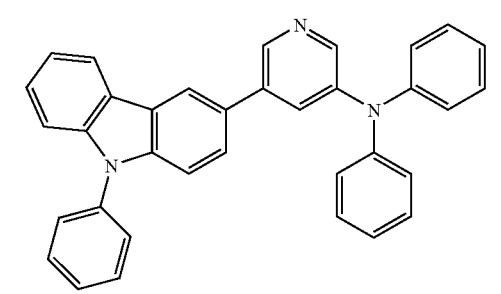

-continued

Compound (51)

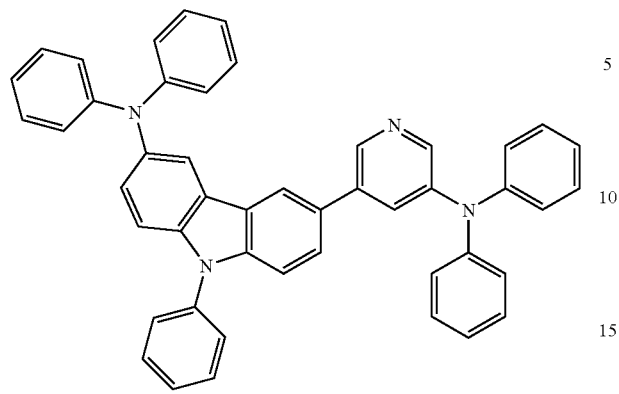

Compound (52)

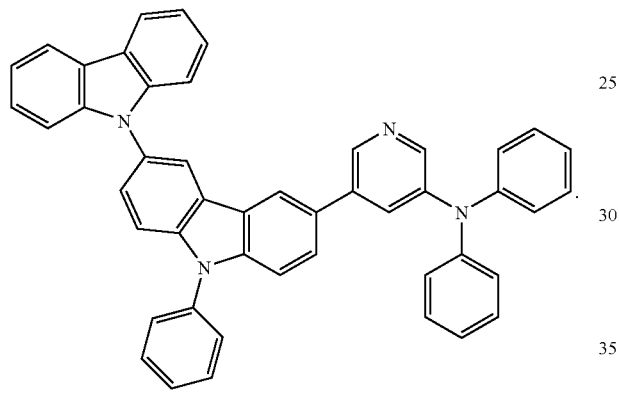

12. The material as claimed in claim 1, wherein the dopant is a phosphorescent dopant.

13. The material as claimed in claim 1, wherein the dopant is a fluorescent dopant.

14. An organic photoelectric device, comprising an anode;

a cathode; and an organic thin layer disposed between the anode and cathode, wherein the organic thin layer comprises the material as claimed in claim 1.

15. The organic photoelectric device of claim 14, wherein the organic thin layer comprises:

an emission layer; and at least one layer selected from the group consisting of a hole transport layer (HTL), a hole injection layer (HIL), an electron transport layer (ETL), an electron injection layer (EIL), and combinations thereof.

* * * * *